(12) United States Patent
McConville et al.

(10) Patent No.: US 7,425,661 B2
(45) Date of Patent: Sep. 16, 2008

(54) METHODS FOR OLIGOMERIZING OLEFINS

(75) Inventors: David H. McConville, Houston, TX (US); Lily Ackerman, San Francisco, CA (US); Robert T. Li, Houston, TX (US); Xiaohong Bei, Oak Park, CA (US); Matthew C. Kuchta, Heidelberg (DE); Tom Boussie, Menlo Park, CA (US); John F. Walzer, Jr., Seabrook, TX (US); Gary Diamond, San Jose, CA (US); Francis C. Rix, League City, TX (US); Keith A. Hall, San Jose, CA (US); Anne LaPointe, Sunnyvale, CA (US); James Longmire, San Jose, CA (US); Vince Murphy, San Jose, CA (US); Pu Sun, San Jose, CA (US); Dawn Verdugo, San Francisco, CA (US); Susan Schofer, San Francisco, CA (US); Eric Dias, Belmont, CA (US)

(73) Assignee: ExxonMobil Chemicals Patents Inc., Houston, TX (US)

( * ) Notice: Subject to any disclaimer, the term of this patent is extended or adjusted under 35 U.S.C. 154(b) by 14 days.

(21) Appl. No.: 11/371,983

(22) Filed: Mar. 9, 2006

(65) Prior Publication Data

US 2006/0247483 A1    Nov. 2, 2006

Related U.S. Application Data

(60) Provisional application No. 60/660,018, filed on Mar. 9, 2005.

(51) Int. Cl.
C07C 2/08 (2006.01)
C07C 2/26 (2006.01)
B01J 31/02 (2006.01)

(52) U.S. Cl. .................. 585/527; 585/513; 502/103; 502/123; 502/168

(58) Field of Classification Search ............ 502/167, 502/152, 103, 123; 585/513, 527
See application file for complete search history.

(56) References Cited

U.S. PATENT DOCUMENTS

| | | |
|---|---|---|
| 3,300,458 A | 1/1967 | Manyik et al. |
| 3,333,016 A | 7/1967 | Schultz |
| 4,472,525 A | 9/1984 | Singleton |
| 4,668,838 A | 5/1987 | Briggs |
| 4,689,437 A | 8/1987 | Murray |
| 4,777,315 A | 10/1988 | Levine et al. |
| 4,853,356 A | 8/1989 | Briggs |
| 5,137,994 A | 8/1992 | Goode et al. |
| 5,198,563 A | 3/1993 | Reagen et al. |
| 5,376,612 A | 12/1994 | Reagen et al. |
| 5,382,738 A | 1/1995 | Reagen et al. |
| 5,438,027 A | 8/1995 | Reagen et al. |
| 5,439,862 A | 8/1995 | Kemp |
| 5,451,645 A | 9/1995 | Reagen et al. |
| 5,491,272 A | 2/1996 | Tanaka et al. |
| 5,523,507 A | 6/1996 | Reagen et al. |
| 5,543,375 A | 8/1996 | Lashier et al. |
| 5,550,305 A | 8/1996 | Wu |
| 5,557,026 A | 9/1996 | Tanaka et al. |
| 5,563,312 A | 10/1996 | Knudsen et al. |
| 5,637,660 A | 6/1997 | Nagy et al. |
| 5,668,249 A | 9/1997 | Baardman et al. |
| 5,731,487 A | 3/1998 | Tamura et al. |
| 5,744,677 A | 4/1998 | Wu |
| 5,750,816 A | 5/1998 | Araki et al. |
| 5,750,817 A | 5/1998 | Tanaka et al. |
| 5,763,723 A | 6/1998 | Reagen et al. |
| 5,811,618 A | 9/1998 | Wu |
| 5,814,575 A | 9/1998 | Reagen et al. |
| 5,853,551 A | 12/1998 | Boucot et al. |
| 5,856,257 A | 1/1999 | Freeman et al. |
| 5,856,610 A | 1/1999 | Tamura et al. |
| 5,856,612 A | 1/1999 | Araki et al. |
| 5,859,303 A | 1/1999 | Lashier |
| 5,910,619 A | 6/1999 | Urata et al. |
| 5,919,996 A | 7/1999 | Freeman et al. |
| 5,968,866 A | 10/1999 | Wu |
| 5,968,886 A | 10/1999 | Kunz et al. |
| 6,031,145 A | 2/2000 | Commereuc et al. |

(Continued)

FOREIGN PATENT DOCUMENTS

AT    54439    7/1990

(Continued)

OTHER PUBLICATIONS

McGuinness et al., "Novel Cr-PNP complexes as catalysts for the trimerisation of ethylene", Chem. Comm. 2003, pp. 334-335.

(Continued)

Primary Examiner—Caixia Lu

(57) ABSTRACT

The present invention provides a method of producing oligomers of olefins, comprising reacting olefins with a catalyst under oligomerization conditions. The catalyst can be the product of the combination of a chromium compound and a pyridyl amine or a heteroaryl-amine compound. In particular embodiments, the catalyst compound can be used to trimerize or tetramerize ethylene to 1-hexene, 1-octene, or mixtures of 1-hexene and 1-octene.

9 Claims, 8 Drawing Sheets

U.S. PATENT DOCUMENTS

| | | |
|---|---|---|
| 6,103,657 A | 8/2000 | Murray |
| 6,133,495 A | 10/2000 | Urata et al. |
| 6,136,748 A | 10/2000 | Smith |
| 6,265,513 B1 | 7/2001 | Murray et al. |
| 6,268,447 B1 | 7/2001 | Murray et al. |
| 6,277,841 B1 | 8/2001 | Rajagopalan et al. |
| 6,303,719 B1 | 10/2001 | Murray et al. |
| 6,320,002 B1 | 11/2001 | Murray et al. |
| 6,320,005 B1 | 11/2001 | Murray |
| 6,337,297 B1 | 1/2002 | Mimura et al. |
| 6,344,594 B1 | 2/2002 | Sen et al. |
| 6,380,451 B1 | 4/2002 | Kreischer et al. |
| 6,437,161 B1 | 8/2002 | Mihan et al. |
| 6,455,648 B1 | 9/2002 | Freeman et al. |
| 6,489,263 B2 | 12/2002 | Murray et al. |
| 6,521,806 B1 | 2/2003 | Tamura et al. |
| 6,583,083 B2 | 6/2003 | Murray et al. |
| 6,610,627 B2 | 8/2003 | Murray |
| 6,706,829 B2 | 3/2004 | Boussie et al. |
| 6,713,577 B2 | 3/2004 | Boussie et al. |
| 6,727,361 B2 | 4/2004 | LaPointe et al. |
| 6,750,345 B2 | 6/2004 | Boussie et al. |
| 6,800,702 B2 | 10/2004 | Wass |
| 6,828,269 B2 | 12/2004 | Commereuc et al. |
| 6,828,397 B2 | 12/2004 | Boussie et al. |
| 6,844,290 B1 | 1/2005 | Maas et al. |
| 6,900,152 B2 | 5/2005 | Yoshida et al. |
| 7,214,842 B2 | 5/2007 | Mihan et al. |
| 2001/0034297 A1 | 10/2001 | Murray et al. |
| 2002/0035029 A1 | 3/2002 | Yoshida et al. |
| 2002/0065379 A1 | 5/2002 | Murray |
| 2002/0137845 A1 | 9/2002 | Boussie et al. |
| 2002/0142912 A1 | 10/2002 | Boussie et al. |
| 2002/0147288 A1 | 10/2002 | Boussie et al. |
| 2002/0156279 A1 | 10/2002 | Boussie et al. |
| 2002/0173419 A1 | 11/2002 | Boussie et al. |
| 2002/0177711 A1 | 11/2002 | LaPointe et al. |
| 2002/0183574 A1 | 12/2002 | Dixon et al. |
| 2003/0130551 A1 | 7/2003 | Drochon et al. |
| 2003/0149198 A1 | 8/2003 | Small et al. |
| 2003/0153697 A1 | 8/2003 | Boussie et al. |
| 2003/0166456 A1 | 9/2003 | Wass |
| 2004/0122247 A1 | 6/2004 | Boussie et al. |
| 2004/0122271 A1 | 6/2004 | Van Zon et al. |
| 2004/0228775 A1 | 11/2004 | Ewert et al. |
| 2004/0236163 A1 | 11/2004 | Ewert et al. |
| 2005/0020788 A1 | 1/2005 | Wass |
| 2005/0020866 A1 | 1/2005 | Kobayashi et al. |
| 2005/0113524 A1* | 5/2005 | Stevens et al. ............ 525/240 |
| 2005/0197521 A1 | 9/2005 | Kreischer |
| 2006/0094839 A1 | 5/2006 | Diamond |
| 2006/0094867 A1 | 5/2006 | Diamond |
| 2006/0173226 A1 | 8/2006 | Blann et al. |
| 2006/0211903 A1 | 9/2006 | Blann et al. |
| 2006/0229480 A1 | 10/2006 | Blann et al. |
| 2006/0247399 A1 | 11/2006 | McConville et al. |
| 2006/0293546 A1 | 12/2006 | Nabika |
| 2007/0027350 A1 | 2/2007 | Nabika |
| 2007/0185358 A1 | 8/2007 | Buchanan et al. |
| 2007/0185364 A1 | 8/2007 | Buchanan et al. |

FOREIGN PATENT DOCUMENTS

| | | |
|---|---|---|
| AT | 237622 | 5/2003 |
| AU | 594749 | 9/1987 |
| AU | 8769893 | 9/1987 |
| AU | 735915 | 1/1999 |
| AU | 9883806 | 1/1999 |
| AU | 2002/041517 | 6/2002 |
| BR | 8701145 | 1/1988 |
| BR | 9810213 | 10/2001 |
| CA | 1273018 | 8/1990 |
| CA | 2087578 | 1/1993 |
| CA | 2115639 | 9/1994 |
| CN | 1011693 | 9/1987 |
| CN | 87101861 | 9/1987 |
| CN | 1045712 | 12/1996 |
| CN | 1256968 | 6/2000 |
| EP | 237079 | 7/1990 |
| EP | 622 347 | 11/1994 |
| EP | 668 106 | 8/1995 |
| EP | 706 983 | 4/1996 |
| EP | 0537609 | 8/1996 |
| EP | 0416304 | 3/1997 |
| EP | 0614865 | 10/1997 |
| EP | 0699648 | 4/1998 |
| EP | 889061 | 1/1999 |
| EP | 0780353 | 8/2000 |
| EP | 0608447 | 10/2001 |
| EP | 993464 | 4/2003 |
| EP | 1308450 | 5/2003 |
| EP | 1110930 | 9/2003 |
| EP | 1364974 | 11/2003 |
| FI | 8701125 | 9/1987 |
| GB | 2 298 864 | 9/1996 |
| HU | 44049 | 1/1988 |
| HU | 201785 | 1/1988 |
| IL | 81821 | 9/1990 |
| IN | 168364 | 3/1991 |
| JP | 4066457 | 11/1987 |
| JP | 62265237 | 11/1987 |
| JP | 7010780 | 1/1995 |
| JP | 06515873 | 3/1995 |
| JP | 07215896 | 8/1995 |
| JP | 07267881 | 10/1995 |
| JP | 09020692 | 1/1997 |
| JP | 09020693 | 1/1997 |
| JP | 09268133 | 10/1997 |
| JP | 09268134 | 10/1997 |
| JP | 09268135 | 10/1997 |
| JP | 10007593 | 1/1998 |
| JP | 10007594 | 1/1998 |
| JP | 10007595 | 1/1998 |
| JP | 10007712 | 1/1998 |
| JP | 10036431 | 2/1998 |
| JP | 10036432 | 2/1998 |
| JP | 10045638 | 2/1998 |
| JP | 10087518 | 4/1998 |
| JP | 2001/524162 | 1/1999 |
| JP | 3491761 | 1/1999 |
| JP | 11092407 | 4/1999 |
| JP | 11092408 | 4/1999 |
| JP | 11222445 | 8/1999 |
| JP | 2000176291 | 6/2000 |
| JP | 2000202299 | 7/2000 |
| JP | 2000212212 | 8/2000 |
| JP | 2001009290 | 1/2001 |
| JP | 2001/187345 | 7/2001 |
| JP | 2002045703 | 2/2002 |
| JP | 2002066329 | 3/2002 |
| JP | 2002102710 | 4/2002 |
| JP | 2002172327 | 6/2002 |
| JP | 2002200429 | 7/2002 |
| JP | 2002205960 | 7/2002 |
| JP | 2002233765 | 8/2002 |
| JP | 3351068 | 11/2002 |
| JP | 2003071294 | 3/2003 |
| JP | 3540827 | 7/2004 |
| JP | 3540828 | 7/2004 |
| JP | 3577786 | 10/2004 |
| MX | 200000017 | 12/2000 |
| NO | 167454 | 9/1987 |
| NO | 8701054 | 9/1987 |
| TW | 467921 | 12/2001 |

| | | |
|---|---|---|
| WO | WO 97/37765 | 10/1997 |
| WO | 99/01460 | 1/1999 |
| WO | WO 99/19280 | 4/1999 |
| WO | 00/37175 | 6/2000 |
| WO | 00/50470 | 8/2000 |
| WO | WO 01/10876 | 2/2001 |
| WO | 01/48028 | 7/2001 |
| WO | WO 01/47839 | 7/2001 |
| WO | 01/68572 | 9/2001 |
| WO | WO 01/83447 | 11/2001 |
| WO | 02/04119 | 1/2002 |
| WO | 02/38628 | 5/2002 |
| WO | 02/46249 | 6/2002 |
| WO | 02/066404 | 8/2002 |
| WO | 02/066405 | 8/2002 |
| WO | 02/083306 | 10/2002 |
| WO | 03/004158 | 1/2003 |
| WO | 03/053890 | 7/2003 |
| WO | 03/053891 | 7/2003 |
| WO | 2004/056477 | 7/2004 |
| WO | 2004/056478 | 7/2004 |
| WO | 2004/056479 | 7/2004 |
| WO | 2004/056480 | 7/2004 |
| WO | 2004/083263 | 9/2004 |
| WO | WO 2005/123633 | 12/2005 |
| WO | WO 2005/123884 | 12/2005 |
| WO | WO 2006/096881 | 9/2006 |
| WO | WO 2007/007272 | 1/2007 |
| ZA | 8701859 | 4/1988 |
| ZA | 9805782 | 1/1999 |

OTHER PUBLICATIONS

McGuinness et al., "First Cr(III)-SNS Complexes and their use as Highly Efficient Catalysts for the Trimerization of Ethylene to 1-Hexene", J. Am. Chem. Soc. 2003, 125, pp. 5272-5273.

Carter et al., "High activity ethylene trimerisation catalysts based on diphosphine ligands", Chem. Comm. 2002, pp. 858-859.

Agapie et al., "Mechanistic Studies of the Ethylene Trimerization Reaction with Chromium-Diphosphine Catalysts: Experimental Evidence for a Mechanism involving Metallacyclic Intermediates", J. Am. Chem. Soc. 2004, 126, pp. 1304-1305.

Yang et al., "Roles of chloro compound in homogenous [Cr92-ethylhexampate)$_3$/2,5-dimethylpyrrole/triethylaluminum/chloro compound] catalyst system for ethylene trimerization" Applied Catalysis A: General, 2000, 193, pp. 29-38.

Köhn et al., "Triazacyclohexane complexes of chromium as highly active homogeneous model systems for the Phillips catalyst†‡§", Chem. Commun., 2000, pp. 1927-1928.

Deckers et al., "Catalytic Trimerization of Ethene with Highly Active Cyclopentadienyl-Arene Titanium Catalysts", Organometallics 2002, 21, pp. 5122-5135.

Andes et al., "New Tantalum-Based Catalyst System for the Selective Trimerization of Ethene to 1-Hexene", J. Am. Chem. Soc. 2001, 123, pp. 7423-7424.

Robertson et al., "Chromium(II) and Chromium(III) Complexes Supported by Tris(2-pyridylmethyl)amine: Synthesis, Structures, and Reactivity" Inorganic Chemistry 2003, 42, pp. 6876-6885.

A. Ranwell et al., "Potential Application of Ionic Liquids for Olefin Oligomerization," ACS Symposium Series, Chapter 12, 2002, 818, pp. 147-160.

R.D. Kohn et al., 1,3,5-Triazacyclohexane Complexes of Chromium as Homogeneous Model Systems for the Phillips Catalyst, ACS Symposium Series, 2003, 857, pp. 88-100.

K.R. Dunbar et al., "Structure of [HTMPP]$_3$W$_2$CL$_9$[HTMPP=Tris(2,4,6-trimethoxyphenyl)-phosphonium]," Acta Cryst., 1991, C47, pp. 23-26.

D.H. Morgan et al., "The Effect of Aromatic Ethers on the Trimerisation of Ethylene using a Chromium Catalyst and Aryloxy Ligands," Adv. Synth. & Catalysis, 2003, 345, pp. 939-942.

H. Mahomed et al., "Ethylene trimerisation catalyst based on substituted cyclopentadienes," Applied Catalysis A: General, 2003, 255, pp. 355-359.

C.N. Nenu et al., "Single-site heterogeneous Cr-based catalyst for the selective trimerisation of ethylene," Chem. Commun., 2005, pp. 1865-1867.

K. Blann et al., "Highly selective chromium-based ethylene trimerisation catalysts with bulky diphosphinoamine ligands," Chem. Commun., 2005, pp. 620-621.

M.J. Overett et al., "Ethylene trimerisation and tetramerisation catalysts with polar-substituted diphosphinoamine ligands," Chem. Commun., 2005, pp. 622-624.

Hecheng Shuzhi Ji Suliao, China Synthetic Resin and Plastics, 2001, 18(2), 23-25, 43.

T. Imamoto et al., "Synthesis and reactions of Optically Pure Cyclohexyl (o-methoxyphenyl)phosphine-Borane and t-Butyl-(o-methoxyphenyl)phosphine-Borane," Heteroatom Chemistry, 1993, vol. 4, No. 5, pp. 475-486.

L. Hirsivaara et al., "M(CO)$_6$ (M=Cr, Mo, W) derivatives of (o-anisyl)diphenylphosphine, bis(o-anisyl)phenylphosphine tris(o-anisyl)phosphine and (p-anisyl)bis(o-anisyl)phosphine," Inorganica Chimica Acta, 2000, 307, pp. 47-56.

A. Bollmann et al., "Ethylene Tetramerization: A New Route to Produce 1-Octene in Exceptionally High Selectivities," J. Am. Chem. Soc., 126, 2004, pp. 14712-14713.

A. Ariffin et al., "The asymmetric synthesis of phosphorus- and sulfur-containing tricarbonyl($n^6$-arene) chromium complexes using the chiral base approach," J. Chem. Soc., Perkin Trans., 1, 1999, pp. 3177-3189.

T. Monoi et al., "Silica-supported Cr[N(SiMe$_3$)$_2$]$_3$/isobutylalumoxane catalyst for selective ethylene trimerization," Journal of Mol. Catalysis A: Chemical, 187, 2002, pp. 135-141.

J.T. Dixon et al., "Advances in selective ethylene trimerisation—a critical overview," Jrnl. of Organometallic Chem., 689, 2004, pp. 3641-3668.

R.M. Manyik et al., "A Soluble Chromium-Based Catalyst for Ethylene Trimerization and Polymerization," Journal of Catalysts, 1977, 47, pp. 197-209.

L. Hirsivaara et al., "Organometallic derivatives of multidentate phosphines [o-(methylthio)phenyl]diphenylphosphine and bis(o-(methylthio)phenyl(phenylphosphine: preparation and characterization of group 6 metal carbonyl derivatives," Jrnl. of Organometallic Chem., 579, 1999, pp. 45-52.

J. Pietsch et al., "Koordinationschemie funktioneller Phosphine II. Carbonyl(nitrosyl) wolfram-Komplexe mit 2-Diphenylphosphphinoanisol sowie 2-Diphenylphosphinoanilid, -benzoat und -phenolat als Liganden," Journal of Organometallic Chemistry, 495, 1995, pp. 113-125.

L. Dahlenburg et al., "Koordinationschemie funktioneller Phosphane VIII. Tetracarbonylkomplexe des Wolframs und Molybdans mit 2-(Diphenylphosphanyl)anilin-Liganden," Journal of Organometallic Chemistry, 585, 1999, pp. 225-233.

D. de Wet-Roos et al., "Homogeneous Tandem Catalysis of Bis(2-decylthioethyl)amine-Chromium Trimerization Catalyst in Combination with Metallocene Catalysts," Macromolecules, 2004, 37, pp. 9314-9320.

R. Blom et al., "1,3,5-Triazacyclohexane Complexes of Chromium as Homogeneous Model Systems for the Phillips Catalyst," Organometallic Catalysts and Olefin Polymerization, 2001, pp. 147-155.

K. Burgess, Stereochemically Matched (and Mismatched) Bisphosphine Ligands: DIOP-DIPAMP Hybrids, Organometallics, 1992, 11, pp. 3588-3600.

K.R. Dunbar et al., Carbon Monoxide Reactions of the Fluxional Phosphine Complex ($n^3$-PR$_3$)Mo(CO)$_3$ (R=2,4,6-Trimethoxyphenyl), Organometallics, 1994, 13, pp. 2713-2720.

G. Boni et al., "Heterobimetallic Dibridged Complexes [Cp$_2$Ta(u-CO)(u-PMe$_2$)M'(CO)$_4$] (M'=Cr, W): Synthesis and Reactivity toward Two-Electron Donor Ligands L (L=PR$_3$, Me$_2$P(CH$_2$)nPMe$_2$, CNR)," Organometallics, 1995, 14, pp. 5652-5656.

T. Agapie et al.; "A Chromium-Diphosphine System for Catalytic Ethylene Trimerization: Synthetic and Structural Studies of Chromium Complexes with a Nitrogen-Bridged Diphosphine Ligand with ortho-Methoxyaryl Substituents"; Organometallics, 25; 2006, pp. 2733-2742.

R.L. Wife et al., "Phosphine Oxide Anions in the Synthesis of Phosphine Ligands," Synthesis, 1983, pp. 71-73.

S. Naqvi, "1-Hexene From Ethylene By the Phillips Trimerization Technology," available on-line at http://www.sriconsulting.com/PEP/Reports/Phase_95/RW95-1-1/RW95-1-8.html, Dec. 1997.

B. L. Small et al., "New Chromium Complexes for Ethylene Oligomerization: Extended Use of Tridentate Ligands in Metal-Catalyzed Olefin Polymerization," Macromolecules, vol. 37, Nov. 12, 2004, pp. 4375-4386.

* cited by examiner

A42

A43

A44

A45

A46

A47

A48

A49

A50

A51

A52

A72

A73

A53

A54

A55

A56

A57

A58

A59

A60

A61

A62

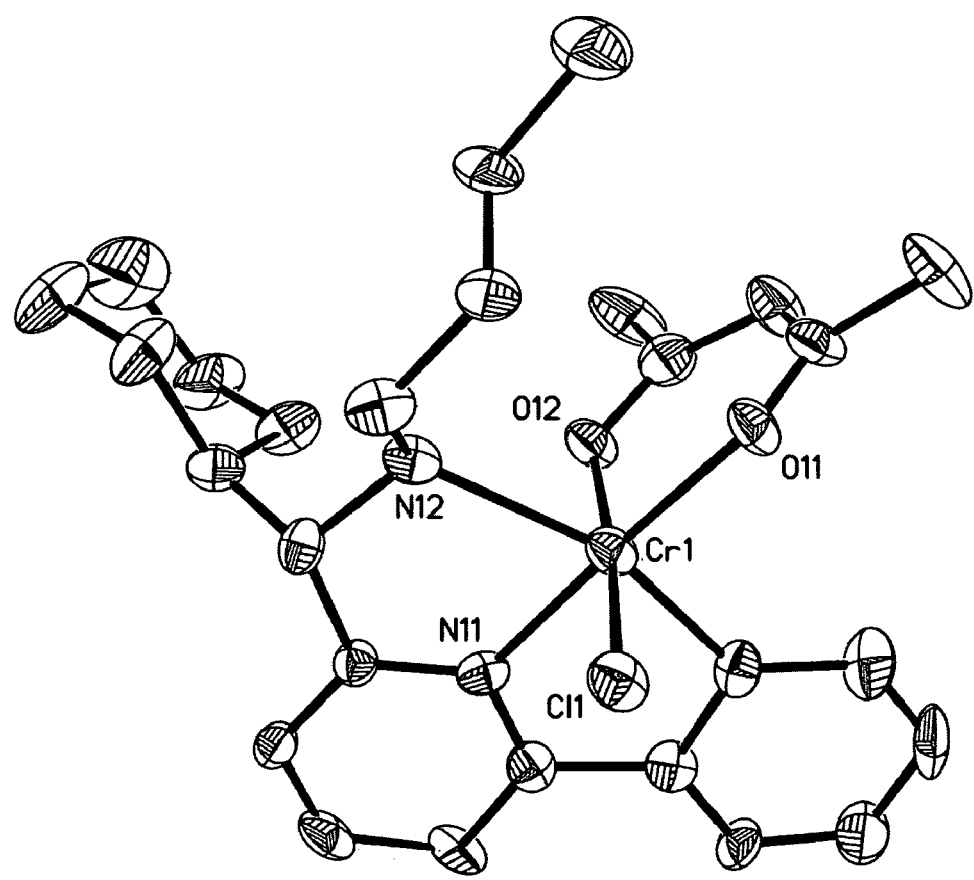
Fig. 8 The structure of M13 determined by X-ray Crystallography

METHODS FOR OLIGOMERIZING OLEFINS

PRIORITY CLAIM

This application claims the benefit of and priority to U.S. provisional application U.S. Ser. No. 60/660,018, filed Mar. 9, 2005.

FIELD OF THE INVENTION

This invention relates to the selective oligomerization (specifically trimerization and/or tetramerization) of olefins (specifically ethylene) using catalysts.

BACKGROUND OF THE INVENTION

The oligomerization of ethylene typically returns a broad distribution of 1-olefins having an even number of carbon atoms ($C_4$, $C_6$, $C_8$, $C_{10}$, etc.). These products range in commercial value, of which 1-hexene may be the most useful, as it is a comonomer commonly used in the production of commercial ethylene based copolymers.

Several catalysts useful for the oligomerization of olefin monomers have been developed, including the trimerization of ethylene. Several of these catalysts use chromium as a metal center. For example, U.S. Pat. No. 4,668,838, assigned to Union Carbide Chemicals and Plastics Technology Corporation, discloses a chromium catalyst complex formed by contacting a chromium compound with hydrolyzed hydrocarbyl aluminum and a donor ligand such as hydrocarbyl isonitriles, amines, and ethers. U.S. Pat. No. 5,137,994 discloses a chromium catalyst formed by the reaction products of bis-triarylsilyl chromates and trihydrocarbylaluminum compounds.

U.S. Pat. No. 5,198,563 and related patents, issued to Phillips Petroleum Company, disclose chromium-containing catalysts containing monodentate amide ligands. A chromium catalyst complex formed by contacting an aluminum alkyl or a halogenated aluminum alkyl and a pyrrole-containing compound prior to contacting with a chromium containing compound is disclosed in U.S. Pat. Nos. 5,382,738, 5,438,027, 5,523,507, 5,543,375, and 5,856,257. Similar catalyst complexes are also disclosed in EP0416304B1, EP0608447B1, EP0780353B1, and CA2087578.

Several patents assigned to Mitsubishi Chemicals also disclose chromium catalyst complexes formed from a chromium compound, a pyrrole ring-containing compound, an aluminum alkyl, and a halide containing compound, including U.S. Pat. Nos. 5,491,272, 5,750,817, and 6,133,495. Other catalyst complexes are formed by contacting a chromium compound with a nitrogen containing compound such as a primary or secondary amine, amide, or imide, and an aluminum alkyl, as disclosed in U.S. Pat. Nos. 5,750,816, 5,856,612, and 5,910,619.

EP0537609 discloses a chromium complex containing a coordinating polydentate ligand and an alumoxane. Similarly, CA2115639 discloses a polydentate phosphine ligand.

EP0614865B1, issued to Sumitomo Chemical Co., Ltd., discloses a catalyst prepared by dissolving a chromium compound, a heterocyclic compound having a pyrrole ring or an imidazole ring, and an aluminum compound. EP0699648B1 discloses a catalyst obtained by contacting chromium containing compound with a di- or tri-alkyl aluminum hydride, a pyrrole compound or a derivative thereof, and a group 13 (III B) halogen compound.

WO03/053890, and McGuinness et al., *J. Am. Chem. Soc.* 125, 5272-5273, (2003), disclose a chromium complex of tridentate phosphine ligands and methylalumoxane (MAO) cocatalyst. However, due to serious drawbacks in the preparation of the phosphine-containing system, the use of a thio-ether donor group to replace the phosphorus donor in the ligands was also investigated.

WO02/083306A2 discloses a catalyst formed from a chromium source, a substituted phenol, and an organoaluminum compound. WO03/004158A2 discloses a catalyst system which includes a chromium source and a ligand comprising a substituted five membered carbocyclic ring or similar derivatives.

U.S. Pat. No. 5,968,866 discloses a catalyst comprising a chromium complex which contains a coordinating asymmetric tridentate phosphane, arsane, or stibane ligand (hydrocarbyl groups) and an alumoxane. Carter et al., *Chem. Commun.*, 2002, pp. 858-859 disclosed an ethylene trimerization catalyst obtained by contacting a chromium source, ligands bearing ortho-methoxy-substituted aryl groups, and an alkyl alumoxane activator. Similarly, WO02/04119A1 discloses a catalyst comprising a source of chromium, molybdenum, or tungsten, and a ligand containing at least one phosphorus, arsenic, or antimony atom bound to at least one (hetero) hydrocarbyl group.

Other pertinent references include *J. Am. Chem. Soc.* 123, 7423-7424 (2001), WO01/68572A1, WO02/066404A1, WO04/056477, WO04/056478, WO04/056479, WO04/056480, EP1110930A1, U.S. Pat. Nos. 3,333,016, 5,439,862, 5,744,677, and 6,344,594 and U.S. Pat. App. Pub. No. 2002/0035029A1. Japanese patent application JP 2001187345A2 (Tosoh Corp., Japan) discloses ethylene trimerization catalysts comprising chromium complexes having ligands which are amines substituted with two (pyrazol-1-yl)methyl groups.

Although each of the above described catalysts is useful for the trimerization of ethylene, there remains a desire to improve the performance of olefin oligomerization catalysts from the standpoint of productivity and selectivity for oligomers such as 1-hexene or 1-octene.

Several pyridyl amine catalyst complexes have been disclosed for the polymerization or copolymerization of ethylene, propylene, isobutylene, octene, and styrene by Symyx Technologies, Inc. in U.S. Pat. Nos. 6,713,577, 6,750,345, 6,706,829, 6,727,361, and 6,828,397. Pyridyl amines were also disclosed in U.S. Pat. Nos. 6,103,657 and 6,320,005, assigned to Union Carbide Chemical and Plastics Technology Corporation, in which zirconium was used as the metal center, and the catalyst complex was used to polymerize alpha-olefins, and in U.S. Pat. No. 5,637,660, assigned to Lyondell Petrochemical Company, which also describes Group 4 complexes of pyridyl amine ligands. Robertson et al., *Inorg. Chem.* 42, pp 6875-6885 (2003), discloses chromium complexes of tris(2-pyridylmethyl)amine for ethylene polymerization.

This invention also relates to U.S. Patent Application Ser. No. 60/611,943, Ser. Nos. 11/232,982 and 11/233,227.

What is needed is a catalyst system that can be readily prepared and that selectively oligomerizes ethylene or other olefins with both high activity and high selectivity.

SUMMARY OF THE INVENTION

The present invention provides methods and compositions to produce oligomers of olefins, comprising reacting olefins with a catalyst system under oligomerization conditions. The oligomerization reaction can have a selectivity of at least 70 mole percent for the desired oligomer. Typically the catalyst system is formed from the combination of:

1) a ligand characterized by the following general formula:

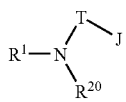

where $R^1$ and $R^{20}$ can each be independently selected from the group consisting of hydrogen and optionally substituted alkyl, heteroalkyl, cycloalkyl, heterocycloalkyl, aryl, heteroaryl, silyl and combinations thereof, provided that $R^1$ or $R^{20}$ do not equal T-J, where T-J can be as given by the general formula above and defined below; T can be a bridging group of the general formula $—(T'R^2R^3)—$, where T' is selected from the group consisting of carbon and silicon, $R^2$ and $R^3$ can each be independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, provided that two or more $R^2$ and/or $R^3$ groups may be joined together to form one or more optionally substituted ring systems having from 3-50 non-hydrogen atoms; J can be an optionally substituted six-membered heterocycle, containing at least one nitrogen atom as part of the ring;

2) a metal precursor compound characterized by the general formula $Cr(L)_n$ where each L can be independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, wherein two or more L groups may be combined in a ring structure having from 3 to 50 non-hydrogen atoms; n is 1, 2, 3, 4, 5, or 6; and 3) optionally, one or more activators.

In one embodiment, the ligand, as shown above, can be characterized by the following general formula, where J is a pyridyl or substituted pyridyl group:

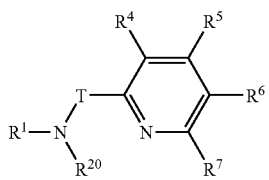

where $R^1$, $R^{20}$, and T are as described above; and $R^4$, $R^5$, $R^6$ and $R^7$ can each be independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, and optionally two or more $R^1$, $R^{20}$, $R^2$, $R^3$, $R^4$, $R^5$, $R^6$ and $R^7$ groups may be joined to form one or more optionally substituted ring systems.

In one embodiment, $R^1$ and $R^{20}$ can each be independently selected from hydrogen and optionally substituted alkyl, heteroalkyl, aryl, heteroaryl, silyl and combinations thereof.

In another embodiment, $R^1$ and $R^{20}$ can each be independently a ring having from 4-8 atoms in the ring generally selected from the group consisting of substituted cycloalkyl, heterocycloalkyl, aryl, and heteroaryl.

In another embodiment, $R^7$ can be selected from the group consisting of optionally substituted aryl and heteroaryl.

In still another embodiment, $R^1$ and $R^{20}$ can each be independently selected from hydrogen and optionally substituted alkyl groups.

In yet another embodiment, $R^1$ and $R^{20}$ may optionally be joined in a ring structure having from 3-50 non-hydrogen atoms.

In another embodiment, $R^1$ is not hydrogen when $R^{20}$ is a cyclic group.

In still another embodiment, $R^{20}$ is not a hydrogen when $R^1$ is a cyclic group.

The ligand used in various embodiments of the present invention can be selected from the group consisting of the pyridyl-amine ligands A1-A75 seen in FIGS. 1-7, especially ligands A4, A5, A23, A28, A29, A30, and A38.

The activator used in the method of the present invention can be selected from the group consisting of modified methylalumoxane (MMAO), methylalumoxane (MAO), trimethylaluminum (TMA), triisobutyl aluminum (TIBA), polymethylalumoxane-IP (PMAO), N,N-di(n-decyl)-4-n-butyl-anilinium tetrakis(perfluorophenyl)borate, and mixtures thereof.

The metal precursor used in the method of the present invention can be selected from the group consisting of $(THF)_3CrMeCl_2$, $(THF)_3CrCl_3$, $(Mes)_3Cr(THF)$, $[\{TFA\}_2Cr(OEt_2)]_2$, $(THF)_3CrPh_3$, and mixtures thereof.

The method of the present invention can oligomerize, e.g. trimerize or tetramerize, $C_2$ to $C_{12}$ olefins. In one embodiment of the present invention, the olefin can be ethylene. The oligomerization or ethylene can produce 1-hexene, 1-octene, or mixtures thereof. The reaction in the method of the present invention can occur in a hydrocarbon solvent.

Further aspects of this invention will be evident to those of skill in the art upon review of this specification.

BRIEF DESCRIPTION OF THE DRAWINGS

FIG. 8 illustrates an X-ray crystallography of a Cr complex, M18.

DETAILED DESCRIPTION

Figure 1:
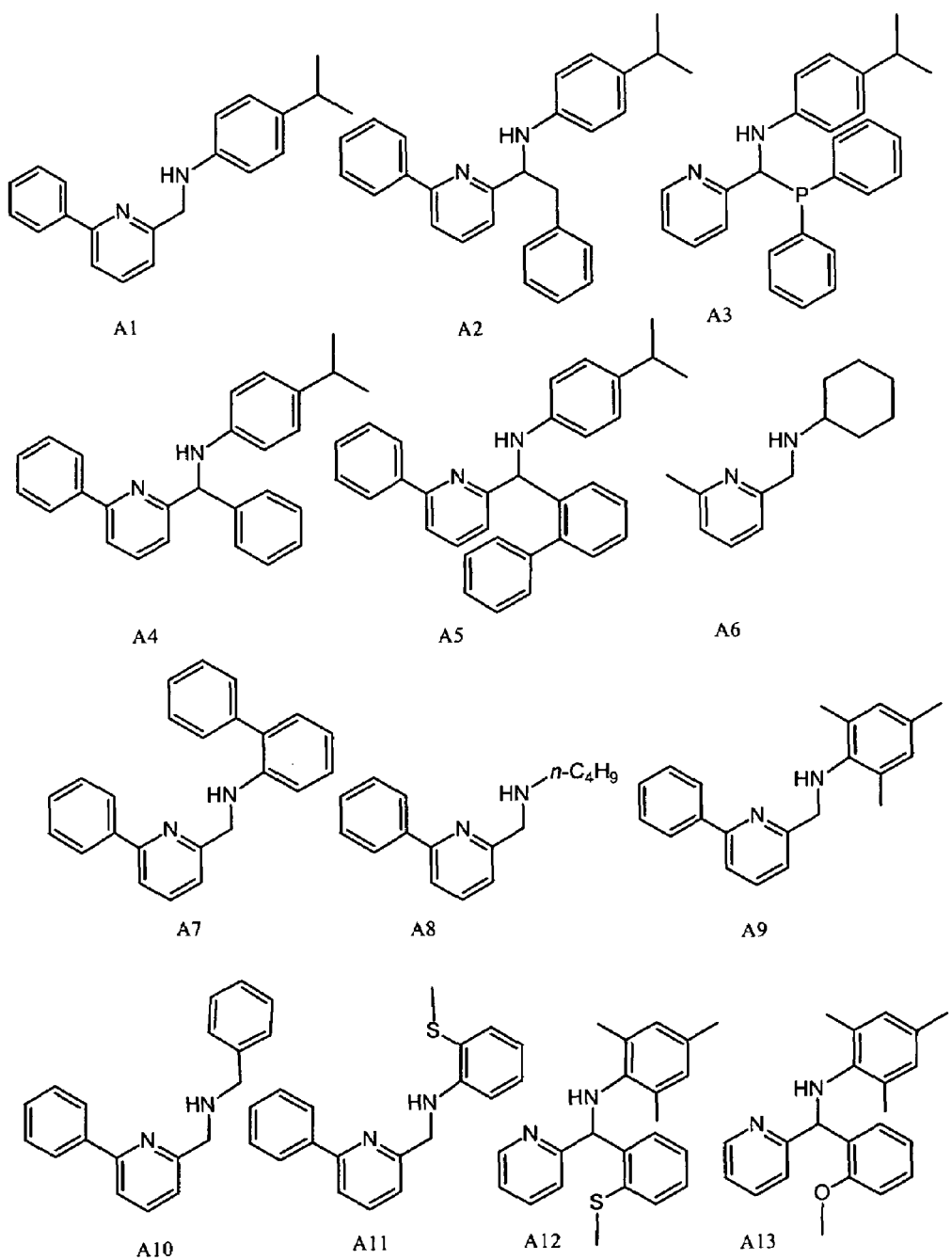
FIG. 1 illustrates pyridyl-amine ligands A1-A13 according to embodiments of the invention.
Figure 2:
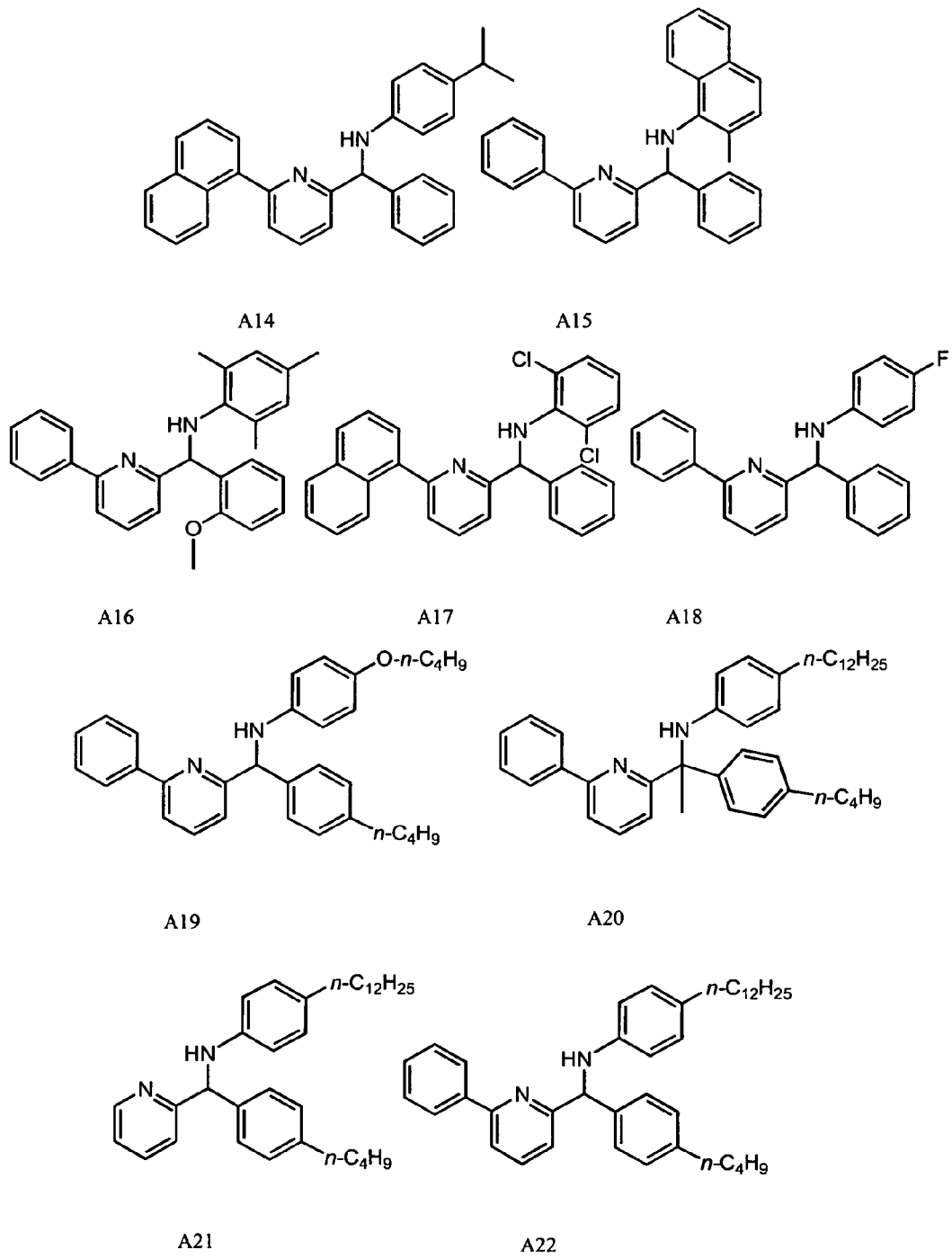
FIG. 2 illustrates pyridyl-amine ligands A14-A22 according to embodiments of the invention.
Figure 3:
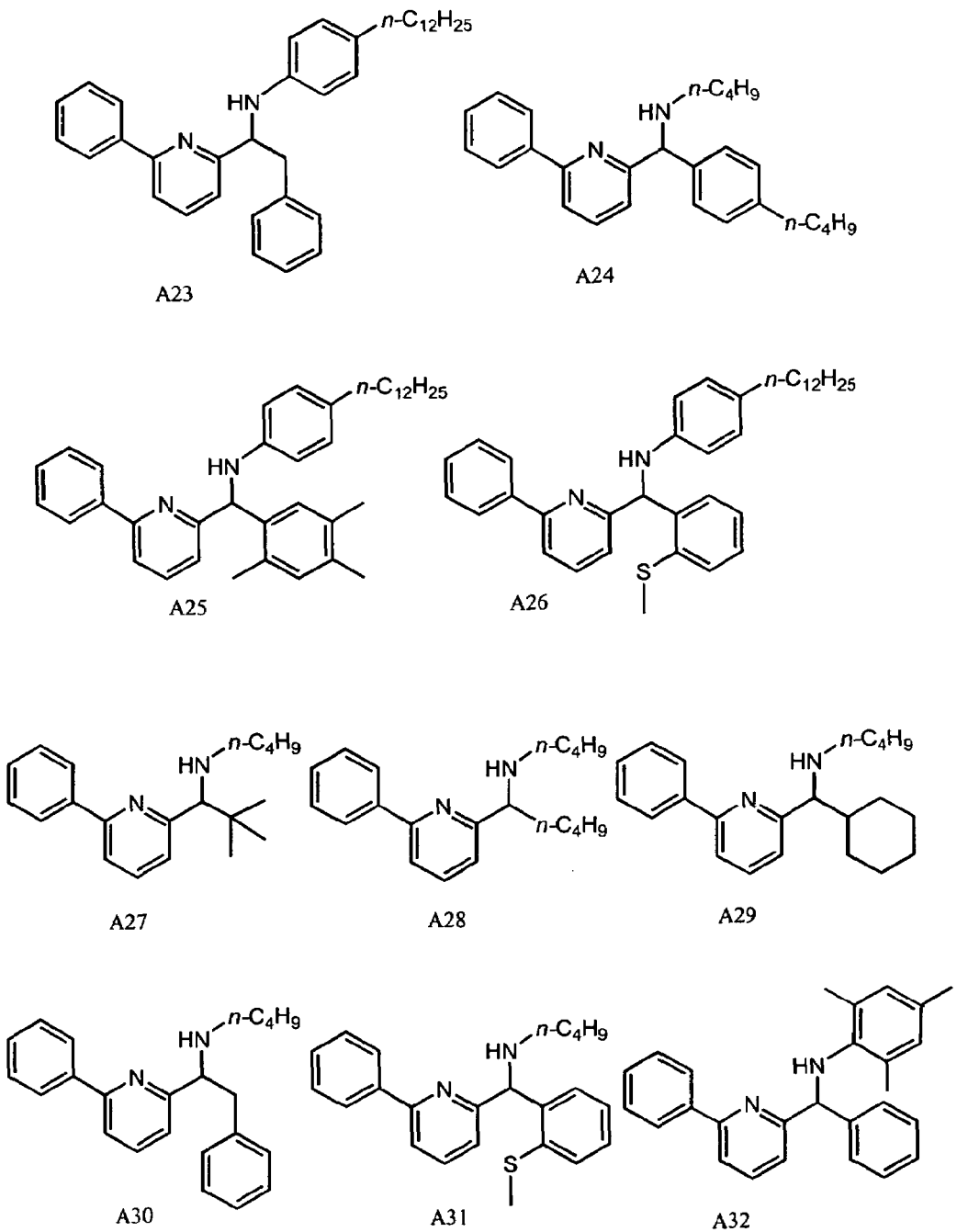
FIG. 3 illustrates pyridyl-amine ligands A23-A32 according to embodiments of the invention.
Figure 4:
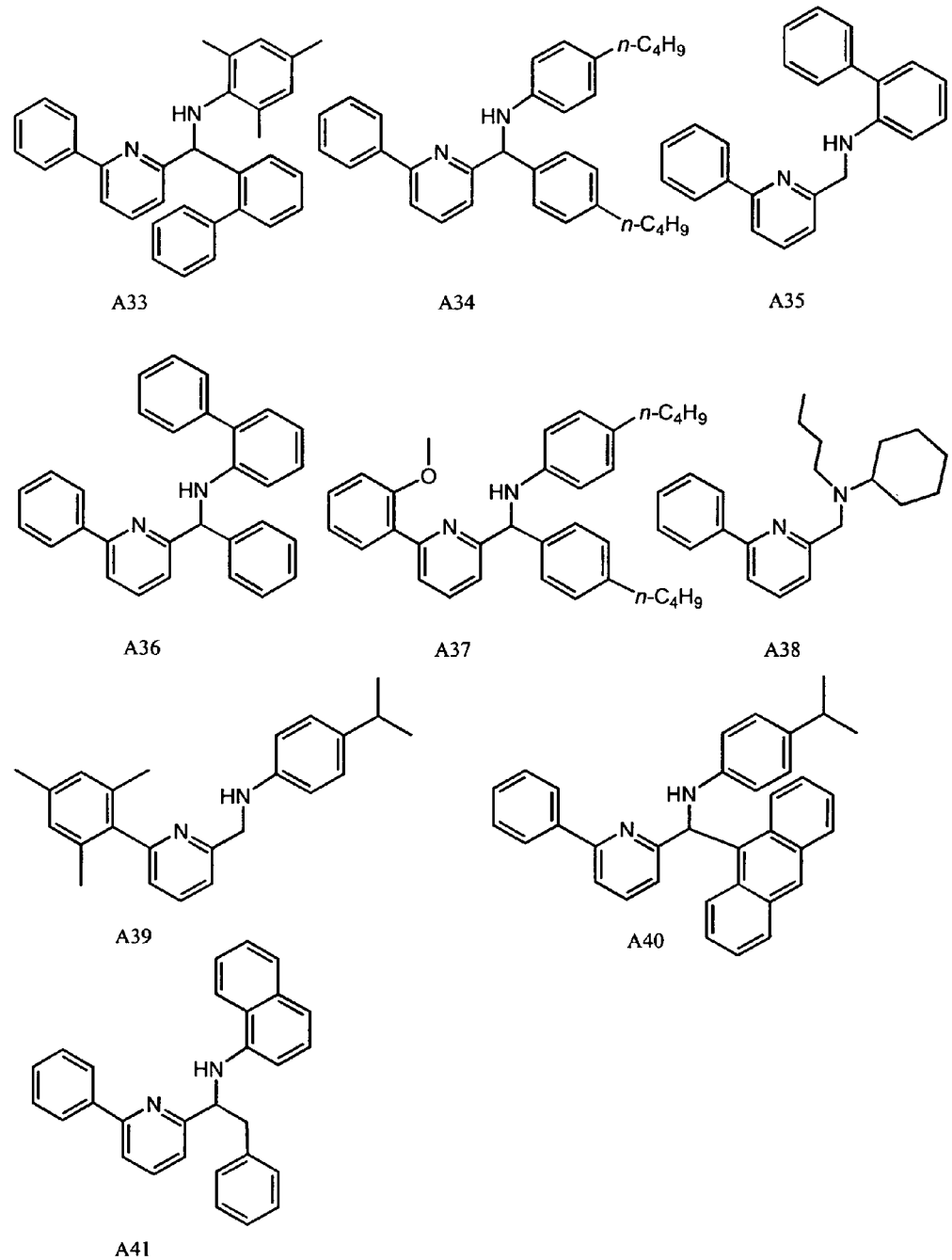
FIG. 4 illustrates pyridyl-amine ligands A33-A41 according to embodiments of the invention.
Figure 5:
FIG. 5 illustrates pyridyl-amine ligands A42-A52 according to embodiments of the invention.
Figure 5:
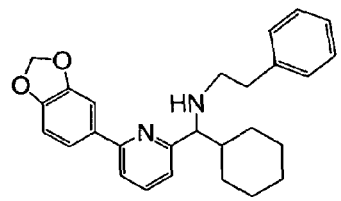
Figure 5:
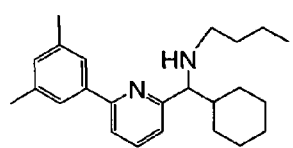
Figure 5:
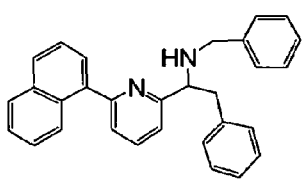
Figure 5:
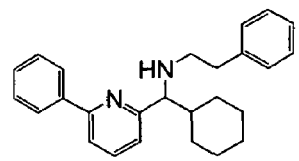
Figure 5:
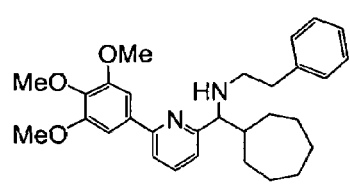
Figure 5:
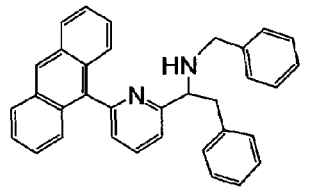
Figure 5:
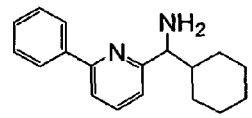
Figure 5:
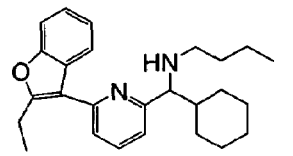
Figure 5:
Figure 5:
Figure 5:
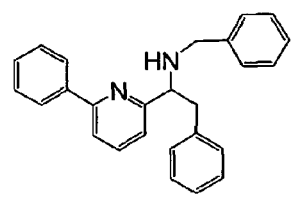
Figure 5:
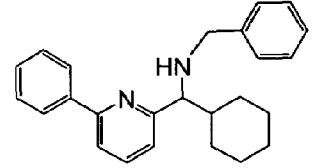

The inventions disclosed herein include chromium metal complexes and compositions, which are useful as catalysts for the selective oligomerization of olefins, specifically C2 to C12 olefins and especially C2 to C8 olefins, including the trimerization and/or tetramerization of ethylene.

For the purposes of this invention and the claims thereto when an oligomeric material (such as a dimer, trimer, or tetramer) is referred to as comprising an olefin, the olefin present in the material is the reacted form of the olefin. Likewise, the active species in a catalytic cycle may comprise the neutral or ionic forms of the catalyst. In addition, a reactor is any container(s) in which a chemical reaction occurs.

As used herein, the new numbering scheme for the Periodic Table Groups is used as set out in CHEMICAL AND ENGINEERING NEWS, 63(5), 27 (1985).

As used herein, the phrase "characterized by the formula" is not intended to be limiting and is used in the same way that "comprising" is commonly used. The term "independently selected" is used herein to indicate that the groups in question—e.g., $R^1$, $R^2$, $R^3$, $R^4$, and $R^5$—can be identical or different (e.g., $R^1$, $R^2$, $R^3$, $R^4$, and $R^5$ may all be substituted alkyls, or $R^1$ and $R^2$ may be a substituted alkyl and $R^3$ may be an aryl, etc.). Use of the singular includes use of the plural and vice versa (e.g., a hexane solvent, includes hexanes). A named R group will generally have the structure that is recognized in the art as corresponding to R groups having that name. The terms "compound" and "complex" are generally used interchangeably in this specification, but those of skill in the art may recognize certain compounds as complexes and vice versa. In addition, the term "catalyst" will be understood by those of skill in the art to include either activated or unactivated forms of the molecules the comprise the catalyst, for example, a procatalyst and including complexes and activators or compositions of ligands, metal precursors and activators and optionally including scavengers and the like. For purposes of this invention, a catalyst system is defined to be the combination of an activator and a metal ligand complex or the combination of an activator, a ligand and a metal precursor. A metal ligand complex is defined to be the product of the combination of a metal precursor and a ligand. For the purposes of illustration, representative certain groups are defined herein. These definitions are intended to supplement and illustrate, not preclude, the definitions known to those of skill in the art.

"Optional" or "optionally" means that the subsequently described event or circumstance may or may not occur, and that the description includes instances where the event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "substituted" as in "substituted hydrocarbyl," "substituted aryl," "substituted alkyl," and the like, means that in the group in question (i.e., the hydrocarbyl, alkyl, aryl or other moiety that follows the term), at least one hydrogen atom bound to a carbon atom is replaced with one or more substituent groups such as hydroxy, alkoxy, alkylthio, phosphino, amino, halo, silyl, and the like. When the term "substituted" introduces a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

The term "saturated" refers to the lack of double and triple bonds between atoms of a radical group such as ethyl, cyclohexyl, pyrrolidinyl, and the like. The term "unsaturated" refers to the presence of one or more double and triple bonds between atoms of a radical group such as vinyl, allyl, acetylide, oxazolinyl, cyclohexenyl, acetyl and the like, and specifically includes alkenyl and alkynyl groups, as well as groups in which double bonds are delocalized, as in aryl and heteroaryl groups as defined below.

The terms "cyclo" and "cyclic" are used herein to refer to saturated or unsaturated radicals containing a single ring or multiple condensed rings. Suitable cyclic moieties include, for example, cyclopentyl, cyclohexyl, cyclooctenyl, bicyclooctyl, phenyl, napthyl, pyrrolyl, furyl, thiophenyl, imidazolyl, and the like. In particular embodiments, cyclic moieties include between 3 and 200 atoms other than hydrogen, between 3 and 50 atoms other than hydrogen or between 3 and 20 atoms other than hydrogen.

The term "hydrocarbyl" as used herein refers to hydrocarbyl radicals containing 1 to about 50 carbon atoms, specifically 1 to about 24 carbon atoms, most specifically 1 to about 16 carbon atoms, including branched or unbranched, cyclic or acyclic, saturated or unsaturated species, such as alkyl groups, alkenyl groups, aryl groups, and the like.

The term "alkyl" as used herein refers to a branched or unbranched saturated hydrocarbon group typically although not necessarily containing 1 to about 50 carbon atoms, such as methyl, ethyl, n-propyl, isopropyl, n-butyl, isobutyl, sec-butyl, t-butyl, octyl, decyl, and the like, as well as cycloalkyl groups such as cyclopentyl, cyclohexyl and the like. Generally, although again not necessarily, alkyl groups herein may contain 1 to about 20 carbon atoms.

The term "alkenyl" as used herein refers to a branched or unbranched, cyclic or acyclic hydrocarbon group typically, although not necessarily, containing 2 to about 50 carbon atoms and at least one double bond, such as ethenyl, n-propenyl, isopropenyl, n-butenyl, isobutenyl, octenyl, decenyl, and the like. Generally, although again not necessarily, alkenyl groups herein contain 2 to about 20 carbon atoms.

The term "alkynyl" as used herein refers to a branched or unbranched, cyclic or acyclic hydrocarbon group typically although not necessarily containing 2 to about 50 carbon atoms and at least one triple bond, such as ethynyl, n-propynyl, isopropynyl, n-butynyl, isobutynyl, octynyl, decynyl, and the like. Generally, although again not necessarily, alkynyl groups herein may have 2 to about 20 carbon-atoms.

The term "aromatic" is used in its usual sense, including unsaturation that is essentially delocalized across several bonds around a ring. The term "aryl" as used herein refers to a group containing an aromatic ring. Aryl groups herein include groups containing a single aromatic ring or multiple aromatic rings that are fused together, linked covalently, or linked to a common group such as a methylene or ethylene moiety. More specific aryl groups contain one aromatic ring or two or three fused or linked aromatic rings, e.g., phenyl, naphthyl, biphenyl, anthracenyl, or phenanthrenyl. In particular embodiments, aryl substituents include 1 to about 200 atoms other than hydrogen, typically 1 to about 50 atoms other than hydrogen, and specifically 1 to about 20 atoms other than hydrogen. In some embodiments herein, multi-ring moieties are substituents and in such embodiments the multi-ring moiety can be attached at an appropriate atom. For example, "naphthyl" can be 1-naphthyl or 2-naphthyl; "anthracenyl" can be 1-anthracenyl, 2-anthracenyl or 9-anthracenyl; and "phenanthrenyl" can be 1-phenanthrenyl, 2-phenanthrenyl, 3-phenanthrenyl, 4-phenanthrenyl, or 9-phenanthrenyl.

The term "alkoxy" as used herein intends an alkyl group bound through a single, terminal ether linkage; that is, an "alkoxy" group may be represented as —O-alkyl where alkyl is as defined above. The term "aryloxy" is used in a similar fashion, and may be represented as —O-aryl, with aryl as defined below. The term "hydroxy" refers to —OH.

Similarly, the term "alkylthio" as used herein intends an alkyl group bound through a single, terminal thioether linkage; that is, an "alkylthio" group may be represented as —S-alkyl where alkyl is as defined above. The term "arylthio" is used similarly, and may be represented as —S-aryl, with aryl as defined below. The term "mercapto" refers to —SH.

The terms "halo" and "halogen" are used in the conventional sense to refer to a chloro, bromo, fluoro or iodo radical.

The terms "heterocycle" and "heterocyclic" refer to a cyclic radical, including ring-fused systems, including heteroaryl groups as defined below, in which one or more carbon atoms in a ring is replaced with a heteroatom—that is, an atom other than carbon, such as nitrogen, oxygen, sulfur, phosphorus, boron or silicon. Heterocycles and heterocyclic groups include saturated and unsaturated moieties, including heteroaryl groups as defined below. Specific examples of heterocycles include pyridine, pyrrolidine, pyrroline, furan, tetrahydrofuran, thiophene, imidazole, oxazole, thiazole, indole, and the like, including any isomers of these. Additional heterocycles are described, for example, in Alan R. Katritzky, *Handbook of Heterocyclic Chemistry*, Pergammon Press, 1985, and in *Comprehensive Heterocyclic Chemistry*, A. R. Katritzky et al., eds., Elsevier, 2d. ed., 1996. The term "metallocycle" refers to a heterocycle in which one or more of the heteroatoms in the ring or rings is a metal.

The term "heteroaryl" refers to an aryl radical that includes one or more heteroatoms in the aromatic ring. Specific heteroaryl groups include groups containing heteroaromatic rings such as thiophene, pyridine, pyrazine, isoxazole, pyrazole, pyrrole, furan, thiazole, oxazole, imidazole, isothiazole, oxadiazole, triazole, and benzo-fused analogues of these rings, such as indole, carbazole, benzofuran, benzothiophene and the like.

More generally, the modifiers "hetero" and "heteroatom-containing", as in "heteroalkyl" or "heteroatom-containing hydrocarbyl group" refer to a molecule or molecular fragment in which one or more carbon atoms is replaced with a heteroatom. Thus, for example, the term "heteroalkyl" refers to an alkyl substituent that is heteroatom-containing. When the term "heteroatom-containing" introduces a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

By "divalent" as in "divalent hydrocarbyl", "divalent alkyl", "divalent aryl" and the like, is meant that the hydrocarbyl, alkyl, aryl or other moiety is bonded at two points to atoms, molecules or moieties with the two bonding points being covalent bonds.

As used herein the term "silyl" refers to the —SiZ$^1$Z$^2$Z$^3$ radical, where each of Z$^1$, Z$^2$, and Z$^3$ is independently selected from the group consisting of hydrogen and optionally substituted alkyl, alkenyl, alkynyl, heteroatom-containing alkyl, heteroatom-containing alkenyl, heteroatom-containing alkynyl, aryl, heteroaryl, alkoxy, aryloxy, amino, silyl and combinations thereof.

As used herein the term "boryl" refers to the —BZ$^1$Z$^2$ group, where each of Z$^1$ and Z$^2$ is as defined above. As used herein, the term "phosphino" refers to the group —PZ$^1$Z$^2$, where each of Z$^1$ and Z$^2$ is as defined above. As used herein, the term "phosphine" refers to the group :PZ$^1$Z$^2$Z$^3$, where each of Z$^1$, Z$^3$ and Z$^2$ is as defined above. The term "amino" is used herein to refer to the group —NZ$^1$Z$^2$, where each of Z$^1$ and Z$^2$ is as defined above. The term "amine" is used herein to refer to the group :NZ$^1$Z$^2$Z$^3$, where each of Z$^1$, Z$^2$ and Z$^3$ is as defined above.

In this specification, the metal-ligand complexes are sometimes referred to as, for example, (2,1) complexes or (3,1) complexes, with the first number representing the number of coordinating atoms and second number representing the number of anionic sites on the heterocycle-amine ligand, when the metal-ligand bonding is considered from an ionic bonding model perspective, with the metal considered to be cationic and the ligand considered to be anionic. From a covalent bonding model perspective, a (2,1) complex may be considered to be a complex in which the heterocycle-amine ligand is bound to the metal center via one covalent bond and one dative bond, while a (3,1) complex may be considered to be a complex in which the heterocycle-amine ligand is bound to the metal center via one covalent bond and two dative bonds.

Throughout the Figures and the following text, several abbreviations may be used to refer to specific compounds or elements. Abbreviations for atoms are as given in the periodic table (Li=lithium, for example). Other abbreviations that may be used are as follows: "i-Pr" to refer to isopropyl; "t-Bu" to refer to tertiary-butyl; "i-Bu" to refer to isobutyl; "Me" to refer to methyl; "Et" to refer to ethyl; "Ph" to refer to phenyl; "Mes" to refer to mesityl (2,4,6-trimethyl phenyl); "TFA" to refer to trifluoroacetate; "THF" to refer to tetrahydrofuran; "TsOH" to refer to para-toluenesulfonic acid; "cat." to refer to catalytic amount of; "LDA" to refer to lithium diisopropylamide; "DMF" to refer to dimethylformamide; "eq." to refer to molar equivalents; "TMA" to refer to AlMe$_3$; "TIBA" to refer to Al i-(Bu)$_3$. SJ$_2$BF$_{20}$ refers to [(n-C$_{10}$H$_{21}$)$_2$(4-n-C$_4$H$_9$—C$_6$H$_4$)NH][B(C$_6$F$_5$)$_4$].

This invention relates to methods for selectively oligomerizing (e.g., trimerizing and/or tetramerizing) C$_2$ to C$_{12}$ olefins, specifically ethylene, comprising reacting a catalytic composition or compound(s), optionally with one or more activators, with the olefin. As referred to herein, selective oligomerization refers to producing the desired oligomer with a selectivity of the reaction being at least 70%, more specifically at least 80% by mole of oligomer, with the possibility that an acceptable amount of polymer is present, but with the preference that no polymer is present in the product. In other embodiments, less than 20 weight % of polymer is present, specifically less than 5 weight %, more specifically less than 2 weight %, based upon the total weight of monomer converted to oligomers and polymers, where a polymer is defined to mean a molecule comprising more than 100 mers. In other embodiments, selective oligomerization refers to producing two desired oligomers, with the selectivity of the two desired oligomers summing to at least 80% by sum of mole of oligomers.

In another embodiment, this invention relates to a method to trimerize or tetramerize a C$_2$ to C$_{12}$ olefin wherein the method produces at least 70% selectivity for the desired oligomer(s) (specifically at least 80%, specifically at least 85%, specifically at least 90%, specifically at least 95%, specifically at least 98%, specifically at least 99%, specifically 100%), calculated based upon the amount of the desired oligomer produced relative to the total yield; and at least 70% of the olefin monomer reacts to form product (specifically at least 80%, specifically at least 85%, specifically at least 90%, specifically at least 95%, specifically at least 98%, specifically at least 99%, specifically 100%).

This invention may also relate to novel metal ligand complexes and or novel combinations of specific ligands disclosed herein and metal precursors.

The methods of this invention specifically contact the desired monomers with a metal ligand complex or a combination of a ligand and a metal precursor (and optional activators) to form the desired oligomer. Preferred ligands useful in the present invention may be characterized by the general formula:

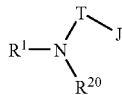
(I)

where $R^1$ and $R^{20}$ are each independently selected from the group consisting of hydrogen and optionally substituted hydrocarbyl, heteroatom containing hydrocarbyl and silyl. In some embodiments, $R^1$ and $R^{20}$ are each independently selected from hydrogen and optionally substituted alkyl, heteroalkyl, cycloalkyl, heterocycloalkyl, aryl, heteroaryl, silyl and combinations thereof. In certain embodiments, $R^1$ and $R^{20}$ are each independently a ring having from 4-8 atoms in the ring selected from the group consisting of substituted cycloalkyl, heterocycloalkyl, aryl and heteroaryl, provided that $R^1$ and $R^{20}$ do not equal T-J, where T-J is as shown in Formula (I) above and defined below.

T is a bridging group characterized by the general formula $-(T'R^2R^3)-$, where each T' is independently selected from the group consisting of carbon and silicon, $R^2$ and $R^3$ are independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, provided that two or more $R^2$ and/or $R^3$ groups may be joined together to form one or more optionally substituted ring systems, such as saturated, unsaturated or aromatic ring systems having from 3-50 non-hydrogen atoms (e.g., cyclopropyl, where T'=C, and $R^2$ and $R^3$ together form $-CH_2-CH_2-$; or cyclohexyl, where T'=C and the two $R^2$ groups together form $-CH_2-CH_2-CH_2-CH_2-$).

J is an optionally substituted six-membered heterocycle, containing at least one nitrogen atom as part of the ring. In some embodiments, J is specifically six-membered heteroaryl containing at least one nitrogen atom as part of the ring.

In one embodiment, J is a pyridyl or substituted pyridyl group. In this embodiment, the ligands may be characterized by the general formula:

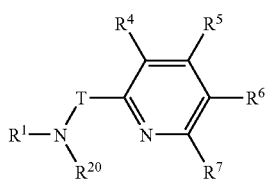
(II)

where $R^1$, $R^{20}$, and T are as described above.

$R^4$, $R^5$, $R^6$ and $R^7$ are independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, and optionally two or more $R^1$, $R^{20}$, $R^2$, $R^3$, $R^4$, $R^5$, $R^6$ and $R^7$ groups may be joined to form one or more optionally substituted ring systems.

In more specific embodiments, $R^1$ and $R^{20}$ are each independently selected from the group consisting of hydrogen, alkyl, substituted alkyl, aryl, substituted aryl, heteroaryl, substituted heteroaryl and combinations thereof. Even more specifically, $R^{20}$ is hydrogen and $R^1$ is selected from the group consisting of alkyl, substituted alkyl, aryl, and substituted aryl.

In some other embodiments, $R^2$ is hydrogen, and $R^3$ is selected from the group consisting of aryl, substituted aryl, heteroaryl, substituted heteroaryl, alkyl and substituted alkyl groups, and $-PY_2$ where Y is selected from the group consisting of aryl, substituted aryl, heteroaryl, and substituted heteroaryl.

In some embodiments, $R^1$ and $R^{20}$ are each independently selected from the group consisting of hydrogen, alkyl and substituted alkyl.

In some other embodiments, $R^7$ is specifically selected from the group consisting of optionally substituted aryl and heteroaryl.

In another embodiment, $R^1$ is not hydrogen when $R^{20}$ is a cyclic group.

In still another embodiment, $R^{20}$ is not a hydrogen when $R^1$ is a cyclic group.

Throughout this specification, the presence of one solid line and one dashed line between any pair of atoms is intended to indicate that the bond in question may be a single bond or a double bond, or a bond with bond order intermediate between single and double, such as the delocalized bonding in an aromatic ring.

The detailed synthesis of certain types of heterocycle-amine ligands are specifically discussed below, including pyridyl-amine ligands. Those of ordinary skill in the art will be able to synthesize other embodiments.

The pyridyl-amine ligands in this embodiment can be prepared according to the procedures known to those of ordinary skill in the art, for example, as described in U.S. Pat. Nos. 6,750,345, 6,713,577, and illustrated by the reaction scheme given in Scheme 1 where $R_1$, $R_2$, $R_4$, $R_5$, $R_6$, $R_7$, are as defined above and X is a halogen.

Scheme 1.

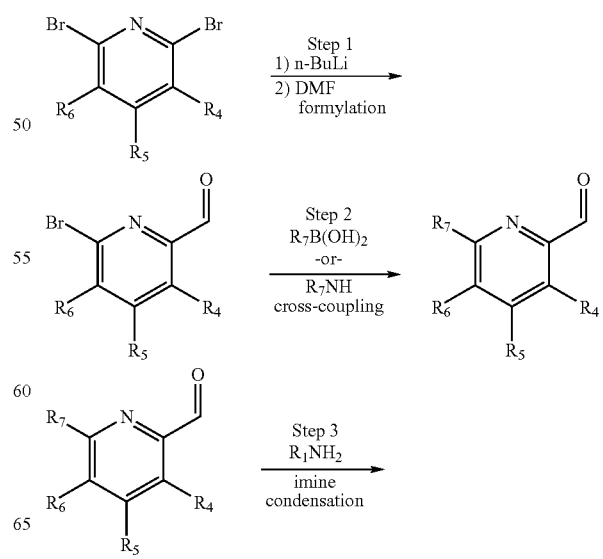

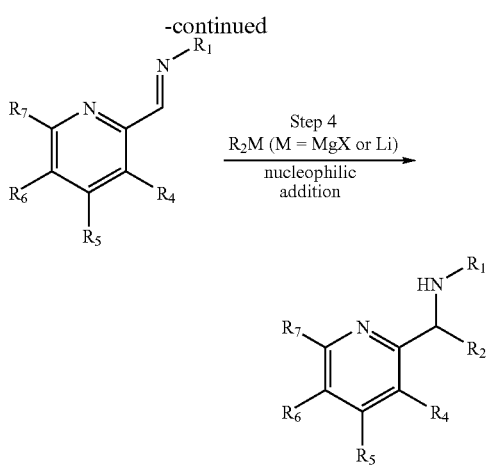

The reaction to produce a pyridyl-amine ligand can be performed in four general reaction steps. In step 1, a bromopyridine can be reacted with n-butyl lithium (n-BuLi) and DMF in a formylation reaction, replacing a bromide atom on the bromopyridine with an aldehyde group. The remaining bromide atom on the initial bromopyridine molecule can then be replaced with $R_7$ through a coupling reaction. The third reaction step is an imine-forming condensation reaction. The imine condensation reaction is followed by reaction step 4, the nucleophilic addition of $R_2$ to the structure.

Generally, $R_2M$ is a nucleophile such as an alkylating, arylating or hydrogenating reagent and M is a metal such as a main group metal, or a metalloid such as boron. The alkylating, arylating or hydrogenating reagent may be a Grignard, alkyl or aryl-lithium or borohydride reagent. In step 4, a complexing agent such as magnesium bromide can be used to direct the nucleophile selectively to the imine carbon, as described in U.S. Pat. Nos. 6,750,345 and 6,713,577. $R_3$ can be installed (into the bridging group T, and as defined above in relation to Formula (I) above) through nucleophilic addition to the appropriate ketimine, which can be obtained through a variety of known synthetic procedures, including those detailed in Method C below.

Alternative strategies to the reaction scheme illustrated in Scheme 1 can also be employed. For example, in Scheme 2, ligands where $R_{20}$ is not hydrogen may be synthesized through a condensation of the aldehyde with a secondary amine ($R_1R_{20}NH$), using benzotriazole to create a stabilized iminium salt. Nucleophilic addition of $R_2$ to the imine follows, releasing the benzotriazole adduct. An example of each type of pyridyl-amine ligand synthesis ($R_{20}$=H, $R_{20}$=alkyl) is given in Examples 1 and 2, respectively, below.

Scheme 2.

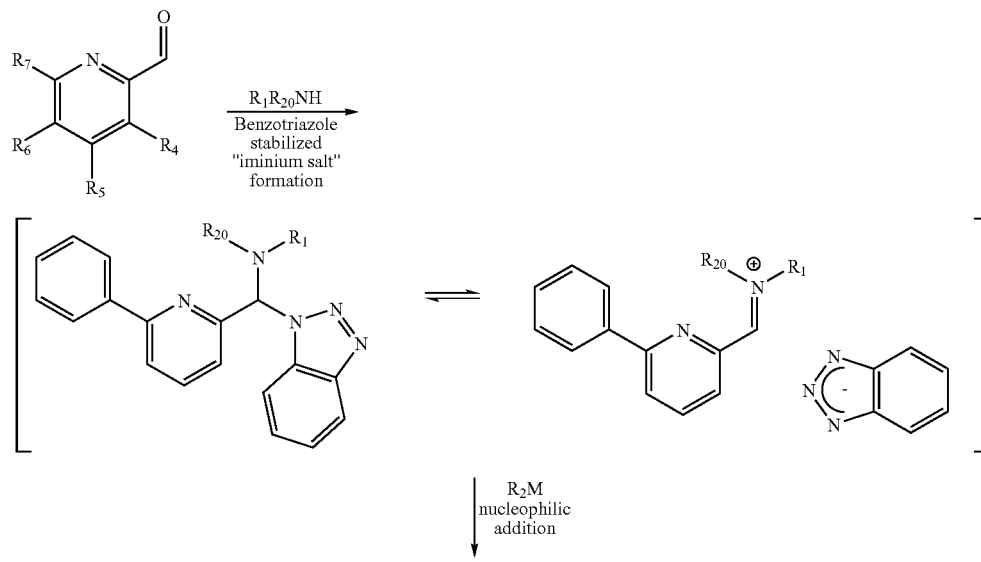

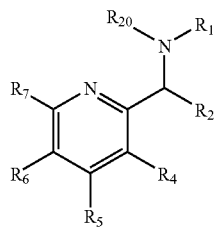

Once the desired ligand is formed, it can be combined with a Cr atom, ion, compound or other Cr precursor compound, and in some embodiments the present invention encompasses compositions that include any of the above-mentioned ligands in combination with an appropriate Cr precursor and an optional activator. For example, in some embodiments, the Cr precursor can be an activated Cr precursor, which refers to a Cr precursor (described below) that has been combined or reacted with an activator (described below) prior to combination or reaction with the ancillary ligand. As noted above, in one aspect the invention provides compositions that include such combinations of ligand and Cr atom, ion, compound or precursor. In some applications, the ligands are combined with a Cr compound or precursor and the product of such combination is not determined, if a product forms. For example, the ligand may be added to a reaction vessel at the same time as the Cr precursor compound along with the reactants, activators, scavengers, etc. Additionally, the ligand can be modified prior to addition to or after the addition of the Cr precursor, e.g., through a deprotonation reaction or some other modification.

The Cr metal precursor compounds may be characterized by the general formula $Cr(L)_n$ where L is an organic group, an inorganic group, or an anionic atom; and n is an integer of 1 to 6, and when n is not less than 2, L may be the same or different from each other. Each L is a ligand independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulfate, and combinations thereof. Optionally, two or more L groups are joined into a ring structure. One or more of the ligands L may be ionically bonded to Cr and, for example, L may be a non-coordinated or loosely coordinated or weakly coordinated anion (e.g., L may be selected from the group consisting of those anions described below in the conjunction with the activators). See Marks et al., *Chem. Rev.* 100, pp 1391-1434 (2000) for a detailed discussion of these weak interactions. The chromium precursors may be monomeric, dimeric or higher orders thereof.

Specific examples of suitable chromium precursors include, but are not limited to $(THF)_3CrMeCl_2$, $(Mes)_3Cr(THF)$, $[\{TFA\}_2Cr(OEt_2)]_2$, $(THF)_3CrPh_3$, $CrCl_3(THF)_3$, $CrCl_4(NH_3)_2$, $Cr(NMe_3)_2Cl_3$, $CrCl_3$, $Cr(acac)_3$ (acac=acetylacetonato), $Cr(2\text{-ethylhexanoate})_3$, $Cr(\text{neopentyl})_4$, $Cr(CH_2-C_6H_4\text{-o-NMe}_2)_3$, $Cr(TFA)_3$, $Cr(CH(SiMe_3)_2)_3$, $Cr(Mes)_2(THF)_3$, $Cr(Mes)_2(THF)$, $Cr(Mes)Cl(THF)_2$, $Cr(Mes)Cl(THF)_{0.5}$, $Cr(p\text{-tolyl})Cl_2(THF)_3$, $Cr(\text{diisopropylamide})_3$, $Cr(\text{picolinate})_3$, $[Cr_2Me_8][Li(THF)]_4$, $CrCl_2(THF)$, $Cr(NO_3)_3$, $[CrMe_6][Li(Et_2O)]_3$ $[CrPh_6][Li(THF)]_3$, $[CrPh_6][Li(n\text{-Bu}_2O)]_3$, $[Cr(C_4H_8)_3][Li(THF)]_3$, and other well known chromium compounds commonly used as precursors in the formation of Cr complexes and catalysts.

The ligand may be mixed with a suitable metal precursor compound prior to or simultaneously with allowing the mixture to be contacted with the reactants (e.g., monomers). In this context, the ligand to metal precursor compound ratio can be in the range of about 0.01:1 to about 100:1, more specifically in the range of about 0.1:1 to about 10:1.

Generally, the ligand (or optionally a modified ligand as discussed above) is mixed with a suitable Cr precursor (and optionally other components, such an activator, or a reagent to exchange L groups on the chromium after contact between the chromium precursor and the ligand; e.g., Li(acac)) prior to or simultaneously with allowing the mixture to be contacted with the reactants (e.g., monomers). When the ligand is mixed with the Cr precursor compound, a Cr-ligand complex may be formed, which may itself be an active catalyst or may be transformed into a catalyst upon activation. In some embodiments the Cr precursor is contacted with other ligands, then activators, then monomers.

Cr-ligand complexes can take a number of different coordination modes. General examples of possible coordination modes include those characterized by the following general formulas:

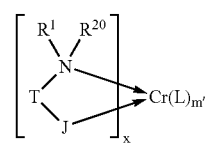

VI (a)

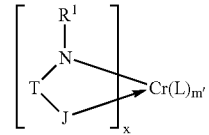

VI (b)

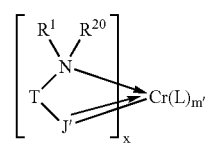

VI (c)

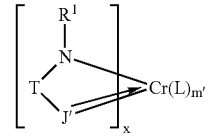

VI (d)

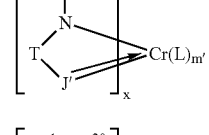

VI (e)

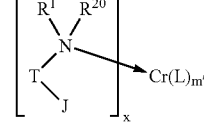

VI (f)

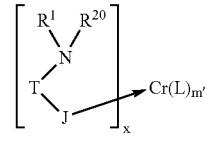

VI (g)

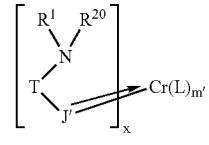

VI (h)

wherein $R^1$, $R^{20}$, L, J and T are described above; x is 1 or 2; and m' is 1, 2, 3, 4, or 5. J' is defined the same as J is defined above, provided that J' includes 2 atoms bonded to the Cr, one of the which is in the ring position adjacent to the atom bonded to T, which is bonded to Cr through a dative bond, and the other of which is bonded to the Cr through a covalent bond. The more specific embodiments of the ligands (e.g., formulas I and II) may replace the coordinated ligands drawn in formulae VI. Numerous other coordination modes are possible, for example the ligands may bind to two chromium metal centers in a bridging fashion (see for example Cotton and Walton, *Multiple Bonds Between Metal Atoms* 1993, Oxford University Press). Some studies (for example, Rensburg et al., *Organometallics* 23, pp 1207-1222 (2004)) suggest that the ligand environment around Cr may be different at different points in the catalytic cycle. Hemilabile ligands, which can change their binding mode to the metal, may be useful in this regard.

In some embodiments, the ligand will be mixed with a suitable metal precursor prior to or simultaneous with allowing the mixture to be contacted to the reactants. When the ligand is mixed with the metal precursor, a metal-ligand complex may be formed. In connection with the metal-ligand complex and depending on the ligand or ligands chosen, the metal-ligand complex may take the form of dimers, trimers or higher orders thereof or there may be two or more metal atoms that are bridged by one or more ligands. Furthermore, two or more ligands may coordinate with a single metal atom. The exact nature of the metal-ligand complex(es) formed depends on the chemistry of the ligand and the method of combining the metal precursor and ligand, such that a distribution of metal-ligand complexes may form with the number of ligands bound to the metal being greater than, equal to or less than the number of equivalents of ligands added relative to an equivalent of metal precursor.

In one embodiment, depicted below, the metal complex is characterized by the following general formula:

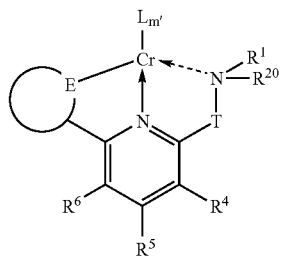

wherein $R^1$, $R^4$, $R^5$, $R^6$, $R^{20}$, T, L and m' are as described above; and E is a carbon atom that is part of an optionally substituted aryl or heteroaryl ring. In one aspect, the aryl or heteroaryl ring may be polycyclic.

Listed below are some examples of Cr-Ligand complex embodiments

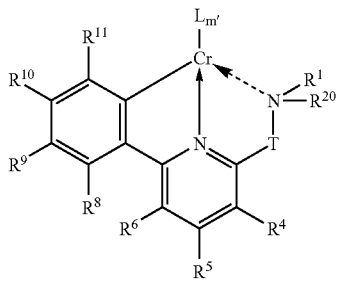

-continued

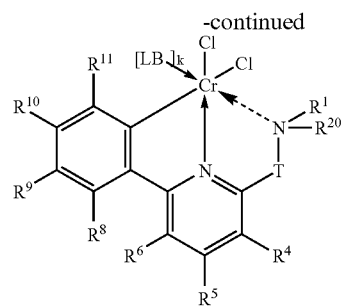

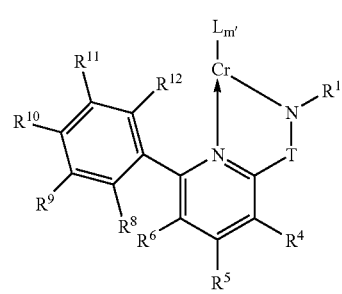

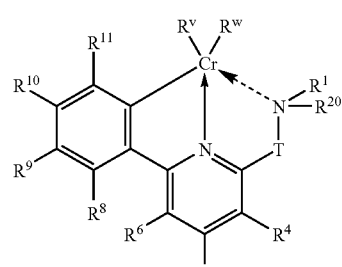

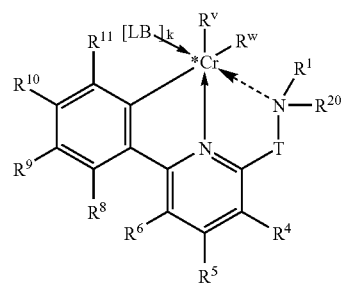

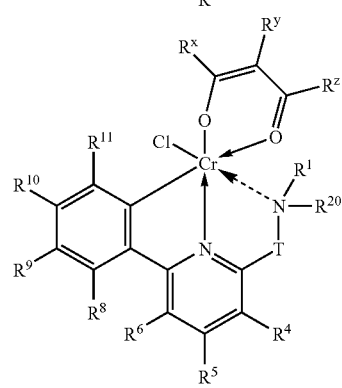

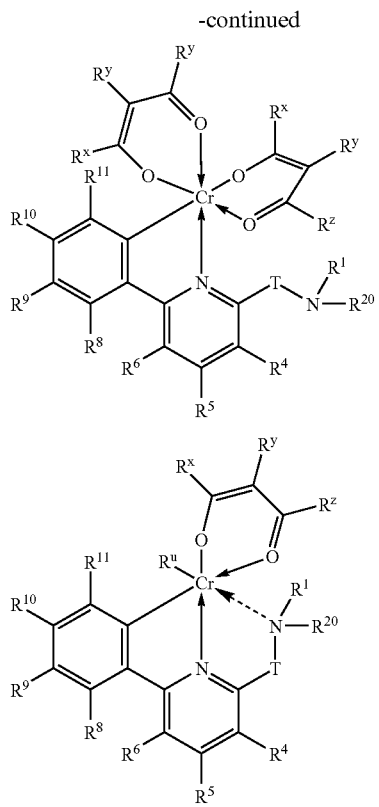

wherein $R^1$, $R^2$, $R^3$, $R^4$, $R^5$, $R^6$, $R^{20}$, T are as defined previously;

$R^8$, $R^9$, $R^{10}$, $R^{11}$, and $R^{12}$ are independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, and optionally two or more $R^8$ $R^9$, $R^{10}$, $R^{11}$ and $R^{12}$ groups may be joined to form one or more optionally substituted ring systems;

$R^u$, $R^v$, $R^w$, $R^x$, $R^y$ and $R^z$ are optionally substituted alkyl, heteroalkyl, aryl, heteroaryl;

L and m' are as defined above;

a dashed arrow indicates that the dative bond is an optional bond which may or may not be present; and LB is a Lewis base and k=0 or 1.

Some specific embodiments of Cr-Ligand complexes are shown below

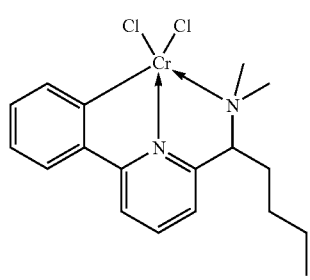

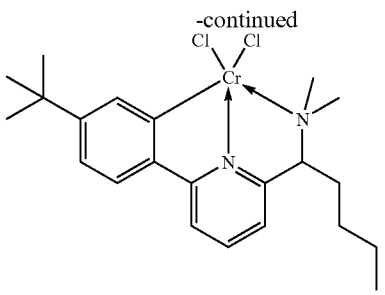

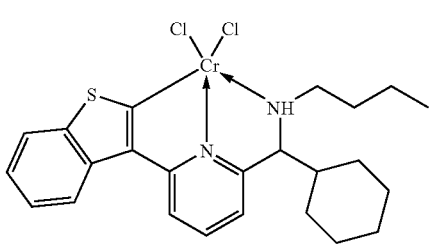

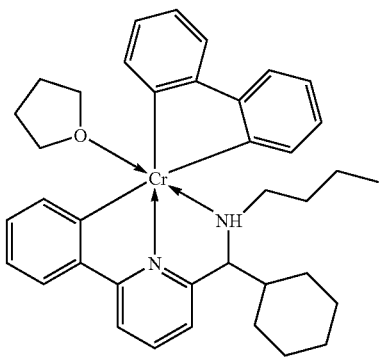

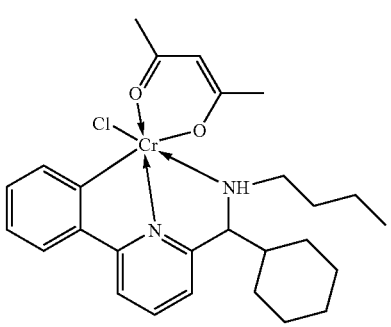

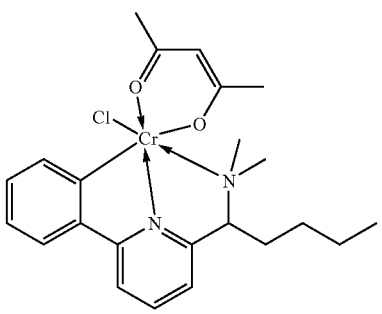

-continued

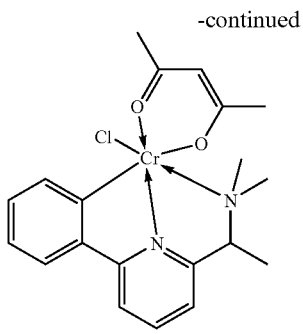

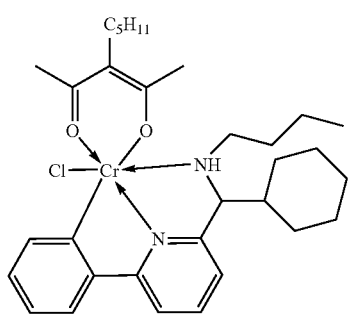

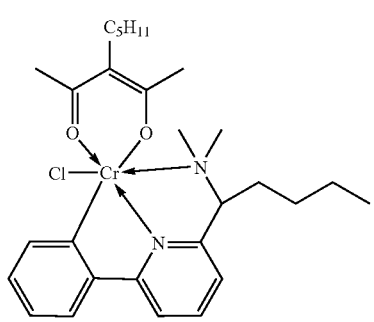

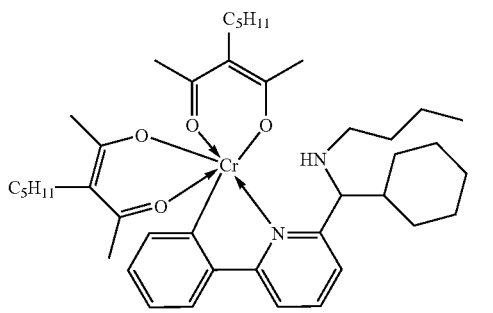

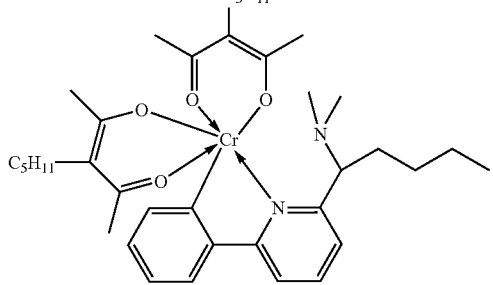

-continued

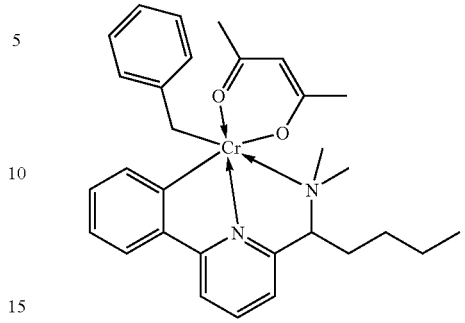

In addition, the catalyst systems of this invention may be combined with other catalysts in a single reactor and/or employed in a series of reactors (parallel or serial).

The ligands-metal-precursors combinations and the metal ligand complexes, described above, are optionally activated in various ways to yield compositions active for selective ethylene oligomerization. For the purposes of this patent specification and appended claims, the terms "cocatalyst" and "activator" are used herein interchangeably and are defined to be any compound which can activate any one of the ligands-metal-precursor-combinations and the metal ligand complexes, described above by converting the combination, complex, or composition into a catalytically active species. Non-limiting activators, for example, include alumoxanes, aluminum alkyls, other metal or main group alkyl or aryl compounds, ionizing activators, which may be neutral or ionic, Lewis acids, reducing agents, oxidizing agents, and combinations thereof.

In one embodiment, alumoxane activators are utilized as an activator in the compositions useful in the invention. Alumoxanes are generally oligomeric compounds containing —Al(R*)—O— sub-units, where R* is an alkyl group. Examples of alumoxanes include methylalumoxane (MAO), ethylalumoxane, isobutylalumoxane, and modified methylalumoxanes (MMAO), which include alkyl groups other than methyl such as ethyl, isobutyl, and n-octyl, such as MMAO-3A, PMAO-IP (referring to polymethylalumoxane, improved process, manufactured by Akzo-Nobel and meaning an MAO prepared from a non-hydrolytic process). Alkylalumoxanes and modified alkylalumoxanes are suitable as catalyst activators, particularly when the abstractable ligand of the catalyst is a halide, alkoxide or amide. Mixtures of different alumoxanes and modified alumoxanes may also be used.

The activator compounds comprising Lewis-acid activators and in particular alumoxanes are specifically characterized by the following general formulae:

$$(R^a—Al—O)_p$$

$$R^b(R^c—Al—O)_p—AlR^e_2$$

where $R^a$, $R^b$, $R^c$ and $R^e$ are, independently a $C_1$-$C_{30}$ alkyl radical, for example, methyl, ethyl, propyl, butyl, pentyl, hexyl, heptyl, octyl, nonyl, decyl, and "p" is an integer from 1 to about 50. Most specifically, $R^a$, $R^b$, $R^c$ and $R^d$ are each methyl and "p" is a least 4. When an alkyl aluminum halide or alkoxide is employed in the preparation of the alumoxane, one or more $R^a$, $R^b$, $R^c$ or $R^e$ are groups may be halide or alkoxide.

It is recognized that alumoxane is not a discrete material. An alumoxane is generally a mixture of both the linear and cyclic compounds. A typical alumoxane will contain free trisubstituted or trialkyl aluminum, bound trisubstituted or trialkyl aluminum, and alumoxane molecules of varying degree of oligomerization. Those methylalumoxanes most preferred contain lower levels of trimethylaluminum. Lower levels of trimethylaluminum can be achieved by reaction of the trimethylaluminum with a Lewis base or by vacuum distillation of the trimethylaluminum or by any other means known in the art.

For further descriptions, see U.S. Pat. Nos. 4,665,208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP0561476A1, EP0279586B1, EP0516476A1, EP0594218A1 and WO94/10180.

When the activator is an alumoxane (modified or unmodified), some embodiments select the maximum amount of activator at a 5000-fold molar excess Al/Cr over the catalyst precursor. The minimum preferred activator-to-catalyst-precursor is a 1:1 molar ratio. More specifically, the Al/Cr ratio is from 1000:1 to 100:1.

Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage. There are a variety of methods for preparing alumoxane and modified alumoxanes, non-limiting examples of which are described in U.S. Pat. Nos. 4,665,208, 4,952, 540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP0561476A1, EP0279586B1, EP0594218A1 and EP0586665B1, and PCT publications WO94/10180 and WO99/15534, all of which are herein fully incorporated by reference. It may be preferable to use a visually clear methylalumoxane. A cloudy or gelled alumoxane can be filtered to produce a clear solution or clear alumoxane can be decanted from the cloudy solution. Another alumoxane is a modified methyl alumoxane (MMAO) cocatalyst type 3A (commercially available from Akzo Chemicals, Inc. under the trade name Modified Methylalumoxane type 3A, covered under patent number U.S. Pat. No. 5,041,584).

Aluminum alkyl or organoaluminum compounds which may be utilized as activators (or scavengers) include trimethylaluminum, triethylaluminum, triisobutylaluminum, tri-n-hexylaluminum, tri-n-octylaluminum, diisobutylaluminum hydride, ethylaluminum dichloride, diethylaluminum chloride, diethylaluminum ethoxide and the like.

Ionizing Activators

In some embodiments, the activator includes compounds that may abstract a ligand making the metal complex cationic and providing a charge-balancing non-coordinating or weakly coordinating anion. The term "non-coordinating anion" (NCA) means an anion which either does not coordinate to said cation or which is only weakly coordinated to said cation thereby remaining sufficiently labile to be displaced by a neutral Lewis base.

It is within the scope of this invention to use an ionizing or stoichiometric activator, neutral or ionic, such as tri (n-butyl) ammonium tetrakis (pentafluorophenyl) boron, a tris(perfluorophenyl) boron metalloid precursor or a tris(perfluoronaphthyl) boron metalloid precursor, polyhalogenated heteroborane anions (WO98/43983), boric acid (U.S. Pat. No. 5,942,459) or combination thereof. It is also within the scope of this invention to use neutral or ionic activators alone or in combination with alumoxane or modified alumoxane activators.

Examples of neutral stoichiometric activators include trisubstituted boron, tellurium, aluminum, gallium and indium or mixtures thereof. The three substituent groups are each independently selected from alkyls, alkenyls, halogen, substituted alkyls, aryls, arylhalides, alkoxy and halides. In some embodiments, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). In other embodiments, the three groups are alkyls having 1 to 4 carbon groups, phenyl, naphthyl or mixtures thereof. In further embodiments, the three groups are halogenated, specifically fluorinated, aryl groups. In even further embodiments, the neutral stoichiometric activator is tris(perfluorophenyl) boron or tris(perfluoronaphthyl) boron.

Ionic stoichiometric activator compounds may contain an active proton, or some other cation associated with, but not coordinated to, or only loosely coordinated to, the remaining ion of the ionizing compound. Such compounds and the like are described in European publications EP0570982A1, EP0520732A1, EP0495375A1, EP0500944B1, EP0277003A1 and EP0277004A1, and U.S. Pat. Nos. 5,153, 157, 5,198,401, 5,066,741, 5,206,197, 5,241,025, 5,384,299 and 5,502,124 and U.S. patent application Ser. No. 08/285, 380, filed Aug. 3, 1994, all of which are herein fully incorporated by reference.

Ionic catalysts can be prepared by reacting a Cr compound with some neutral Lewis acids, such as $B(C_6F_6)_3$, which upon reaction with the abstractable ligand (X) of the Cr compound forms an anion, such as $([B(C_6F_5)_3(X)]^-)$, which stabilizes the cationic Cr species generated by the reaction. The catalysts can be prepared with activator components which are ionic compounds or compositions.

In some embodiments, compounds useful as an activator component in the preparation of the ionic catalyst systems used in the process of this invention comprise a cation, which is optionally a Brönsted acid capable of donating a proton, and a compatible non-coordinating anion which is capable of stabilizing the active catalyst species which is formed when the two compounds are combined and said anion will be sufficiently labile to be displaced by olefinic substrates or other neutral Lewis bases such as ethers, nitriles and the like. Two classes of compatible non-coordinating anions useful herein have been disclosed in EP0277003A1 and EP0277004A1 published 1988: anionic coordination complexes comprising a plurality of lipophilic radicals covalently coordinated to and shielding a central charge-bearing metal or metalloid core; and, anions comprising a plurality of boron atoms such as carboranes, metallacarboranes and boranes.

In one preferred embodiment, the stoichiometric activators include a cation and an anion component, and may be represented by the following formula:

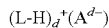

where L is a neutral Lewis base; H is hydrogen; $(L-H)_d^+$ is a Brönsted acid; $A^{d-}$ is a non-coordinating anion having the charge d–; and d is an integer from 1 to 3.

The cation component, $(L-H)_d^+$ may include Brönsted acids such as protons or protonated Lewis bases or reducible Lewis acids capable of protonating or abstracting a moiety, such as an alkyl or aryl, from the bulky ligand chromium catalyst precursor, resulting in a cationic transition metal species.

The activating cation $(L-H)_d^+$ may be a Brönsted acid, capable of donating a proton to the transition metal catalytic precursor resulting in a transition metal cation, including ammoniums, oxoniums, phosphoniums, silyliums, and mixtures thereof, specifically ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers such as dimethyl ether diethyl ether, tetrahydrofuran and dioxane, sulfoniums from thioethers, such as diethyl thioethers and tetrahydrothiophene, and mixtures thereof. The activating cation $(L-H)_d^+$ may also be a moiety such as silver, tropylium, carbeniums, ferroceniums and mixtures, specifically carboniums and ferroceniums. In one embodiment $(L-H)_d^+$ can be triphenyl carbonium.

The anion component $A^{d-}$ includes those having the formula $[M^{k+}Q_n]^{d-}$ wherein k is an integer from 1 to 3; n is an integer from 2-6; n–k=d; M is an element selected from Group 13 of the Periodic Table of the Elements, specifically boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Specifically, each Q is a fluorinated hydrocarbyl group having 1 to 20 carbon atoms, more specifically each Q is a fluorinated aryl group, and most specifically each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as an activating cocatalyst in the preparation of the improved catalysts of this invention are tri-substituted ammonium salts such as:

trimethylammonium tetraphenylborate, triethylammonium tetraphenylborate, tripropylammonium tetraphenylborate, tri(n-butyl)ammonium tetraphenylborate, tri(t-butyl) ammonium tetraphenylborate, N,N-dimethylanilinium tetraphenylborate, N,N-diethylanilinium tetraphenylborate, N,N-dimethyl-(2,4,6-trimethylanilinium) tetraphenylborate, tropillium tetraphenylborate, triphenylcarbenium tetraphenylborate, triphenylphosphonium tetraphenylborate, triethylsilylium tetraphenylborate, benzene(diazonium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, trimethylammonium tetrakis-(2,3,4,6-tetrafluorophenyl) borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl (t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl) borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, trimethylammonium tetrakis (perfluoronaphthyl)borate, triethylammonium tetrakis (perfluoronaphthyl)borate, tripropylammonium tetrakis (perfluoronaphthyl)borate, tri(n-butyl)ammonium tetrakis (perfluoronaphthyl)borate, tri(t-butyl)ammonium tetrakis (perfluoronaphthyl)borate, N,N-dimethylanilinium tetrakis (perfluoronaphthyl)borate, N,N-diethylanilinium tetrakis (perfluoronaphthyl)borate, N,N-dimethyl-(2,4,6-trimethylanilinium) tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis (perfluoronaphthyl)borate, trimethylammonium tetrakis (perfluorobiphenyl)borate, triethylammonium tetrakis (perfluorobiphenyl)borate, tripropylammonium tetrakis (perfluorobiphenyl)borate, tri(n-butyl)ammonium tetrakis (perfluorobiphenyl)borate, tri(t-butyl)ammonium tetrakis (perfluorobiphenyl)borate, N,N-dimethylanilinium tetrakis (perfluorobiphenyl)borate, N,N-diethylanilinium tetrakis (perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis (perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl)ammonium tetrakis(3,5-bis (trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis (trifluoromethyl)phenyl)borate, tropillium tetrakis(3,5-bis (trifluoromethyl)phenyl)borate, triphenylcarbenium tetrakis (3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl) phenyl)borate, benzene(diazonium) tetrakis(3,5-bis(trifluoromethyl)phenyl)borate, and dialkyl ammonium salts such as: di-(i-propyl)ammonium tetrakis(pentafluorophenyl)borate, and dicyclohexylammonium tetrakis(pentafluorophenyl)borate; and additional tri-substituted phosphonium salts such as tri(o-tolyl)phosphonium tetrakis(pentafluorophenyl) borate, and tri(2,6-dimethylphenyl)phosphonium tetrakis (pentafluorophenyl)borate.

Most specifically, the ionic stoichiometric activator (L-H)$_d^+$ (A$^{d-}$) is N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, or triphenylcarbenium tetra(perfluorophenyl)borate.

Other examples of preferred ionizing activators include, HNMe(C$_{18}$H$_{37}$)$_2^+$B(C$_6$F$_5$)$_4^-$; HNPh(C$_{18}$H$_{37}$)$_2^+$B(C$_6$F$_5$)$_4^-$ and ((4-n-Bu-C$_6$H$_4$)NH(n-hexyl)$_2$)$^+$B(C$_6$F$_5$)$_4^-$ and ((4-n-Bu-C$_6$H$_4$)NH(n-decyl)$_2$)$^+$B(C$_6$F$_5$)$_4^-$. Specific preferred (L*-H)$^+$ cations are N,N-dialkylanilinium cations, such as HNMe$_2$Ph$^+$, substituted N,N-dialkylanilinium cations, such as (4-n-Bu-C$_6$H$_4$)NH(n-C$_6$H$_{13}$)$_2^+$ and (4-n-Bu-C$_6$H$_4$)NH(n-C$_{10}$H$_{21}$)$_2^+$ and HNMe(C$_{18}$H$_{37}$)$_2^+$. Specific examples of anions are tetrakis(3,5-bis(trifluoromethyl)phenyl)borate and tetrakis(pentafluorophenyl)borate.

In one embodiment, activation methods using ionizing ionic compounds not containing an active proton but capable of producing an active oligomerization catalyst are also contemplated. Such methods are described in relation to metallocene catalyst compounds in EP0426637A1, EP0573403A1 and U.S. Pat. No. 5,387,568, which are all herein incorporated by reference.

The process can also employ cocatalyst compounds or activator compounds that are initially neutral Lewis acids but form a cationic metal complex and a noncoordinating anion, or a zwitterionic complex upon reaction with the compounds of this invention. For example, tris(pentafluorophenyl) boron or aluminum may act to abstract a hydrocarbyl or hydride ligand to yield a cationic metal complex and stabilizing noncoordinating anion.

In some embodiments, ionizing activators may be employed as described in Köhn et al. (*J. Organomet. Chem.*, 683, pp 200-208, (2003)) to, for example, improve solubility.

In another embodiment, the aforementioned cocatalyst compounds can also react with the compounds to produce a neutral, uncharged catalyst capable of selective ethylene oligomerization. For example, Lewis acidic reagents such as, for example, alkyl or aryl aluminum or boron compounds, can abstract a Lewis basic ligand such as, for example, THF or Et$_2$O, from a compound yielding a coordinatively unsaturated catalyst capable of selective ethylene oligomerization.

When the cations of noncoordinating anion precursors are Brönsted acids such as protons or protonated Lewis bases (excluding water), or reducible Lewis acids such as ferrocenium or silver cations, or alkali or alkaline earth metal cations such as those of sodium, magnesium or lithium, the activator-to-catalyst-precursor molar ratio may be any ratio, however, useful ratios can be from 1000:1 to 1:1.

Combinations of two or more activators may also be used in the practice of this invention.

Another suitable ion forming, activating cocatalyst comprises a salt of a cationic oxidizing agent and a noncoordinating, compatible anion characterized by the general formula:

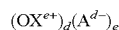

where OX$^{e+}$ is a cationic oxidizing agent having a charge of e+; e is an integer from 1 to 3; d is an integer from 1 to 3, and A$^{d-}$ is as previously defined. Examples of cationic oxidizing agents include: ferrocenium, hydrocarbyl-substituted ferrocenium, Ag$^+$, or Pb$^{+2}$. Preferred embodiments of A$^{d-}$ are those anions previously defined with respect to the Brönsted acid containing activators, especially tetrakis(pentafluorophenyl)borate.

Group 13 Reagents, Divalent Metal Reagents, and Alkali Metal Reagents

Other general activators or compounds useful in an oligomerization reaction may be used. These compounds may be activators in some contexts, but may also serve other functions in the reaction system, such as alkylating a metal center or scavenging impurities. These compounds are within the general definition of "activator," but are not considered herein to be ion-forming activators. These compounds include a group 13 reagent that may be characterized by the formula G$^{13}$R$^{50}_{3-p}$D$_p$ where G$^{13}$ is selected from the group consisting of B, Al, Ga, In, and combinations thereof, p is 0, 1 or 2, each R$^{50}$ is independently selected from the group consisting of hydrogen, halogen, and optionally substituted alkyl, alkenyl, alkynyl, heteroalkyl, heteroalkenyl, heteroalkynyl, aryl, heteroaryl, and combinations thereof, and each D is independently selected from the group consisting of halogen, hydrogen, alkoxy, aryloxy, amino, mercapto, alkylthio, arylthio, phosphino and combinations thereof.

In other embodiments, the group 13 activator is an oligomeric or polymeric alumoxane compound, such as methylalumoxane and the known modifications thereof. See, for example, Barron, *"Alkylalumoxanes, Synthesis, Structure and Reactivity"*, pp. 33-67 in *Metallocene-Based Polyolefins: Preparation, Properties and Technology*, J. Schiers and W. Kaminsky (eds.), Wiley Series in Polymer Science, John Wiley & Sons Ltd., Chichester, England, 2000, and references cited therein.

In other embodiments, a divalent metal reagent may be used that is characterized by the general formula M'R$^{50}_{2-p'}$D$_{p'}$ and p' is 0 or 1 in this embodiment and R$^{50}$ and D are as defined above. M' is the metal and is selected from the group consisting of Mg, Ca, Sr, Ba, Zn, Cd, Cu and combinations thereof.

In still other embodiments, an alkali metal reagent may be used that is defined by the general formula M'$^{IV}$R$^{50}$ and in this embodiment R$^{50}$ is as defined above, and M'$^{IV}$ is the alkali metal and is selected from the group consisting of Li, Na, K, Rb, Cs and combinations thereof. Additionally, hydrogen and/or silanes may be used in the catalytic composition or added to the polymerization system. Silanes may be characterized by the formula SiR$^{50}_{4-q}$D$_q$ where R$^{50}$ is defined as above, q is 1, 2, 3 or 4 and D is as defined above, with the proviso that at least one D is hydrogen.

Non-limiting examples of Group 13 reagents, divalent metal reagents, and alkali metal reagents useful as activators for the catalyst compounds described above include methyl lithium, butyl lithium, phenyl lithium, dihexylmercury, butyl-magnesium, diethylcadmium, benzylpotassium, diethyl zinc, tri-n-butyl aluminum, diisobutyl ethylboron, diethylcadmium, di-n-butyl zinc and tri-n-amyl boron, and, in particular, the aluminum alkyls, such as trihexyl-aluminum, triethylaluminum, trimethylaluminum, and triisobutyl aluminum, diisobutyl aluminum bromide, diethylaluminum chloride, ethylaluminum dichloride, isobutyl boron dichloride, methyl magnesium chloride, ethyl beryllium chloride, ethyl calcium bromide, diisobutyl aluminum hydride, methyl cadmium hydride, diethyl boron hydride, hexylberyllium hydride, dipropylboron hydride, octylmagnesium hydride, butyl zinc hydride, dichloroboron hydride, di-bromo-aluminum hydride and bromocadmium hydride. Other Group 13 reagents, divalent metal reagents, and alkali metal reagents useful as activators for the catalyst compounds described above are known to those in the art, and a more complete discussion of these compounds may be found in U.S. Pat. Nos. 3,221,002 and 5,093,415, which are herein fully incorporated by reference.

Other activators include those described in PCT publication WO98/07515 such as tris(2,2',2"-nonafluorobiphenyl) fluoroaluminate, which publication is fully incorporated herein by reference. Combinations of activators are also contemplated by the invention, for example, alumoxanes and ionizing activators in combinations, see for example, EP0573120B1, PCT publications WO94/07928 and WO95/14044 and U.S. Pat. Nos. 5,153,157 and 5,453,410, all of which are herein fully incorporated by reference.

Other suitable activators are disclosed in WO98/09996, incorporated herein by reference, which describes activating bulky ligand metallocene catalyst compounds with perchlorates, periodates and iodates including their hydrates. WO98/30602 and WO98/30603, incorporated by reference, describe the use of lithium (2,2'-bisphenyl-ditrimethylsilicate).4THF as an activator for a bulky ligand metallocene catalyst compound. WO99/18135, incorporated herein by reference, describes the use of organo-boron-aluminum activators. EP0781299B1 describes using a silylium salt in combination with a non-coordinating compatible anion. Also, methods of activation such as using radiation (see EP0615981B1 herein incorporated by reference), electro-chemical oxidation, and the like are also contemplated as activating methods for the purposes of rendering the chromium complexes or compositions active for the selective oligomerization of olefins. Other activators or methods are described in for example, U.S. Pat. Nos. 5,849,852, 5,859,653 and 5,869,723 and WO98/32775, WO99/42467 (dioctadecylmethylammonium-bis(tris(pentafluorophenyl)borane) benzimidazolide), which are herein incorporated by reference.

Additional optional activators include metal salts of non-coordinating or weakly coordinating anions, for example where the metal is selected from Li, Na, K, Ag, Ti, Zn, Mg, Cs, and Ba.

It is within the scope of this invention that metal-ligand complexes and or ligand-metal-precursor-combinations can be combined with one or more activators or activation methods described above. For example, a combination of activators has been described in U.S. Pat. Nos. 5,153,157 and 5,453,410, EP0573120B1, and PCT publications WO94/07928 and WO95/14044. These documents all discuss the use of an alumoxane in combination with an ionizing activator.

In one embodiment, the molar ratio of metal (from the metal-ligand-complex or the ligand-metal-precursor-combination) to activator (specifically Cr:activator, specifically Cr:Al or Cr:B) can range from 1:1 to 1:5000. In another embodiment, the molar ratio of metal to activator employed can range from 1:1 to 1:500. In another embodiment, the molar ratio of metal to activator employed can range from 1:1 to 1:50. In another embodiment, the molar ratio of chromium to activator employed can range from 1:1 to 1:500. In another embodiment, the molar ratio of chromium to activator employed can range from 1:1 to 1:50.

In embodiments where more than one activator is used, the order in which the activators are combined with the metal-ligand-complex or the ligand-metal-precursor-combination may be varied.

In some embodiments, the process of the invention relates to the oligomerization, and more specifically the trimerization and/or tetramerization of ethylene. The ligand-metal-precursor-combinations, metal-ligand-complexes, and/or catalyst systems of this invention are particularly effective at oligomerizing and specifically trimerizing and/or tetramerizing ethylene to form 1-hexene and/or 1-octene.

In other embodiments, this invention relates to the oligomerization and more specifically the trimerization and/or tetramerization of α-olefins or co-oligomerization of ethylene with α-olefins. The trimerization of α-olefins is described in Köhn et al., Angew. Chem. Int. Ed., 39 (23), pp 4337-4339 (2000).

Very generally, oligomerization can be carried out in the Ziegler-Natta or Kaminsky-Sinn methodology, including temperatures from −100° C. to 300° C. and pressures from atmospheric to 3000 atmospheres (303,900 kPa). Suspension, solution, slurry, gas phase, or high-pressure oligomerization processes may be employed with the catalysts and compounds of this invention. Such processes can be run in a batch, semi-batch, or continuous mode. Examples of such processes are well known in the art.

Suitable solvents for oligomerization are non-coordinating, inert liquids. Examples include straight and branched-chain hydrocarbons such as isobutane, butane, pentane, isopentane, hexane, isohexane, heptane, octane, dodecane, and mixtures thereof; cyclic and alicyclic hydrocarbons such as cyclohexane, cycloheptane, methylcyclohexane, methylcycloheptane, and mixtures thereof; perhalogenated hydrocarbons such as perfluorinated $C_{4-10}$ alkanes, chlorobenzene, and aromatic and alkylsubstituted aromatic compounds such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, and 1-decene. Mixtures of the foregoing are also suitable.

Other additives that are useful in an oligomerization reaction may be employed, such as scavengers, promoters, modifiers, reducing agents, oxidizing agents, dihydrogen, aluminum alkyls, or silanes. For example, Jolly et al. (Organometallics, 16, pp 1511-1513 (1997)) has reported the use of magnesium as a reducing agent for Cr compounds that were synthesized as models for intermediates in selective ethylene oligomerization reactions.

In some useful embodiments, the activator (such as methylalumoxane or modified methylalumoxane-3A) is combined with the metal-ligand-complex or the ligand-metal-precursor-combination immediately prior to introduction into the reactor. Such mixing may be achieved by mixing in a separate tank then swift injection into the reactor, mixing in-line just prior to injection into the reactor, or the like. It has been observed that in some instances, a short activation time is very useful. Likewise in-situ activation, where the catalyst system components are injected separately into the reactor, with or without monomer, and allowed to combine within the reactor directly is also useful in the practice of this invention. In some embodiments, the catalyst system components are allowed to contact each other for 30 minutes or less, prior to contact with monomer, alternately for 5 minutes or less, alternately for 3 minutes or less, alternately for 1 minute or less.

In another embodiment, the present invention relates to methods of producing oligomers of olefins, catalysts, ligands used to prepare the catalyst and catalyst compositions as described in the following paragraphs In a first embodiment, the present invention pertains to a method of producing oligomers of olefins, comprising reacting an olefin with a catalyst under oligomerization conditions, wherein the oligomerization reaction has a selectivity of at least 70 mole percent for oligomer, and wherein the catalyst is formed from the combination of:

(1) a ligand characterized by the following general formula:

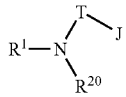

wherein $R^1$ and $R^{20}$ are each independently selected from the group consisting of hydrogen and optionally substituted hydrocarbyl, heteroatom containing hydrocarbyl and silyl, and where $R^1$ and $R^{20}$ may optionally be joined in a ring structure having from 3-50 non-hydrogen atoms; provided that $R^1$ or $R^{20}$ do not equal T-J, where T-J is as given by the general formula above and defined below;

T is a bridging group of the general formula —(T'$R^2R^3$)—, where T' is selected from the group consisting of carbon and silicon, $R^2$ and $R^3$ are independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, provided that two or more $R^2$ and/or $R^3$ groups may be joined together to form one or more optionally substituted ring systems having from 3-50 non-hydrogen atoms;

J is an optionally substituted six-membered heterocycle, containing at least one nitrogen atom as part of the ring;

(2) a metal precursor compound characterized by the general formula Cr(L)$_n$ where each L is independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, wherein two or more L groups may be combined in a ring structure having from 3 to 50 non-hydrogen atoms; n is 1, 2, 3, 4, 5, or 6; and (3) optionally, one or more activators.

In a second embodiment of the method, the ligand is characterized by the following general formula:

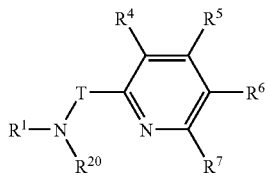

wherein $R^1$, $R^{20}$, and T are as described above; and $R^4$, $R^5$, $R^6$ and $R^7$ are independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, and optionally two or more $R^1$, $R^{20}$, $R^2$, $R^3$, $R^4$, $R^5$, $R^6$ and $R^7$ groups may be joined to form one or more optionally substituted ring systems.

In a third embodiment of the method, $R^1$ and $R^{20}$ are each independently selected from hydrogen and optionally substituted alkyl.

In a fourth embodiment of the method, $R^1$ and $R^{20}$ are each independently a ring having from 4-8 atoms in the ring generally selected from the group consisting of substituted cycloalkyl, heterocycloalkyl, aryl, and heteroaryl.

In a fifth embodiment of the method $R^1$ and $R^{20}$ are each independently selected from hydrogen and optionally substituted alkyl.

In a sixth embodiment of the method, wherein $R^1$ and $R^{20}$ are each independently a ring having from 4-8 atoms in the ring generally selected from the group consisting of substituted cycloalkyl, heterocycloalkyl, aryl, and heteroaryl.

In a seventh embodiment of the method, $R^1$ is hydrogen and $R^{20}$ is selected from the group consisting of methyl, ethyl, propyl, butyl, pentyl, hexyl, octyl, decyl, dodecyl, benzyl, and —CH$_2$CH$_2$Ph groups.

In an eighth embodiment of the method, $R^1$ and $R^{20}$ are each independently selected from the group consisting of methyl, ethyl, propyl, butyl, pentyl, hexyl, octyl, decyl, dodecyl, benzyl and —CH$_2$CH$_2$Ph groups.

In an ninth embodiment of the method, $R^7$ is selected from the group consisting of optionally substituted aryl and heteroaryl.

In a tenth embodiment of the method, $R^5$ is selected from the group consisting of —CF$_3$, H, F, Cl, —N(Me)$_2$ and —OR, wherein R is an optionally substituted alkyl group, an optionally substituted benzyl group or an optionally substituted aryl group.

In a eleventh embodiment of the method, $R^3$ is selected from the group consisting of hydrogen and optionally substituted alkyl, heteroalkyl, cycloalkyl, heterocycloalkyl, silyl and combinations thereof.

In a twelfth embodiment of the method, the ligand is selected from the group consisting of ligands A1 through A75 depicted in FIGS. 1 through 7.

In thirteenth through twentyone embodiments of the method, the ligand is

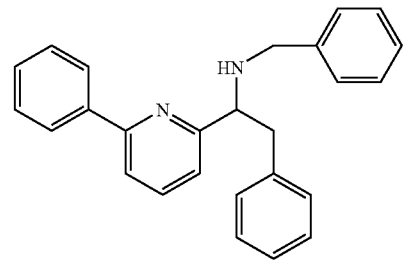

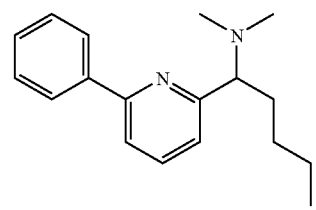

-continued

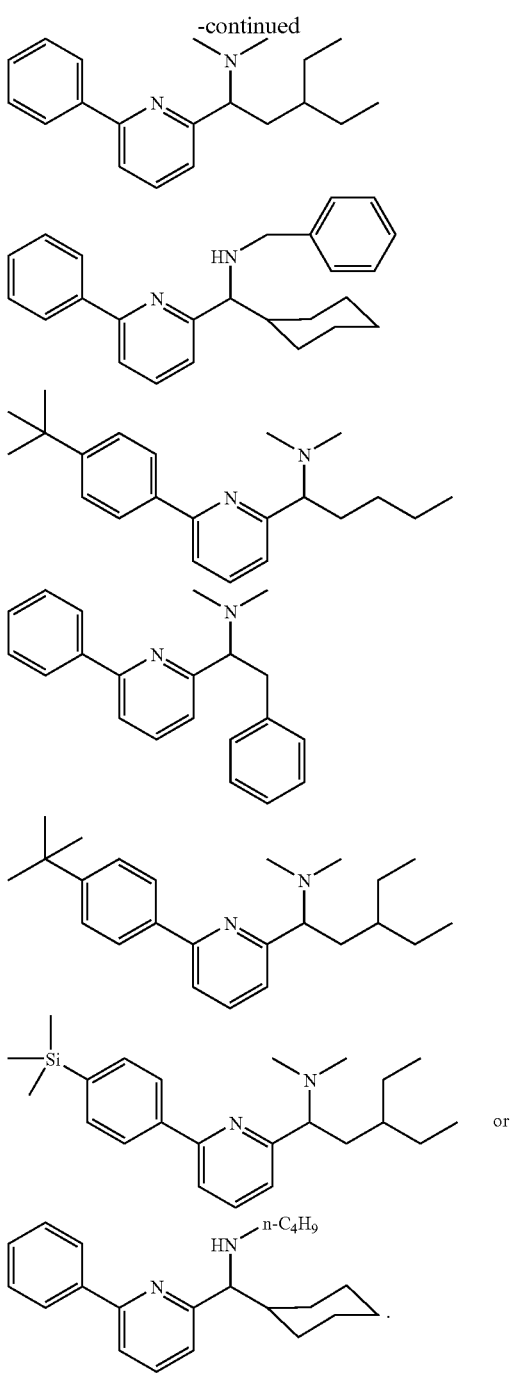

or

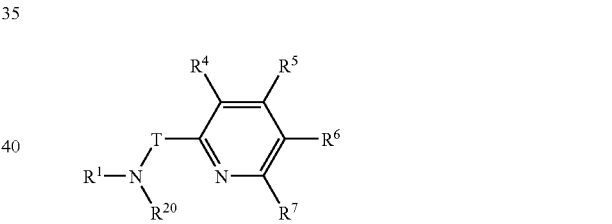

In a twenty second embodiment that can be used with any of the first twenty one embodiments, the activator is an alumoxane, which may optionally be used in any combination with group 13 reagents, divalent metal reagents, and/or alkali metal reagents.

In a twenty third embodiment that can be used with any of the first twenty one embodiments, the activator is a neutral or ionic stoichiometric activator, which may optionally be used in any combination with group 13 reagents, divalent metal reagents, and/or alkali metal reagents.

In a twenty fourth embodiment that can be used with any of the first twenty one embodiments, the activator is selected from the group consisting of modified methylaluminoxane (MMAO), methylaluminoxane (MAO), trimethylaluminum (TMA), triisobutyl aluminum (TIBA), diisobutylaluminumhydride (DIBAL), polymethylaluminoxane-IP (PMAO), triphenylcarbonium tetrakis(perfluorophenyl)borate, N,N-dimethyl-anilinium tetrakis(perfluorophenyl)borate N,N-di (n-decyl)4-n-butyl-anilinium tetrakis(perfluorophenyl)borate, and mixtures thereof.

In a twenty fifth embodiment that can be used with any of the first twenty one embodiments, the metal precursor is selected from the group consisting of $(THF)_3CrMeCl_2$, $(THF)_3CrCl_3$, $(Mes)_3Cr(THF)$, $[\{TFA\}_2Cr(OEt_2)]_2$, $(THF)_3CrPh_3$, $(THF)_3Cr(\eta^2\text{-}2,2'\text{-Biphenyl})Br$ and mixtures thereof.

In a twenty sixth embodiment of the method, the olefin is a $C_2$ to $C_{12}$ olefin.

In a twenty seventh embodiment of the method, the olefin is a $C_2$ to $C_8$ olefin.

In a twenty eighth embodiment of the method, the olefin is ethylene.

In a twenty ninth embodiment of the method, the process produces a trimer or a tetramer of the olefin.

In a thirtieth embodiment of the method, the process produces 1-hexene.

In a thirty first embodiment of the method, the process produces 1-octene.

In a thirty second embodiment of the method, the process produces a mixture of 1-hexene and 1-octene.

In a thirty third embodiment of the method, the reaction occurs in a hydrocarbon solvent.

In a thirty fourth embodiment of the method, the reaction occurs in an aliphatic hydrocarbon solvent In a thirty fifth embodiment, the invention pertains to a composition comprising:

(1) a ligand characterized by the following general formula:

wherein $R^1$ and $R^{20}$ are each independently selected from the group consisting of hydrogen and optionally substituted alkyl;

T is a bridging group of the general formula $-(T'R^2R^3)-$, where T' is selected from the group consisting of carbon and silicon, $R^2$ and $R^3$ are independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, provided that two or more $R^2$ and/or $R^3$ groups may be joined together to form one or more optionally substituted ring systems having from 3-50 non-hydrogen atoms;

$R^4$, $R^5$, $R^6$ and $R^7$ are independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, and optionally two or more $R^1$, $R^{20}$, $R^2$, $R^3$, $R^4$, $R^5$, $R^6$ and $R^7$ groups may be joined to form one or more optionally substituted ring systems (2) a metal precursor compound characterized by the general formula $Cr(L)_n$ where each L is independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, wherein two or more L groups may be combined in a ring structure having from 3 to 50 non-hydrogen atoms; n is 1, 2, 3, 4, 5, or 6; and (3) optionally, one or more activators.

In a thirty sixth embodiment of the aforementioned composition, $R^1$ is hydrogen and $R^{20}$ is selected from the group consisting of methyl, ethyl, propyl, butyl, pentyl, hexyl, octyl, decyl, dodecyl, benzyl, and —$CH_2CH_2Ph$ groups.

In a thirty seventh embodiment of the thirty fifth embodiment, $R^1$ and $R^{20}$ are each independently selected from the group consisting of methyl, ethyl, propyl, butyl, pentyl, hexyl, octyl, decyl, dodecyl, benzyl and —$CH_2CH_2Ph$ groups.

In a thirty eighth embodiment of the thirty fifth embodiment, $R^7$ is selected from the group consisting of optionally substituted aryl and heteroaryl.

In a thirty ninth embodiment of the thirty fifth embodiment, $R^3$ is selected from the group consisting of hydrogen and optionally substituted alkyl, heteroalkyl, cycloalkyl, heterocycloalkyl, silyl and combinations thereof.

In a fortieth embodiment of the thirty fifth embodiment, $R^5$ is selected from the group consisting of —$CF_3$, H, F, Cl, —$N(Me)_2$ and —OR, wherein R is an optionally substituted alkyl group, an optionally substituted benzyl group or an optionally substituted aryl group.

In a forty first embodiment, the invention pertains to a metal complex characterized by the following general formula:

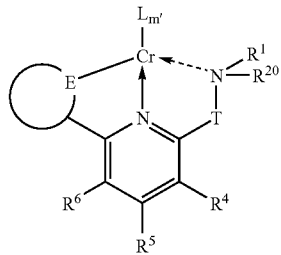

wherein $R^1$ and $R^{20}$ are each independently selected from the group consisting of hydrogen and optionally substituted alkyl heteroalkyl, cycloalkyl, heterocycloalkyl, aryl, heteroaryl, silyl and combinations thereof;

T is a bridging group of the general formula —(T'$R^2R^3$)—, where T' is selected from the group consisting of carbon and silicon, $R^2$ and $R^3$ are independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, provided that two or more $R^2$ and/or $R^3$ groups may be joined together to form one or more optionally substituted ring systems having from 3-50 non-hydrogen atoms;

$R^4$, $R^5$ and $R^6$ are independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, and optionally two or more $R^1$, $R^{20}$, $R^2$, $R^3$, $R^4$, $R^5$ and $R^6$ groups may be joined to form one or more optionally substituted ring systems;

E is a carbon atom that is part of an optionally substituted aryl or heteroaryl ring;

L and m' are defined above; and a dashed arrow indicates that the dative bond is an optional dative bond which may or may not be present.

In a forty second embodiment, $R^1$ is hydrogen and $R^{20}$ is selected from the group consisting of methyl, ethyl, propyl, butyl, pentyl, hexyl, octyl, decyl, dodecyl, benzyl, and —$CH_2CH_2Ph$ groups in the complex of the forty first embodiment.

In a forty third embodiment, $R^1$ and $R^{20}$ are each independently selected from the group consisting of methyl, ethyl, propyl, butyl, pentyl, hexyl, octyl, decyl, dodecyl, benzyl and —$CH_2CH_2Ph$ groups in the forty first embodiment.

In a forty fourth embodiment, the complex is characterized by the following general formula:

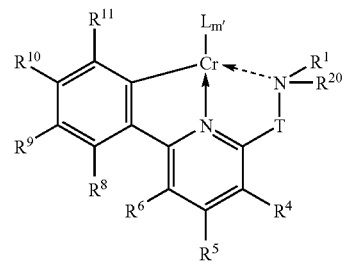

wherein $R^1$ and $R^{20}$ are each independently selected from the group consisting of hydrogen and optionally substituted alkyl heteroalkyl, cycloalkyl, heterocycloalkyl, aryl, heteroaryl, silyl and combinations thereof;

T is a bridging group of the general formula —(T'$R^2R^3$)—, where T' is selected from the group consisting of carbon and silicon, $R^2$ and $R^3$ are independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, and combinations thereof, provided that two or more $R^2$ and/or $R^3$ groups may be joined together to form one or more optionally substituted ring systems having from 3-50 non-hydrogen atoms;

$R^4$, $R^5$, $R^6$, $R^8$, $R^9$, $R^{10}$ and $R^{11}$ are independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, and optionally two or more $R^1$, $R^{20}$, $R^2$, $R^3$, $R^4$, $R^5$, $R^6$, $R^8$, $R^9$, $R^{10}$ and $R^{11}$ groups may be joined to form one or more optionally substituted ring systems;

L and m' are defined above; and a dashed arrow indicates that the dative bond is an optional bond which may or may not be present.

In a forty fifth embodiment, the invention pertains to a method of producing oligomers of olefins, comprising reacting an olefin with a catalyst under oligomerization conditions, wherein said oligomerization reaction has a selectivity of at least 70 mole percent for oligomer, and wherein said catalyst is comprised the metal complexes of either of the forty third or forty fourth embodiment(s), and optionally, an activator.

In a forty sixth embodiment, $R^1$ is hydrogen and $R^{20}$ is selected from the group consisting of methyl, ethyl, propyl, butyl, pentyl, hexyl, octyl, decyl, dodecyl, benzyl, and —$CH_2CH_2Ph$ groups in the forty fifth embodiment.

In a forty seventh embodiment, $R^1$ and $R^{20}$ are each independently selected from the group consisting of methyl, ethyl, propyl, butyl, pentyl, hexyl, octyl, decyl, dodecyl, benzyl and —CH$_2$CH$_2$Ph groups in the forty fifth embodiment.

In a forty eighth embodiment, the olefin is ethylene in the forty fifth embodiment.

In a forty nineth embodiment, the process of the forty fifth embodiment produces a trimer or a tetramer of the olefin.

In a fiftieth embodiment, the process of the forty nineth embodiment produces 1-hexene.

In a fifty first embodiment, the reaction occurs in a hydrocarbon solvent in the forty fifth embodiment.

In a fifty second embodiment, the reaction occurs in an aliphatic hydrocarbon solvent in the forty fifth embodiment.

EXAMPLES

General: All air sensitive procedures were performed under a purified argon or nitrogen atmosphere in a Vacuum Atmospheres or MBraun glove box. All solvents used were anhydrous, de-oxygenated and purified according to known techniques (see for example, D. D. Perrin & W. L. F. Armarego *Purification of Laboratory Chemicals*, 3$^{rd}$ Ed., (Pergamon Press: New York, 1988)). All ligands and metal precursors were prepared according to procedures known to those of skill in the art, e.g., under inert atmosphere conditions, etc. Ethylene oligomerization experiments were carried out in a parallel pressure reactor, described in U.S. Pat. Nos. 6,306,658, 6,455,316 and 6,489,168, and in U.S. application Ser. No. 09/177,170, filed Oct. 22, 1998, WO 00/09255, and a parallel batch reactor with in situ injection capability, as described in WO 04/060550, and U.S. Application No. 2004/0121448, each of which is incorporated herein by reference.

Quantitative analysis of the liquid olefin products was performed using an automated Agilent 6890 Dual Channel Gas Chromatograph fitted with 2 Flame Ionization Detectors. The liquid olefin products were first separated using RT-x1 columns (1.25 m length×0.25 mm thickness×1 μm width; manufactured by Restek and spooled into module by RVM Scientific) and quantified by flame ionization detection by comparison with calibration standards. Cyclooctane was used as an internal standard. Samples were loaded onto the columns from an 8×12 array of 1 mL glass vials using a CTC HTS PAL LC-MS autosampler purchased from LEAPTEC. Polyethylene yields were determined using a Bohdan model BA-100 automated weighing module.

Ligand Synthesis

Example a

Synthesis of Pyridyl-Amine Ligand A29: Example of Method A

Step 1

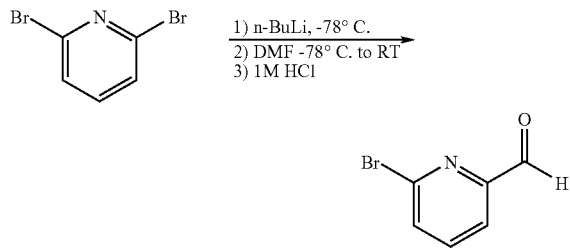

To a solution of 23.7 g (100 mmol) of 2,6-dibromopyridine in 150 mL of anhydrous, degassed THF cooled to −78° C. was added dropwise under N$_2$ a solution of 11.0 mL (110 mmol) of 10.0 M n-BuLi in 150 mL anhydrous, degassed Et$_2$O. After 2 hours at −78° C., 24.2 mL (300 mmol) of anhydrous degassed DMF was added dropwise with rapid stirring. This solution was stirred at −78° C. for 2 hours, and was then allowed to warm to room temperature (RT) overnight. The solution was cooled to −78° C. and 100 mL of 1.0 M aq. HCl was added slowly. The organic phase was separated and the aqueous phase was washed with 3×50 mL Et$_2$O. The organic washes were combined and washed with 3×50 mL H$_2$O and 3×50 mL brine, then dried over Na$_2$SO$_4$. The volatiles were removed in vacuo to provide an orange oil. The oil was triturated with hexanes to give 2-bromo-6-formylpyridine as a pale orange solid that was washed with cold pentanes and dried under vacuum overnight.

Step 2

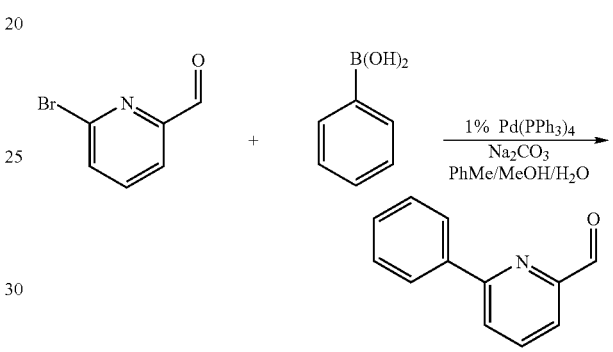

Phenylboronic acid (1.46 g, 12 mmol) and Na$_2$CO$_3$ (2.65 g, 25 mmol) were dissolved in 60 mL of degassed 4:1H$_2$O/MeOH. This solution was added via cannula to a solution of 1.86 g (10 mmol) of 2-bromo-6-formylpyridine and 116 mg (0.10 mmol) of Pd(PPh$_3$)$_4$ in 50 mL of degassed toluene. The biphasic mixture was vigorously stirred and heated at 70° C. under N$_2$ for 4 h. On cooling to RT, the organic phase was separated and the aqueous phase was washed with 3×25 mL of Et$_2$O. The combined organic extracts were washed with 3×25 mL of H$_2$O and 20 mL of brine and dried over Na$_2$SO$_4$. After removing the volatiles in vacuo, the resultant brown oil was chromatographed on silica with hexanes/CH$_2$Cl$_2$. Clean fractions were combined and the volatiles were removed to provide 2-formyl-6-phenylpyridine as a white solid.

Step 3

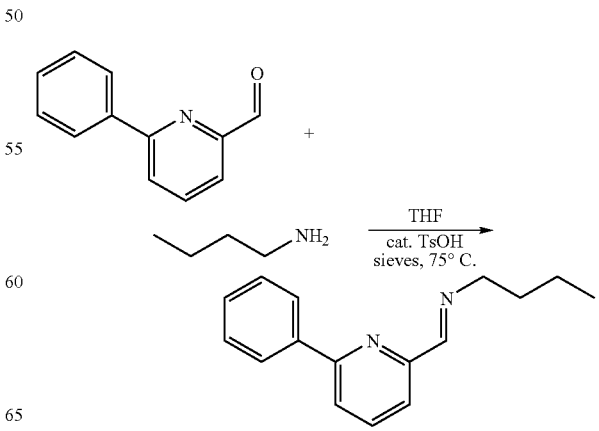

A solution of 916 mg (5 mmol) of 2-formyl-6-phenylpyridine and 402 mg (5.5 mmol) of n-butylamine in 50 mL of anhydrous THF containing 3 Å sieves and a catalytic amount of TsOH, was heated at 75° C. under N₂ for 8 h. Filtration and removal of the volatiles in vacuo provided 6-phenylpyridine-2-(n-butyl)imine as a yellow oil, which was used directly in subsequent nucleophilic reactions without purification.

Step 4

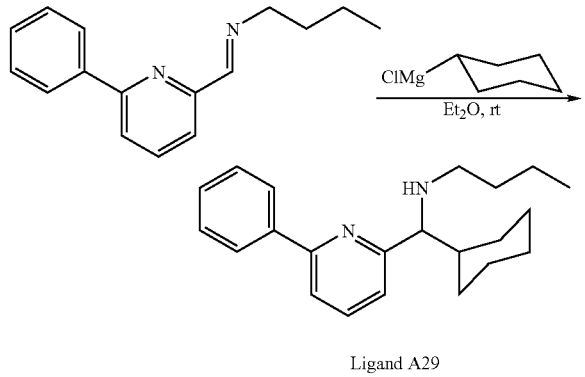

Ligand A29

To a vigorously-stirred solution of 6-phenylpyridine-2-(n-butyl)imine (300 mg, 1 mmol) in 2 mL of Et₂O under N₂, a solution of cyclohexylmagnesium chloride (600 μL of 2 M in Et₂O, 1.2 mmol) was added. After stirring at RT for 12 h, the reaction was quenched with aq. NH₄Cl. The organic layer was separated, washed with brine and H₂O, then was dried over Na₂SO₄. Following chromatography (alumina gel, 10% ethyl acetate/hexanes), the product was isolated as a yellow oil. The use of MgBr₂ as a complexing reagent can aid in the selectivity of Step 4, as described in U.S. Pat. No. 6,750,345 and U.S. Pat. No. 6,713,577. For certain ligands, the use of a complexing reagent is not necessary. In some cases the regioselectivity of Step 4 is such that the products of nucleophilic attack at both the imine carbon and the imine nitrogen can be isolated, e.g. ligands A29 and A38 can be obtained from the same reaction, with the product ratio depending on the conditions used.

Example 1b

Synthesis of Pyridyl-Amine Ligand A51: Example of Method B

Step 1

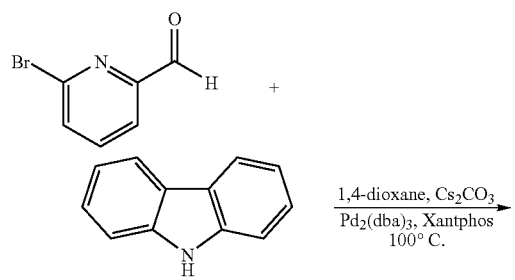

-continued

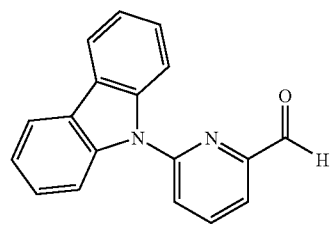

6-Bromopyridine-2-carboxaldehyde (1.86 g, 10.0 mmol) and carbazole (1.84 g, 11 mmol) were combined in anhydrous 1,4-dioxane (40 mL) under inert atmosphere. Cesium carbonate (4.56 g, 14 mmol), xantphos (0.382 mg, 0.66 mmol) and Pd₂(dba)₃ (0.275 g, 0.3 mmol) were added to the reaction mixture. The reaction mixture was sealed and heated at 100° C. for 72 h. The reaction was then cooled to ambient temperature, diluted with EtOAc (150 mL) and was washed with brine (75 mL). The organic layer was separated and dried over Na₂SO₄. The mixture was filtered, and the material was adsorbed onto neutral alumina for alumina chromatography. The material was eluted using a gradient of 0-20% EtOAc in hexanes. Fractions containing the product were pooled and evaporated yielding a product mixture as a yellow solid (2.28 g). GC-MS and ¹H NMR confirmed this mixture included the desired product and the starting carbazole. The material was carried on without further purification.

Step 2

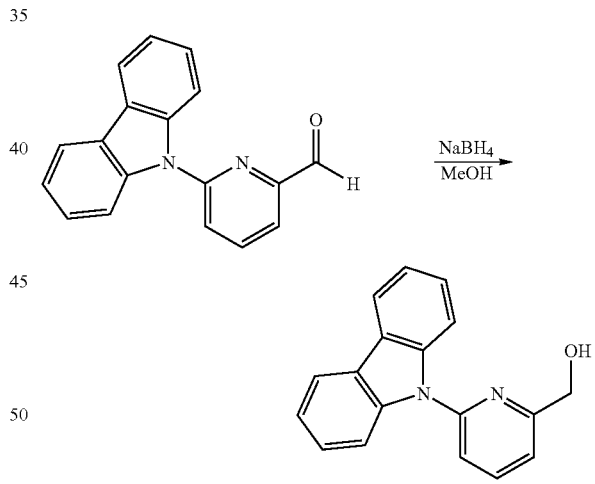

The product mixture described above (1.50 g) was taken up with stirring in methanol (12 mL). The resulting solution was cooled to 0° C. Sodium borohydride (0.313 g, 8.27 mmol) was added cautiously. The resulting mixture was stirred at 0° C. for 15 min. The reaction was heated at 80° C. for 1 h. The mixture was then poured into a brine solution (50 mL) and extracted with EtOAc (3×50 mL). The extracts were combined and dried over Na₂SO₄. The solution was filtered and adsorbed onto alumina gel for chromatography on neutral alumina. The material was eluted using a gradient of 0-20% EtOAc in hexanes. The product was obtained after evaporation of the eluent as a colorless foam (0.965 g).

Step 3

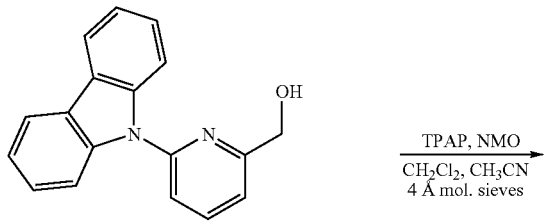

The 6-carbazolyl-2-hydroxymethylpyridine (0.965 g, 3.52 mmol) was dissolved in dichloromethane (35 mL) and acetonitrile (7 mL). N-methylmorpholine-N-oxide (0.619 g, 5.28 mmol) was added to the stirring solution followed by activated 4 Å-molecular sieves (2 g). The resulting mixture was stirred at ambient temperature for 15 min. Tetra-N-propylammonium-perruthenate (62 mg, 0.176 mmol) was then added in one portion, and the resulting mixture was stirred at ambient temperature for 38 h. The reaction was then quenched by addition of an aqueous 20% solution of sodium thiosulfate (10 mL). The organic layer was separated and the aqueous layer was extracted with $CH_2Cl_2$ (3×50 mL). The organic layer and extracts were combined and dried over $Na_2SO_4$. The material was adsorbed onto alumina gel for alumina chromatography. The material was eluted using a gradient of 0-20% diethyl ether in hexane. The product was obtained after evaporation of the eluent as a white solid (0.425 g).

Step 4

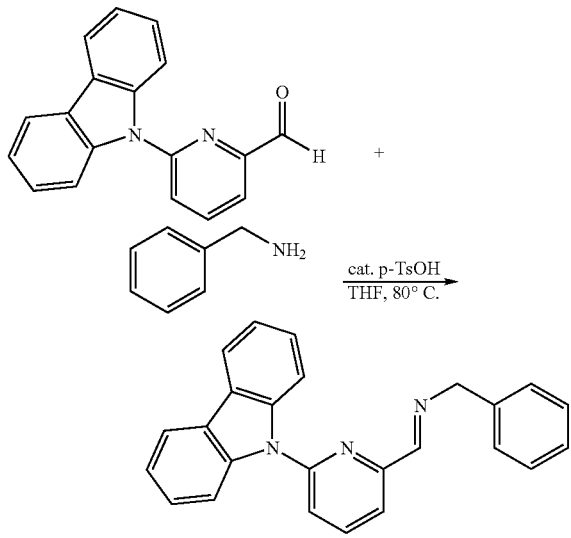

The 6-carbazolylpyridine-2-carboxaldehyde (0.358 g, 1.31 mmol) was taken up in anhydrous THF (16 mL). Benzylamine (0.154 g, 1.44 mmol), p-TsOH.$H_2O$ (30 mg, 0.158 mmol) and 4 Å-molecular sieves (2 g) were added to the stirring mixture. The reaction vessel was sealed and heated at 80° C. for 30 min. The reaction mixture was cooled to ambient temperature, diluted with EtOAc (50 mL) and filtered to remove the sieves. The resulting solution was washed with an aqueous 1.5 M $KHCO_3$ solution (30 mL). The organic layer was separated and dried over $Na_2SO_4$. The material was filtered, and the volatile materials were removed to yield the desired product as a white solid (0.425 g).

Step 5

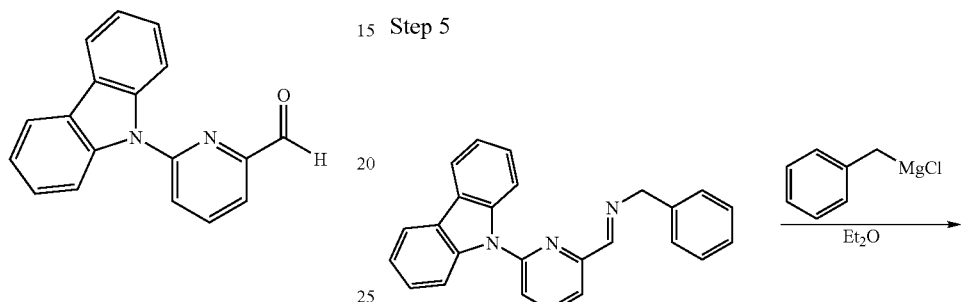

Ligand A51

The benzyl imine (0.425 g, 1.18 mmol) was taken up in anhydrous diethyl ether (10 mL). Benzylmagnesium chloride solution in diethyl ether (1.30 mL, 1.3 mmol) was added dropwise to the stirring solution. The resulting reaction mixture was stirred at ambient temperature for 1 h. The reaction mixture was then quenched by addition of brine (20 mL). The resulting mixture was extracted with EtOAc (3×50 mL). The organic extracts were combined and dried over $Na_2SO_4$. The solution was filtered, and the material was adsorbed onto alumina gel for alumina chromatography. The material was eluted using 50% diethyl ether in hexanes as the eluent. The product was obtained in this manner as a yellow solid (0.377 g).

Ligands illustrated in FIGS. 1, 2, 3 4 and 5 were prepared using the procedures detailed above, or through variations to these procedures that are apparent to one of ordinary skill in the art.

Example 2

Synthesis of Pyridyl-Amine Ligand A53: Example of $R_{20}$=alkyl

Step 1

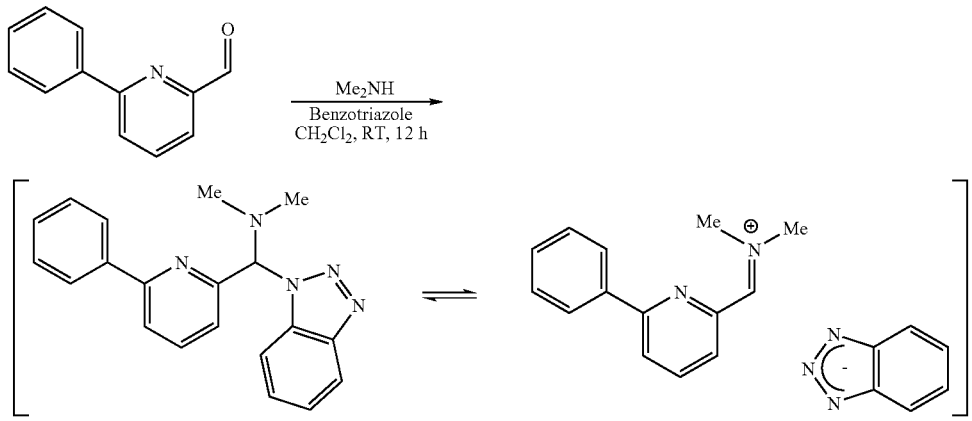

2-Formyl-6-phenylpyridine, 200 mg (1.10 mmol), and 130 mg (1.10 mmol) of benzotriazole were dissolved in 10 mL of anhydrous $CH_2Cl_2$ containing approximately 100 mg of $MgSO_4$ as a drying agent. Dimethylamine (0.61 mL of a 2M hexanes solution, 1.2 mmol) was added at ambient temperature. The mixture was vigorously stirred at ambient temperature for 12 h, then filtered to remove inorganic solids. The volatiles were removed in vacuo and the resultant yellow foam was used directly in subsequent nucleophilic reactions without purification.

Step 2

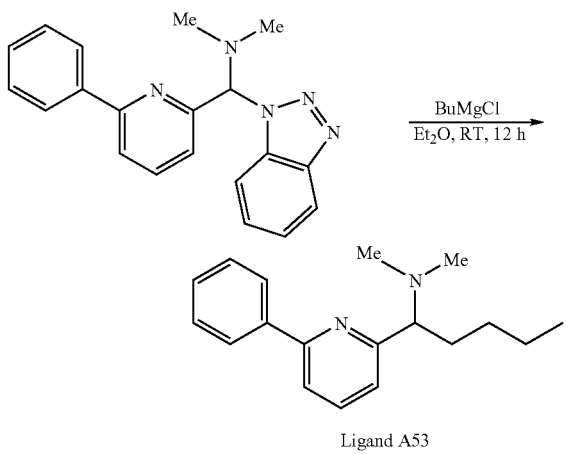

Ligand A53

To a vigorously-stirred solution of the crude 6-phenylpyridine-2-(dimethylamino)-benzotriazole iminium salt (330 mg, 1 mmol) in 2 mL of $Et_2O$ under $N_2$, a solution of butylmagnesium chloride (550 μL of 2 M in $Et_2O$, 1.1 mmol) was added. After stirring at RT for 12 h, the reaction was quenched with aq. $NH_4Cl$. The organic layer was separated, washed with brine and $H_2O$, then was dried over $Na_2SO_4$. Following chromatography (alumina gel, 10% ethyl acetate/hexanes), the product was isolated as a yellow oil.

Example 3

Synthesis of Pyridyl-Amine Ligand A74

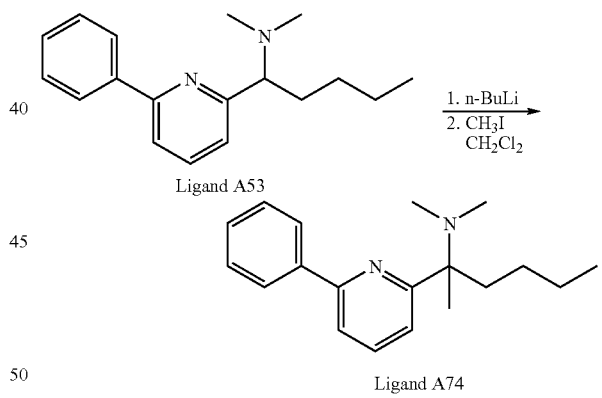

The pyridyl-amine ligand A53 (0.268 g, 1 mmol) was dissolved in 10 mL of anhydrous $CH_2Cl_2$ under inert atmosphere. The solution was cooled to −78° C. and n-butyllitium (0.69 mL of a 1.6 M solution in hexanes, 1.1 mmol) was added with stirring. The resulting solution was warmed to RT and stirred for 1 h. Methyl iodide was then added and the mixture was stirred at RT for 12 h. The reaction mixture was poured onto saturated $NH_4Cl$ and the organics separated. The organic layer was washed with brine, collected, and dried over $Na_2SO_4$. The product was adsorbed onto neutral alumina gel and purified via alumina chromatography, eluting with a gradient of 0-20% EtOAc in hexanes.

Figure 6:
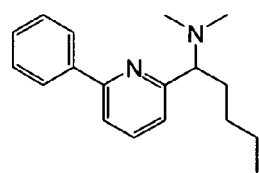
FIG. 6 illustrates pyridyl-amine ligands A53-A62 according to embodiments of the invention.
Figure 6:
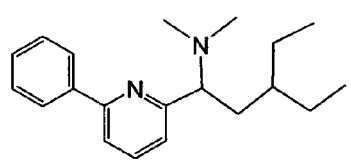
Figure 6:
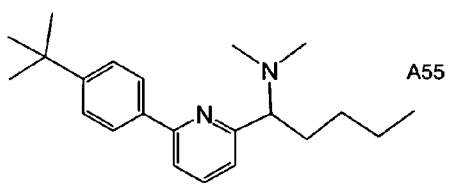
Figure 6:
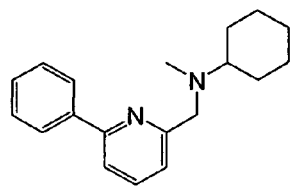
Figure 6:
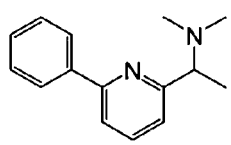
Figure 6:
Figure 6:
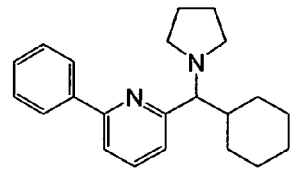
Figure 6:
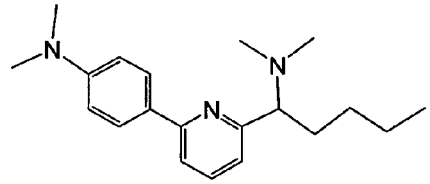
Figure 6:
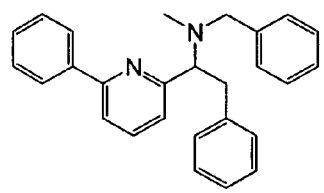
Figure 6:
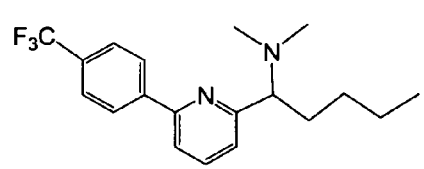
Figure 7:
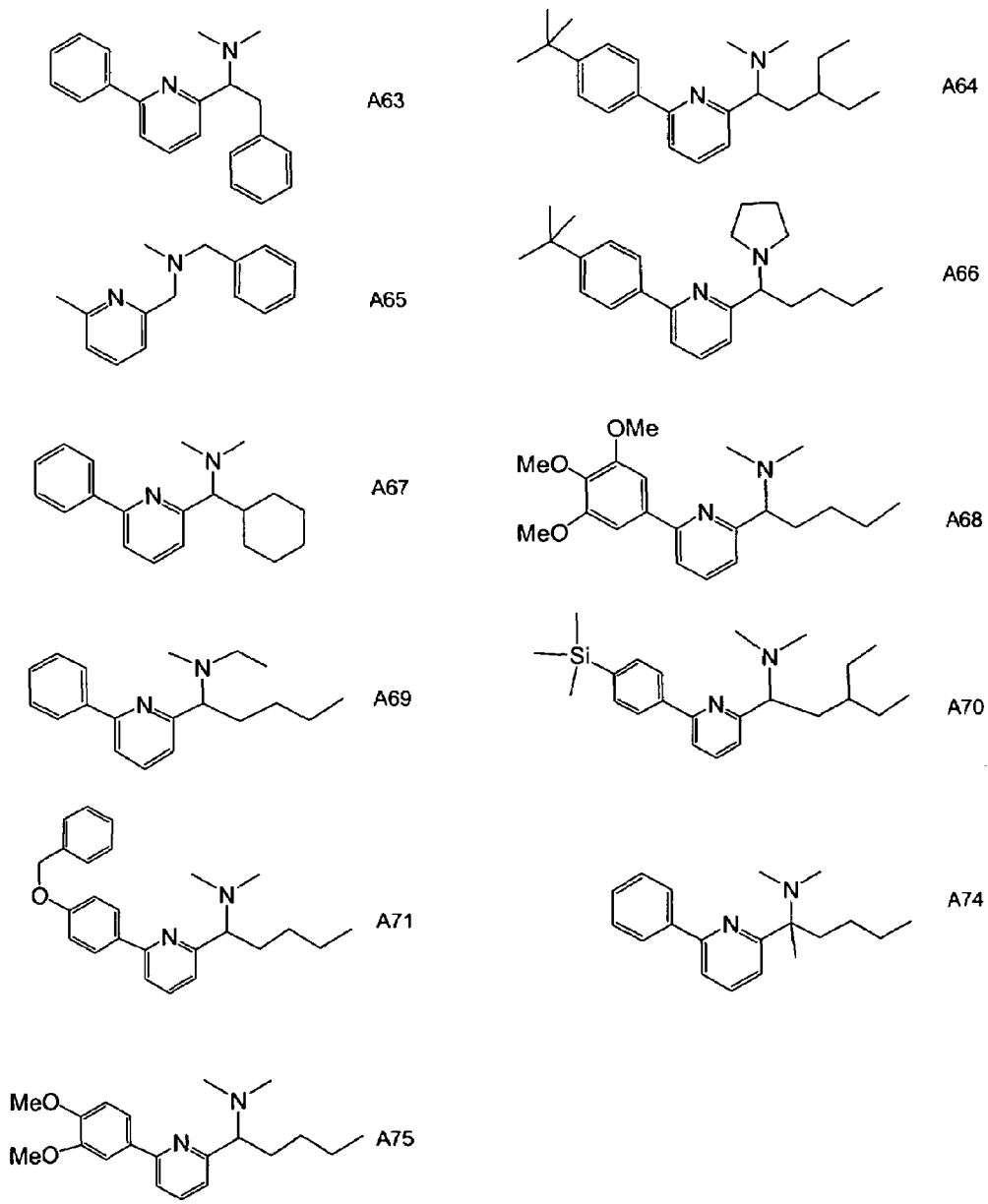
FIG. 7 illustrates pyridyl-amine ligands A63-A75 according to embodiments of the invention.

Ligands illustrated in FIGS. 6 and 7 were prepared using the procedures detailed above, or through variations to these procedures that are apparent to one of ordinary skill in the art.

Example 5

Selective Ethylene Oligomerization Examples in a 96-well Format

5a. General Protocols

Ethylene oligomerization reactions were performed in a 96-well format using 1 mL glass vials arranged in an 8×12 array within an aluminum block. Reagents were added from stock solutions or slurries to the 1 mL vials using a Cavro liquid handling robot driven by Symyx software, see, for example, U.S. Pat. No. 6,507,945, which is incorporated herein by reference, or a manual hand pipettor. The vials contained parylene coated stir-bars and were weighed prior to their use in screening (described below). Solutions of a parent array of desired ligands were transferred to arrays of glass vials (0.3 µmol of each ligand) and the solvent was then removed from the ligand array using a nitrogen or argon stream. The resultant ligand array was then contacted with a suitable chromium precursor, an activator (or combination of activators) and pressurized with ethylene within a parallel batch reactor with in situ injection capability. Specific details are described below. The parallel batch reactor is described in WO04/060550, and U.S. Application No. 2004/0121448, each of which is incorporated herein by reference.

Chromium Precursor Synthesis $(THF)_3CrMeCl_2$ was prepared as described in Nishimura, K. et al. *J. Organomet. Chem.* 37, pp 317-329 (1972). The compound $[\{TFA\}_2Cr(OEt_2)]_2$ has been previously described in Cotton, F. A. et al. *Inorg. Chem.* 17, pp 176-186 (1978), but was prepared by a different method described below. $(THF)_3CrPh_3$ was prepared as described in Herwig, W. and Zeiss, H. *J. Am. Chem. Soc.* 81, pp 4798-4801 (1959). $(Mes)_3Cr(THF)$ was prepared as described in Stolze, G. *J. Organomet. Chem.* 6, pp 383-388 (1966). $(Mes)CrCl(THF)_2$ was prepared as described by Stolze, G. et al. *J. Organomet. Chem.* 7, 301-310 (1967). All other Cr reagents were purchased from commercial sources.

Preparation of $[\{TFA\}_2Cr(OEt_2)]_2$

To a mixture of 1.00 g of $CrCl_2$ (8.14 mmol) and 1.96 g of LiTFA (16.28 mmol) was added 20 mL of diethyl ether. The pale green suspension was stirred for 15 h producing a deep violet supernatant with some traces of pale green solids. The suspension was reduced to dryness under a stream of argon and then was further dried in vacuo for about 5 minutes. The solids were then extracted with 40 mL of hexane and filtered, and were then further extracted twice with 20 mL of hexane and filtered. The filtrates were combined and reduced to dryness under a stream of argon, producing a deep purple, free-flowing crystalline solid. Isolated yield: 1.96 g.

Stock Solutions

Stock solution concentrations were as follows:

Chromium Precursors

For Complexations in Toluene: $(THF)_3CrMeCl_2$ (0.01 M in toluene), $(Mes)_3Cr(THF)$ (0.01 M in toluene), $[\{TFA\}_2Cr(OEt_2)]_2$ (0.005 M in toluene).

For Complexations in THF: $(THF)_3CrPh_3$ (0.005 M in THF), $(THF)_3CrMeCl_2$ (0.005 M in THF), $(Mes)_3Cr(THF)$ (0.005 M in THF), $[\{TFA\}_2Cr(OEt_2)]_2$ (0.005 M in THF).

Activators/Group 13 Reagents

Solutions of activators and group 13 reagents were prepared in toluene, n-heptane, or n-dodecane, depending on the choice of solvent for the selective ethylene oligomerization reaction (see Table 1). Alumoxanes were supplied by Akzo Chemical Inc., Chicago, Ill. MMAO-3A/$AlR_3$, PMAO-IP/$AlR_3$, and SJ2BF$_{20}$/$AlR_3$ mixtures were prepared within an hour prior to addition to the ligand-chromium precursor composition. Stock solutions were as follows:

MMAO-3A: 0.30 M plus 0.195 M cyclooctane as an internal standard).

MMAO-3A/TMA: 0.150 M MMAO-3A, 0.0375 M TMA plus 0.195 M cyclooctane as an internal standard.

PMAO-IP/TMA: 0.150 M PMAO-IP, 0.0375 M TMA plus 0.195 M cyclooctane as an internal standard.

MMAO-3A/TIBA: 0.150 M MMAO-3A, 0.0375 M TIBA plus 0.195 M cyclooctane as an internal standard.

SJ2BF$_{20}$/TMA: 0.0015 M SJ2BF$_{20}$, 0.0375 M TMA plus 0.195 M cyclooctane as an internal standard.

SJ2BF$_{20}$/TIBA: 0.0015 M SJ2BF$_{20}$, 0.0375 M TIBA plus 0.195 M cyclooctane as an internal standard.

5b. In Situ Preparation and Screening of Ligand-Chromium Compositions

Method 1: Toluene Room Temperature Complexation, Toluene Screening.

The ligand array (0.3 µmol of each ligand) was first contacted with toluene (ca. 30 µL per well) and then toluene solutions of the desired chromium precursor (ca. 30 µL per well, 0.3 µmol) were added. The resultant mixtures were stirred for a period of 1 hour at ambient temperature in the presence of 100-150 psi (0.67-1.03 MPa) of ethylene. The array was then treated with a stock solution of the appropriate activator (or activator mixture, 200 µL per well, contact time of ≦5 minutes), and placed into the parallel batch reactor and stirred at 50° C. under 150 psi (1.03 MPa) of ethylene for 1 hour.

Method 2: Toluene 75° C. Complexation, Toluene Screening.

The ligand array (0.3 µmol of each ligand) was first contacted with toluene (ca. 30 µL per well) and then toluene solutions of the desired chromium precursor (ca. 30 µL per well, 0.3 µmol) were added. The resultant mixtures were stirred for a period of 30 minutes at 75° C. in presence of 100-150 psi (0.67-1.03 MPa) of ethylene. The array was then cooled to room temperature and treated with a stock solution of the appropriate activator (or activator mixture, 200 µL per well, contact time of ≦5 minutes), and placed into the parallel batch reactor and stirred at 50° C. under 150 psi (1.03 MPa) of ethylene for 1 hour.

Method 3: THF Room Temperature Complexation, Toluene Screening.

The ligand array (0.3 µmol of each ligand) was contacted with THF solutions of the chromium complexes (ca. 60 µL per well, 0.3 µmol) and stirred at room temperature for a period of 2 hours (in the absence of ethylene). The THF was removed by directing a stream of nitrogen or argon over each well in the array. 60 µL of toluene was then added to each well in the array, which was subsequently stirred under 100-150 psi (0.67-1.03 MPa) of ethylene for 15 minutes. The array was then treated with a stock solution of the appropriate activator (or activator mixture, 200 µL per well, contact time of ≦5 minutes), and placed into the parallel batch reactor and stirred at 50° C. under 150 psi (1.03 MPa) of ethylene for 1 hour.

Method 4: Toluene 75° C. Complexation, Heptane or Dodecane Screening.

The procedure is identical to that described for method 2 above except that, following the complexation step, the toluene was removed by directing a stream of nitrogen or argon over each well in the array. 60 µL of n-heptane or n-dodecane was then added to each well in the array, which was then stirred under 100-150 psi (0.67-1.03 MPa) of ethylene for 15 minutes. The array was then treated with a stock solution of the appropriate activator (or activator mixture, 200 μL per well, contact time of ≦5 minutes), and placed into the parallel batch reactor and stirred at 50° C. under 150 psi (1.03 MPa) of ethylene for 1 hour.

Method 5: THF Room Temperature Complexation, Dodecane Screening.

The procedure is identical to that described for method 3, except that following the THF removal, each well of the array was treated with 60 μL of n-dodecane and then stirred under 100-150 psi (0.67-1.03 MPa) of ethylene for 15 minutes. The array was then treated with a stock solution of the appropriate activator (or activator mixture, 200 μL per well, contact time of ≦5 minutes), and placed into the parallel batch reactor and stirred at 50° C. under 150 psi (1.03 MPa) of ethylene for 1 hour.

Method 6: THF 50° C. Complexation, Dodecane Screening.

The ligand array (0.3 μmol of each ligand) was contacted with THF solutions of the chromium complexes (60 μL per well, 0.3 μmol) and stirred at 50° C. for a period of 1 hour (in the absence of ethylene). The array was then cooled to room temperature, whereupon the THF was removed by directing a stream of nitrogen or argon over each well in the array. Each well of the array was subsequently treated with 60 μL of n-dodecane and was stirred under 100-150 psi (0.67-1.03 MPa) of ethylene for 15 minutes. The array was then treated with a stock solution of the appropriate activator (or activator mixture, 200 μL per well, contact time of ≦5 minutes), and placed into the parallel batch reactor and stirred at 50° C. under 150 psi (1.03 MPa) of ethylene for 1 hour.

Method 7: Isolated Chromium-Ligand Composition from Ligand A4 and $CrMeCl_2(THF)_3$, Toluene or Dodecane Screening.

A solution of $CrMeCl_2(THF)_3$ (28.1 mg, 0.0793 mmol, 0.5 mL toluene) was added to a solution of Ligand A4 (30.0 mg, 0.0793 mmol, 0.5 mL toluene) at ambient temperature. After 15-20 minutes, a beige solid precipitated from solution. The mixture was allowed to stand for 12 hours. The mixture was filtered, and the isolated beige solid was washed with 2×0.5 mL toluene. The isolated solid was dissolved in THF, and the THF was removed under a stream of nitrogen. The solid was dried in vacuo for 30 minutes (isolated yield, 29 mg). A 0.005 M solution/slurry was prepared with the isolated solid in either toluene or n-dodecane. 60 μL of the toluene or n-dodecane isolated complex solution/slurry was then added to each well in the array. The resultant mixtures were stirred for a period of 5 minutes at ambient temperature in the presence of 100-150 psi of ethylene. The array was then treated with a stock solution of the appropriate activator (or activator mixture, 200 μL per well, contact time of ≦5 minutes), and placed into the parallel batch reactor and stirred at 50° C. under 150 psi of ethylene for 1 hour.

Method 8: Isolated Chromium-Ligand Composition from Ligand A4 and $CrCl_3(THF)_3$, Toluene or Dodecane Screening.

To a mixture of 30.0 mg (0.08 mmol) $CrCl_3(THF)_3$ and 30.3 mg (0.08 mmol) ligand A4 was added 2 mL of $CH_2Cl_2$. The reaction mixture became a violet-blue solution almost immediately and was stirred for 2 hours at room temperature. The volatiles were then removed by directing a stream of nitrogen over the solution and the blue-grey residues were dried in vacuo for 2 hours (isolated yield: 43 mg). A 0.005 M solution/slurry was prepared with the isolated solid in either toluene or n-dodecane. 60 μL of the toluene or n-dodecane isolated complex solution/slurry was then added to wells in a microtiter plate array of 1 mL glass vials and the resultant mixtures were stirred for a period of 15 minutes at ambient temperature in the presence of 100-150 psi of ethylene. The array was then treated with a stock solution of the appropriate activator (or activator mixture, 200 μL per well, contact time of ≦5 minutes), and placed into the parallel batch reactor and stirred at 50° C. under 150 psi of ethylene for 1 hour.

Method 9: Toluene 25° C. Complexation, Heptane Screening.

The procedure is identical to that described for method 1 above except that, following the complexation step, the toluene was removed by directing a stream of nitrogen or argon over each well in the array. 60 μL of n-heptane was then added to each well in the array, which was then stirred under 100-150 psi (0.67-1.03 MPa) of ethylene for 15 minutes. The array was then treated with a stock solution of the appropriate activator (or activator mixture, 200 μL per well, contact time of ≦5 minutes), and placed into the parallel batch reactor and stirred at 50° C. under 150 psi (1.03 MPa) of ethylene for 1 hour.

Method 10: THF 50° C. Complexation, Toluene Screening.

The ligand array (0.3 μmol of each ligand) was contacted with THF solutions of the chromium complexes (60 μL per well, 0.3 μmol) and stirred at 50° C. for a period of 1 hour (in the absence of ethylene). The array was then cooled to room temperature, whereupon the THF was removed by directing a stream of nitrogen or argon over each well in the array. Each well of the array was subsequently treated with 60 μL of Toluene and was stirred under 100-150 psi (0.67-1.03 MPa) of ethylene for 15 minutes. The array was then treated with a stock solution of the appropriate activator (or activator mixture, 200 μL per well, contact time of ≦5 minutes), and placed into the parallel batch reactor and stirred at 50° C. under 150 psi (1.03 MPa) of ethylene for 1 hour.

5c. Product Analysis.

After 1 hour of reaction, the parallel batch reactor was depressurized and the array was removed. The array of vials was then transferred to a room temperature aluminum block, and to each vial was added ca. 200 μL of toluene followed by 30-50 μL of water. The vials were stirred and then topped off with toluene to bring the total volume to ca. 800 μL. A Teflon sheet and rubber gasket were placed over the top of the array and an aluminum cover was screwed on the top to seal the array. The array was then mechanically agitated and centrifuged at 1500 rpm for 10 minutes before analyzing the composition of each well using Gas Chromatography with a Flame Ionization Detector (e.g. the GC-FID technique). Following the GC analysis of the array, the volatiles were removed under vacuum centrifuge and the vials were weighed in order to determine the yield of solid product. The calculated catalyst and cocatalyst residues were then subtracted from the weight to give the yield of polyethylene produced. Table 1 presents selected results from the selective ethylene oligomerization reactions performed in 96-well formats. In Table 1, 1-hexene selectivity is shown as a percentage and is defined as 100×[micromoles of 1-hexene]/[sum of micromoles of $C_6$-$C_{16}$ olefins (excluding dodecene when dodecane was used as solvent)].

TABLE 1

| Example | Ligand (0.3 μmol) | Chromium Precursor (0.3 μmol) | Method | Solvent | Reactor Temp (° C.) | Activation method and mol equivlalents versus Cr | μmol catalyst | μmol 1-hexene produced | 1-hexene Selectivity | mg polyethylene produced |
|---|---|---|---|---|---|---|---|---|---|---|
| 1 | A4 | (THF)$_3$CrMeCl$_2$ | 2 | Toluene | 50 | 100 PMAO-IP/25 TMA | 0.3 | 83 | 91 | 2 |
| 2 | A4 | (THF)$_3$CrMeCl$_2$ | 1 | Toluene | 50 | 100 PMAO-IP/25 TMA | 0.3 | 37 | 96 | 2 |
| 3 | A5 | (THF)$_3$CrMeCl$_2$ | 2 | Toluene | 50 | 100 PMAO-IP/25 TMA | 0.3 | 123 | 91 | 2 |
| 4 | A5 | (THF)$_3$CrMeCl$_2$ | 4 | Dodecane | 50 | 200 MMAO-3A | 0.3 | 105 | 93 | 3 |
| 5 | A2 | (THF)$_3$CrMeCl$_2$ | 2 | Toluene | 50 | 100 PMAO-IP/25 TMA | 0.3 | 64 | 88 | 3 |
| 6 | A2 | (THF)$_3$CrMeCl$_2$ | 1 | Toluene | 50 | 100 PMAO-IP/25 TMA | 0.3 | 30 | 91 | 2 |
| 7 | A9 | (THF)$_3$CrMeCl$_2$ | 5 | Dodecane | 50 | 200 MMAO-3A | 0.3 | 93 | 98 | 4 |
| 8 | A9 | (THF)$_3$CrMeCl$_2$ | 4 | Dodecane | 50 | 100 MMAO-3A/25 TIBA | 0.3 | 59 | 98 | 2 |
| 9 | A10 | (THF)$_3$CrMeCl$_2$ | 1 | Toluene | 50 | 100 PMAO-IP/25 TMA | 0.3 | 162 | 76 | 2 |
| 10 | A10 | (THF)$_3$CrMeCl$_2$ | 2 | Toluene | 50 | 100 PMAO-IP/25 TMA | 0.3 | 153 | 77 | 3 |
| 11 | A8 | (THF)$_3$CrMeCl$_2$ | 1 | Toluene | 50 | 100 PMAO-IP/25 TMA | 0.3 | 107 | 82 | 3 |
| 12 | A8 | (THF)$_3$CrMeCl$_2$ | 5 | Dodecane | 50 | 200 MMAO-3A | 0.3 | 68 | 80 | 3 |
| 13 | A7 | (THF)$_3$CrMeCl$_2$ | 5 | Dodecane | 50 | 200 MMAO-3A | 0.3 | 97 | 96 | 4 |
| 14 | A7 | (THF)$_3$CrMeCl$_2$ | 4 | Dodecane | 50 | 200 MMAO-3A | 0.3 | 42 | 95 | 4 |
| 15 | A12 | (THF)$_3$CrMeCl$_2$ | 2 | Toluene | 50 | 200 MMAO-3A | 0.3 | 43 | 86 | 6 |
| 16 | A22 | (THF)$_3$CrMeCl$_2$ | 2 | Toluene | 50 | 200 MMAO-3A | 0.3 | 59 | 93 | 3 |
| 17 | A23 | (THF)$_3$CrMeCl$_2$ | 1 | Toluene | 50 | 100 MMAO-3A/25 TMA | 0.3 | 229 | 94 | 2 |
| 18 | A23 | (THF)$_3$CrMeCl$_2$ | 2 | Toluene | 50 | 200 MMAO-3A | 0.3 | 88 | 89 | 3 |
| 19 | A26 | (THF)$_3$CrMeCl$_2$ | 1 | Toluene | 50 | 100 MMAO-3A/25 TMA | 0.3 | 55 | 95 | 2 |
| 20 | A26 | (THF)$_3$CrMeCl$_2$ | 2 | Toluene | 50 | 200 MMAO-3A | 0.3 | 84 | 99 | 4 |
| 21 | A32 | (THF)$_3$CrMeCl$_2$ | 2 | Toluene | 50 | 100 MMAO-3A/25 TMA | 0.3 | 73 | 98 | 4 |
| 22 | A32 | (THF)$_3$CrMeCl$_2$ | 2 | Toluene | 50 | 200 MMAO-3A | 0.3 | 56 | 95 | 6 |
| 34 | A28 | (THF)$_3$CrMeCl$_2$ | 1 | Toluene | 50 | 200 MMAO-3A | 0.3 | 275 | 92 | 2 |
| 35 | A28 | (THF)$_3$CrMeCl$_2$ | 2 | Toluene | 50 | 200 MMAO-3A | 0.3 | 459 | 91 | 3 |
| 36 | A29 | (THF)$_3$CrMeCl$_2$ | 1 | Toluene | 50 | 200 MMAO-3A | 0.3 | 559 | 87 | 3 |
| 37 | A29 | (THF)$_3$CrMeCl$_2$ | 2 | Toluene | 50 | 200 MMAO-3A | 0.3 | 965 | 90 | 3 |
| 38 | A29 | (THF)$_3$CrMeCl$_2$ | 4 | Heptane | 50 | 200 MMAO-3A | 0.3 | 731 | 91 | 3 |
| 39 | A30 | (THF)$_3$CrMeCl$_2$ | 1 | Toluene | 50 | 200 MMAO-3A | 0.3 | 136 | 94 | 3 |
| 40 | A30 | (THF)$_3$CrMeCl$_2$ | 2 | Toluene | 50 | 200 MMAO-3A | 0.3 | 260 | 92 | 3 |
| 41 | A30 | (THF)$_3$CrMeCl$_2$ | 4 | Heptane | 50 | 200 MMAO-3A | 0.3 | 303 | 92 | 3 |
| 42 | A36 | (THF)$_3$CrMeCl$_2$ | 1 | Toluene | 50 | 200 MMAO-3A | 0.3 | 150 | 94 | 4 |
| 43 | A36 | (THF)$_3$CrMeCl$_2$ | 2 | Toluene | 50 | 200 MMAO-3A | 0.3 | 268 | 95 | 7 |
| 44 | A36 | (THF)$_3$CrPh$_3$ | 3 | Toluene | 50 | 1 SJ2BF$_{20}$/25 TIBA | 0.3 | 30 | 93 | 21 |
| 45 | A36 | (THF)$_3$CrMeCl$_2$ | 4 | Heptane | 50 | 200 MMAO-3A | 0.3 | 512 | 93 | 4 |
| 46 | A37 | (THF)$_3$CrPh$_3$ | 3 | Toluene | 50 | 1 SJ2BF$_{20}$/25 TIBA | 0.3 | 101 | 84 | 3 |
| 47 | A4 | (Mes)$_3$Cr(THF) | 1 | Toluene | 50 | 1 SJ2BF$_{20}$/25 TMA | 0.3 | 41 | 89 | 2 |
| 48 | A38 | (THF)$_3$CrMeCl$_2$ | 4 | Heptane | 50 | 200 MMAO-3A | 0.3 | 105 | 98 | 3 |
| 49 | A39 | (THF)$_3$CrMeCl$_2$ | 1 | Toluene | 50 | 200 MMAO-3A | 0.3 | 105 | 80 | 5 |
| 50 | A40 | (THF)$_3$CrMeCl$_2$ | 2 | Toluene | 50 | 200 MMAO-3A | 0.3 | 110 | 91 | 4 |
| 51 | A41 | (THF)$_3$CrMeCl$_2$ | 4 | Heptane | 50 | 200 MMAO-3A | 0.3 | 124 | 94 | 5 |
| 52 | A4 | See Method 7 | 7 | Toluene | 50 | 200 MMAO-3A | 0.3 | 278 | 90 | 4 |
| 53 | A4 | See Method 7 | 7 | Dodecane | 50 | 200 MMAO-3A | 0.3 | 119 | 93 | 2 |
| 54 | A4 | See Method 8 | 8 | Toluene | 50 | 200 MMAO-3A | 0.3 | 156 | 84 | 3 |
| 55 | A4 | See Method 8 | 8 | Dodecane | 50 | 200 MMAO-3A | 0.3 | 191 | 89 | 3 |
| 56 | A49 | (THF)$_3$CrMeCl$_2$ | 4 | Heptane | 50 | 200 MMAO-3A | 0.3 | 211 | 88 | 4 |
| 57 | A49 | (THF)$_3$CrMeCl$_2$ | 2 | Toluene | 50 | 200 MMAO-3A | 0.3 | 184 | 89 | 3 |
| 58 | A51 | (THF)$_3$CrMeCl$_2$ | 1 | Toluene | 50 | 200 MMAO-3A | 0.3 | 178 | 90 | 8 |
| 59 | A51 | (THF)$_3$CrMeCl$_2$ | 9 | Heptane | 50 | 200 MMAO-3A | 0.3 | 171 | 96 | 5 |
| 60 | A51 | (THF)$_3$CrPh$_3$ | 3 | Toluene | 50 | 200 MMAO-3A | 0.3 | 142 | 92 | 9 |
| 61 | A51 | (THF)$_3$CrPh$_3$ | 10 | Toluene | 50 | 200 MMAO-3A | 0.3 | 101 | 92 | 10 |
| 62 | A52 | (THF)$_3$CrMeCl$_2$ | 9 | Heptane | 50 | 400 MMAO-3A | 0.3 | 148 | >99 | 5 |
| 63 | A52 | (THF)$_3$CrMeCl$_2$ | 1 | Toluene | 50 | 200 MMAO-3A | 0.3 | 102 | 89 | 3 |
| 64 | A58 | (THF)$_3$CrMeCl$_2$ | 2 | Toluene | 50 | 200 MMAO-3A | 0.3 | 115 | 94 | 3 |
| 65 | A58 | (THF)$_3$CrMeCl$_2$ | 4 | Heptane | 50 | 200 MMAO-3A | 0.3 | 71 | >99 | 3 |
| 66 | A48 | (THF)$_3$CrMeCl$_2$ | 1 | Toluene | 50 | 200 MMAO-3A | 0.3 | 375 | 94 | 3 |
| 67 | A48 | (THF)$_3$CrbMeCl$_2$ | 9 | Heptane | 50 | 200 MMAO-3A | 0.3 | 102 | 94 | 5 |
| 68 | A48 | [{TFA}$_2$Cr(OEt$_2$)]$_2$22 | 1 | Toluene | 50 | 100 MMAO-3A/25 TIBA | 0.3 | 37 | 77 | 14 |
| 69 | A21 | (THF)$_3$CrMeCl$_2$ | 2 | Toluene | 50 | 100 MMAO-3A/25 TIBA | 0.3 | 20 | 91 | 2 |
| 70 | A65 | (THF)$_3$CrMeCl$_2$ | 1 | Toluene | 50 | 200 MMAO-3A | 0.3 | 40 | 95 | 3 |
| 71 | A65 | (THF)$_3$CrMeCl$_2$ | 9 | Heptane | 50 | 200 MMAO-3A | 0.3 | 31 | >99 | 2 |
| 72 | A65 | (THF)$_3$CrMeCl$_2$ | 1 | Toluene | 50 | 100 MMAO-3A/25 TEAL | 0.3 | 31 | 96 | 2 |

Example 6

Selective Ethylene Oligomerization Reactions in a 48-Well Parallel Pressure Reactor 6a. Reactor Preparation A pre-weighed glass vial insert and disposable stirring paddle were fitted to each reaction vessel of the reactor.

Method A. The reactor was then closed, 0.330 mL of a 1.82 M solution of Modified Methylalumoxane 3A (from Akzo Chemical Inc., Chicago, Ill.) ("MMAO") in heptane and 4.70 mL of n-dodecane were injected into each pressure reaction vessel through a valve. The temperature was then set to the appropriate setting (with specific temperatures for each trimerization being listed in Table 2, below), and the stirring speed was set to 800 rpm, and the mixture was exposed to ethylene at 100 psi (0.67 MPa) pressure. An ethylene pressure of 100 psi (0.67 MPa) in the pressure cell and the temperature setting were maintained, using computer control, until the end of the selective oligomerization experiment.

Method B. The reactor was then closed, 0.256 mL of a 2.35 M solution of Modified Methylalumoxane 3A (from Akzo Chemical Inc., Chicago, Ill.) ("MMAO") in toluene and 4.75 mL of toluene were injected into each pressure reaction vessel through a valve. The temperature was then set to the appropriate setting (with specific temperatures for each trimerization being listed in Table 2, below), and the stirring speed was set to 800 rpm, and the mixture was exposed to ethylene at 100 psi (0.67 MPa) pressure. An ethylene pressure of 100 psi (0.67 MPa) in the pressure cell and the temperature setting were maintained, using computer control, until the end of the selective oligomerization experiment.

Method C. The reactor was then closed, 0.330 mL of a 1.82 M solution of Modified Methylalumoxane 3A (from Akzo Chemical Inc., Chicago, Ill.) ("MMAO") in heptane and 4.80 mL of heptane were injected into each pressure reaction vessel through a valve. The temperature was then set to the appropriate setting (with specific temperatures for each trimerization being listed in Table 2, below), and the stirring speed was set to 800 rpm, and the mixture was exposed to ethylene at 100 psi (0.67 MPa) pressure. An ethylene pressure of 100 psi (0.67 MPa) in the pressure cell and the temperature setting were maintained, using computer control, until the end of the selective oligomerization experiment.

Method D. Method D was similar to Method A, except that 0.330 mL of a 1.82 M solution of Modified Methylalumoxane 3A (from Akzo Chemical Inc., Chicago, Ill.) ("MMAO") in heptane and 4.80 mL of n-dodecane were injected into each pressure reaction vessel through a valve. The temperature and ethylene pressure were then set and maintained as in Method A.

6b. In-Situ Preparation of Chromium-Ligand Compositions

The following methods were employed to prepare chromium-ligand compositions for the examples presented in Table 2.

Method AA. 44 µl of the ligand solution (25 mM in toluene) was dispensed in a 1 mL glass vial in which a magnetic stir bar had been placed. To the 1 mL glass vial containing the ligand solution was added 110 µL of $CrMeCl_2(THF)_3$ solution (10 mM in toluene) to form the metal-ligand composition. The reaction mixture was heated to 75° C. for 30 minutes, with stirring. The solvent was then removed by passing a stream of argon over the reaction mixture. 150 µL of n-dodecane was then added to the metal-ligand composition, and the resulting mixture was stirred throughout subsequent activator addition and sampling steps.

Method BB. Method BB was similar to method M except that toluene solvent was not removed and n-dodecane was not added.

Method CC. 40 µl of the ligand solution (25 mM in toluene) was dispensed in a 1 mL glass vial in which a magnetic stir bar had been placed. To the 1 mL glass vial containing the ligand solution was added 100 µL of $CrMeCl_2(THF)_3$ solution (10 mM in toluene) to form the metal-ligand composition. The reaction mixture was heated to 75° C. for 30 minutes with stirring. The solvent was then removed by passing a stream of argon over the reaction mixture. 130 µL of heptane was then added to the metal-ligand composition, and the resulting mixture was stirred throughout subsequent activator addition and sampling steps.

Method DD. 50 µl of the ligand solution (20 mM in THF) was dispensed in a 1 mL glass vial in which a magnetic stir bar had been placed. To the 1 mL glass vial containing the ligand solution was added 100 µL of $[\{TFA\}_2Cr(OEt_2)]_2$ solution (10 mM (Cr concentration) in THF) to form the metal-ligand composition. The reaction mixture was stirred at room temperature for 2.5 hours. The solvent was then removed by passing a stream of argon over the reaction mixture. 150 µL of n-dodecane was then added to the metal-ligand composition, and the resulting mixture was stirred throughout subsequent activator addition and sampling steps.

Method EE. 100 µl of the ligand solution (10 mM in n-dodecane) was dispensed in a 1 mL glass vial in which a magnetic stir bar had been placed. To the 1 mL glass vial containing the ligand solution was added 200 µL of a 5 mM stirred suspension of $(Mes)CrCl(THF)_2$ in n-dodecane, to form the metal-ligand composition. The reaction mixture was stirred at room temperature for 3 hours, and the resulting mixture was stirred throughout subsequent activator addition and sampling steps.

6c. Preparation of the Group 13 Reagent and Activator Stock Solutions

The 600 mM solution of Modified Methylalumoxane 3A ("MMAO") in toluene was prepared by combining 5.10 mL of a 2.35 M solution of MMAO-3A in toluene (purchased from Akzo Chemical Inc., Chicago, Ill.) and 14.89 mL of toluene. The 600 mM solution of MMAO in heptane/n-dodecane was prepared by combining 6.60 mL of a 1.82 M solution of MMAO-3A in heptane (purchased from Akzo Chemical Inc., Chicago, Ill.) and 13.40 mL n-dodecane. The 600 mM solution of MMAO in heptane was prepared by combining 6.60 mL of a 1.82 M solution of MMAO-3A in heptane (purchased from Akzo Chemical Inc., Chicago, Ill.) and 13.40 mL heptane. The 200 mM solution of TIBA (Triisobutylaluminum) in n-dodecane was prepared by combining 1.59 g of neat Triisobutylaluminum (purchased from Aldrich, Milwaukee, Wis.) and 37.98 mL of n-dodecane. The 5 mM solution of "SJ2BF20" (N,N-di(n-decyl)-4-n-butyl-anilinium tetrakis (perfluorophenyl)borate, $[(4\text{-}n\text{-}Bu\text{-}C_6H_4)NH(n\text{-}decyl)_2]^+[B(C_6F_5)_4^-])$ in n-dodecane was prepared by combining 0.111 g of "SJ2BF20" (N,N-di(n-decyl)$_4$-n-butyl-anilinium tetrakis (perfluorophenyl)borate, $[(4\text{-}n\text{-}Bu\text{-}C_6H_4)NH(n\text{-}decyl)_2]^+[B(C_6F_5)_4^-])$ and 20 mL of n-dodecane, and was heated to approximately 85° C., with stirring, prior to and during use.

6d. Activation Methods and Injection of Solutions into the Pressure Reactor Vessel The following methods were employed to activate and inject the in-situ prepared chromium-ligand compositions into the parallel pressure reactor. The examples are presented in Table 2.

Method AAA. To the stirred metal-ligand composition in n-dodecane, 367 µL of a 600 mM solution of MMAO-3A in heptane/n-dodecane was added. After approximately 8 minutes, 50 µL n-dodecane were added to the 1 mL vial and the reaction mixture was mixed. Approximately 30 seconds later, a fraction of the 1 mL vial contents corresponding to 0.80 micromoles (µmol) of chromium precursor (412 µL), was injected into the prepressurized reaction vessel and was followed immediately by injection of n-dodecane to bring the total volume injected to 1.0 mL.

Method BBB. To the stirred metal-ligand composition in toluene, 367 µL of a 600 mM solution of MMAO-3A in toluene was added. After approximately 8 minutes, 50 µL toluene were added to the 1 mL vial and the reaction mixture was mixed. Approximately 30 seconds later, a fraction of the 1 mL vial contents corresponding to 0.80 micromoles (µmol) of chromium precursor (412 µL), was injected into the prepressurized reaction vessel and was followed immediately by injection of toluene to bring the total volume injected to 1.0 mL.

Method CCC. To the stirred metal-ligand composition in toluene, 333 µL of a 600 mM solution of MMAO-3A in heptane was added. After approximately 8 minutes, 50 µL heptane were added to the 1 mL vial and the reaction mixture was mixed. About another 30 seconds later, a fraction of the 1 mL vial contents corresponding to 0.60 micromoles (µmol) of metal precursor (308 µL), was injected into the prepressurized reaction vessel and was followed immediately by injection of n-dodecane to bring the total volume injected to 1.0 mL.

Method DDD. To the stirred metal-ligand composition in n-dodecane, 333 µL of a 600 mM solution of MMAO-3A in heptane/n-dodecane was added. After approximately 12 minutes, 150 µL n-dodecane were added to the 1 mL vial and the reaction mixture was mixed. Approximately 60 seconds later, a fraction of the 1 mL vial contents corresponding to 0.60 micromoles (µmol) of chromium precursor (380 µL), was injected into the prepressurized reaction vessel and was followed immediately by injection of n-dodecane to bring the total volume injected to 1.0 mL.

Method EEE. To the stirred metal-ligand composition in n-dodecane, 240 µL of a 5 mM solution of "SJ2BF20" (N,N-di(n-decyl)$_4$-n-butyl-anilinium tetrakis(perfluorophenyl)borate, [(4-n-Bu-C$_6$H$_4$)NH(n-decyl)$_2$]$^+$[B(C$_6$F$_5$)$_4$$^-$]) in n-dodecane was added. After approximately 12 minutes, 150 µL of a 200 mM solution of TIBA (Triisobutylaluminum) in n-dodecane was added to the 1 mL vial and the reaction mixture was mixed. Approximately 60 seconds later, a fraction of the 1 mL vial contents corresponding to 0.60 micromoles (µmol) of chromium precursor (324 µL), was injected into the prepressurized reaction vessel and was followed immediately by injection of n-dodecane to bring the total volume injected to 1.0 mL.

Method FFF. To the stirred metal-ligand composition in n-dodecane, 150 µL of a 200 mM solution of TIBA (Triisobutylaluminum) in n-dodecane was added. After approximately 12 minutes, 150 µL of n-dodecane was added to the 1 mL vial and the reaction mixture was mixed. Approximately 60 seconds later, a fraction of the 1 mL vial contents corresponding to 0.60 micromoles (µmol) of chromium precursor (360 µL), was injected into the prepressurized reaction vessel and was followed immediately by injection of n-dodecane to bring the total volume injected to 1.0 mL.

6e. Oligomerization Reactions

The trimerization reactions were allowed to continue for between 4.6 minutes and 60 minutes, during which time the temperature and pressure were maintained at their pre-set levels by computer control. The specific reaction times for each experiment are shown in Table 2. After the reaction time elapsed, the reaction was quenched by addition of an overpressure of oxygen (approximately 35 psi (241 kPa) of a 20% O$_2$/80% N$_2$ mixture) sent to the reactor. The reaction times were the lesser of the maximum desired reaction time or the time taken for a predetermined amount of ethylene gas to be consumed in the reaction.

6f. Product Analysis

After completion of the trimerizations reactions, the glass vial inserts containing the reaction products were removed from the pressure cell and removed from the inert atmosphere dry box, and deionized water (50 mL-100 mL) was added. The glass vial inserts were then centrifuged for approximately 10 minutes. 0.5 mL of the supernatant was then removed and analyzed by the GC-FID technique. The remaining supernatant was then decanted, and the vial insert containing insoluble residue was then placed in a centrifuge evaporator and the volatile components were removed. After most of the volatile components had evaporated, the vial contents were dried thoroughly (to constant weight) by evaporation at elevated temperature (approximately 80° C.) under reduced pressure in a vacuum oven. The vial was then weighed to determine the mass of solid product (final weight minus vial tare weight). The calculated mass of the catalyst and cocatalyst residue was then subtracted from the total mass to give the yield of polyethylene produced. Table 2 presents the results from the ethylene oligomerization reactions performed in a 48-well parallel pressure reactor.

In Table 2, 1-hexene selectivity is shown as a percentage and is defined as 100×[micromoles of 1-hexene]/[sum of micromoles of C$_6$-C$_{16}$ olefins (excluding dodecene when dodecane is used as solvent)].

Catalyst activity (TOF) for production of the desired oligomer (1-hexene) is defined as the [micromoles of 1-hexene]/[micromoles of catalyst]/[reaction time in minutes]*60 minutes/hour, as shown in the column "1-hexene TOF".

TABLE 2

| Example | Ligand | Chromium Precursor | Reactor Preparation Method | Complexation Method | Activation Method | Solvent | Reactor Temp (° C.) | Activation method and mole equivalents versus Cr |
|---|---|---|---|---|---|---|---|---|
| 73 | A2 | (THF)$_3$CrMeCl$_2$ | A | AA | AAA | Dodecane | 50 | 200 MMAO-3A |
| 74 | A4 | (THF)$_3$CrMeCl$_2$ | A | AA | AAA | Dodecane | 50 | 200 MMAO-3A |
| 75 | A5 | (THF)$_3$CrMeCl$_2$ | A | AA | AAA | Dodecane | 50 | 200 MMAO-3A |
| 76 | A9 | (THF)$_3$CrMeCl$_2$ | A | AA | AAA | Dodecane | 50 | 200 MMAO-3A |
| 77 | A10 | (THF)$_3$CrMeCl$_2$ | A | AA | AAA | Dodecane | 50 | 200 MMAO-3A |
| 78 | A2 | (THF)$_3$CrMeCl$_2$ | A | AA | AAA | Dodecane | 80 | 200 MMAO-3A |
| 79 | A4 | (THF)$_3$CrMeCl$_2$ | A | AA | AAA | Dodecane | 80 | 200 MMAO-3A |
| 80 | A5 | (THF)$_3$CrMeCl$_2$ | A | AA | AAA | Dodecane | 80 | 200 MMAO-3A |
| 81 | A35 | (THF)$_3$CrMeCl$_2$ | B | BB | BBB | Toluene | 50 | 200 MMAO-3A |
| 82 | A30 | (THF)$_3$CrMeCl$_2$ | C | CC | CCC | Heptane | 50 | 200 MMAO-3A |
| 83 | A28 | (THF)$_3$CrMeCl$_2$ | C | CC | CCC | Heptane | 50 | 200 MMAO-3A |
| 84 | A29 | (THF)$_3$CrMeCl$_2$ | C | CC | CCC | Heptane | 50 | 200 MMAO-3A |
| 85 | A30 | (THF)$_3$CrMeCl$_2$ | C | CC | CCC | Heptane | 80 | 200 MMAO-3A |
| 86 | A28 | (THF)$_3$CrMeCl$_2$ | C | CC | CCC | Heptane | 80 | 200 MMAO-3A |
| 87 | A29 | (THF)$_3$CrMeCl$_2$ | C | CC | CCC | Heptane | 80 | 200 MMAO-3A |

TABLE 2-continued

| Example | Group 13 reagent amount in reactor (micromole) | micromole catalyst | Reaction Time (min) | micromole 1-hexene produced | 1-hexene selectivity | 1-hexene TOF (mole/mole · hour) | mg polyethylene produced |
|---|---|---|---|---|---|---|---|
| 73 | 600 MMAO-3A | 0.8 | 19.3 | 210 | >99 | 800 | <2 |
| 74 | 600 MMAO-3A | 0.8 | 5.7 | 1130 | 99 | 14800 | <2 |
| 75 | 600 MMAO-3A | 0.8 | 7.5 | 1130 | 97 | 11300 | 5 |
| 76 | 600 MMAO-3A | 0.8 | 45 | 760 | >99 | 1260 | 20 |
| 77 | 600 MMAO-3A | 0.8 | 7.5 | 1110 | 85 | 11100 | 2 |
| 78 | 600 MMAO-3A | 0.8 | 7.8 | 1010 | 99 | 9690 | <2 |
| 79 | 600 MMAO-3A | 0.8 | 29 | 1130 | 98 | 2950 | <2 |
| 80 | 600 MMAO-3A | 0.8 | 30 | 1000 | 98 | 2510 | 3 |
| 81 | 600 MMAO-3A | 0.8 | 4.6 | 940 | 85 | 15200 | 31 |
| 82 | 600 MMAO-3A | 0.6 | 60 | 3570 | 96 | 5960 | 5 |
| 83 | 600 MMAO-3A | 0.6 | 52.7 | 4500 | 95 | 8540 | 3 |
| 84 | 600 MMAO-3A | 0.6 | 33.7 | 4180 | 96 | 12400 | 4 |
| 85 | 600 MMAO-3A | 0.6 | 60 | 2120 | 97 | 3540 | 4 |
| 86 | 600 MMAO-3A | 0.6 | 60 | 1310 | 99 | 2180 | 3 |
| 87 | 600 MMAO-3A | 0.6 | 17.5 | 4350 | 96 | 24900 | 4 |

6g. Synthesis of Isolated Chromium-Ligand Complexes

In the examples described below, the complex is typically shown in the form $(A')Cr(L)_m$, where A is the ligand of the invention and A' indicates that the ligand may be modified on binding to Cr. For example, the ligand may be modified by loss of a hydrogen atom via metallation of an aryl or heteroaryl substituent.

Complex M1 [(A4')CrCl$_2$]:

A toluene solution of CrMeCl$_2$(THF)$_3$ (28.1 mg, 0.0793 mmol, 0.5 mL toluene) was added to a toluene solution of Ligand A4 (30 mg, 0.0793 mmol, 0.5 mL toluene) at room temperature. A beige solid formed after 15-20 min. The reaction mixture was allowed to stand at room temperature for 16 hours. The reaction mixture was filtered, and the solid was washed with 2×0.5 mL toluene. The solid was redissolved in THF, the THF was removed under N$_2$ purge, and the solid was dried in vacuo for 30 minutes and isolated as a beige solid (isolated yield, 29 mg).

Complex M2 [(A34')CrCl$_2$]:

A toluene solution of CrMeCl$_2$(THF)$_3$ (26.3 mg, 0.0742 mmol, 0.7 mL toluene) was added to a toluene solution of Ligand A34 (33.3 mg, 0.0742 mmol, 0.7 mL toluene) at room temperature. The reaction mixture was allowed to stand at room temperature for 16 hours. The reaction mixture was then cooled to −35° C. for 16 hours whereupon a beige solid precipitated from the cold solution. The solid was isolated by filtering the solution while cold, then washing with pentane. The solid was dried in vacuo for 30 minutes and isolated as a beige solid (isolated yield, 22 mg).

Complex M3 [(A22')CrCl$_2$]:

A toluene solution of CrMeCl$_2$(THF)$_3$ (24.9 mg, 0.0703 mmol, 0.7 mL toluene) was added to a toluene solution of Ligand A22 (41.4 mg, 0.0738 mmol, 0.7 mL toluene) at room temperature. The reaction mixture was allowed to stand at room temperature for 1 hour. Pentane (3 mL) was layered onto the reaction mixture, which was then cooled to −35° C. for 16 hours. A beige solid precipitated from the cold solution and the solid was isolated by filtering the solution while cold, then washing with pentane (2×5 mL). After drying in vacuo for 30 minutes, the product was isolated as an oily brown solid (isolated yield, 31 mg).

Complex M4 [(A23')CrCl$_2$]:

A toluene solution of CrMeCl$_2$(THF)$_3$ (31.5 mg, 0.0889 mmol, 0.6 mL toluene) was added to a toluene solution of Ligand A23 (48.4 mg, 0.0933 mmol, 0.6 mL toluene) at room temperature. The reaction mixture was allowed to stand at room temperature for 1 hour. The volume of toluene was reduced to ca. 0.5 mL. The reaction mixture and the solution was allowed to stand at room temperature for 16 hours. Pentane (20 mL) was added to the reaction mixture, resulting in precipitation of a beige solid. The solid was isolated by filtration then washed with pentane. After drying in vacuo for 30 minutes, the product was isolated as an oily brown solid (isolated yield, 45 mg).

Complex M5 [(A29')CrCl$_2$]:

A toluene solution of CrMeCl$_2$(THF)$_3$ (153.0 mg, 0.4310 mmol, 20 mL toluene) was added to a toluene solution of Ligand A29 (142.0 mg, 0.4400 mmol, 20 mL toluene) at room temperature. The solution was heated at 75° C. for 1 hr, resulting in the formation of a light green solid. The reaction mixture was allowed to cool to room temperature and was filtered. The green solid was washed with 3-5 mL pentane and dried in vacuo for 4-5 hours (isolated yield, 154 mg).

Deuterium Labeling via Hydrolysis of Complex M5 [(A29')CrCl$_2$]

A small amount (5-10 mg) of Complex M5 was slurried in 2-3 mL of CH$_2$Cl$_2$ in a glove box. The slurry was removed from the glove box, and 0.7 mL of D$_2$O was added to produce an aqua blue solution. The solution was dried with Na$_2$SO$_4$ and filtered through alumina. The solvent was removed, and the residue was redissolved in CH$_2$Cl$_2$. One peak was observed in the $^2$H NMR spectrum at 8.1 ppm indicating deuteration at the ortho-position of the phenyl ring, consistent with the presence of a Cr-phenyl bond in Complex M5 which is cleaved upon hydrolysis with D$_2$O.

Complex M6: The Product of Complex M5 and PhMgBr

A THF slurry of Complex M5 (53.1 mg in 2 mL THF) was cooled to −35° C. and PhMgBr (1.0 M in THF, 205.6 µL, 0.2056 mmol) was added dropwise to the cold slurry. The reaction mixture was allowed to warm to room temperature over 1 hour. 1,4-Dioxane (220 µL) was then added to the reaction mixture resulting in the formation of a white precipitate. The white precipitate was filtered, and the THF was removed from the filtrate. The remaining dark brown residue was dissolved in 1 mL toluene, layered with 3 mL pentane, and cooled to −35° C. for 3 days. A brown solid precipitated from solution. The dark brown solid was isolated by removing the supernatant, washing with 2×3 mL pentane, and drying in vacuo for 30 minutes (isolated yield, 12 mg).

Complex M7: The Product of Complex M5 and MeMgBr

A THF slurry of Complex M5 (35.3 mg in 1.5 mL THF) was cooled to −35° C., and MeMgBr (3.22 M in Et$_2$O, 43 μL, 0.138 mmol) was added dropwise to the cold slurry. The reaction mixture was allowed to warm to room temperature over 1 hour. 1,4-Dioxane (220 μL) was then added to the reaction mixture resulting in the formation of a white precipitate. The white precipitate was filtered, and the THF was removed from the filtrate. The remaining dark brown residue was dissolved in a minimum amount of CH$_2$Cl$_2$ then added dropwise to 2 mL pentane. A brown solid precipitated from solution. The brown solid was isolated by removing the supernatant, washing with 2×3 mL pentane, and drying in vacuo for 15 minutes (isolated yield, 5.6 mg).

Complex M8 [(A29')Cr($\eta^2$-biphenyl)(THF)]: The Product of Complex M5 and o,o'-Biphenyldiyl Grignard Complex M5 (49.9 mg) was slurried in 10 mL THF and placed in a −35° C. freezer overnight. Magnesium turnings (19.2 mg, 790 μmols) were added to a solution of o,o'-dibromobiphenyl (30.7 mg, 98.4 μmoles) in 5 mL Et$_2$O, and the mixture was allowed to stir at room temperature overnight. The Grignard solution was cooled to −35° C. and added to the cold slurry of Complex M5 over 15 minutes forming an orange-red solution with off-white precipitate. The solution was allowed to warm to room temperature, during which time the off-white precipitate dissolved. Dioxane (150 μL) was added to precipitate the Mg salts, but no precipitate formed. The solvent was removed from the reaction mixture leaving a red residue with white solids which was dried under vacuum for 30 minutes. The residue was dissolved in 1 mL CH$_2$Cl$_2$, filtered, layered with 3 mL pentane, and placed in a −35° C. freezer for 3 days, during which time dark red solids precipitated from solution. The filtrate was removed, and the dark red solid residue was washed with cold pentane (1 mL). The product was dried under vacuum for 5 minutes (isolated yield, 31.7 mg).

General Synthesis of (A')CrCl$_2$

A toluene solution of CrMeCl$_2$(THF)$_3$ (1 equiv) was added to a toluene solution of a ligand of the invention (A) (1 equiv) at room temperature. The reaction mixture was stirred at 75° C. for 1.5-2 hours. During this time, the reaction mixture turned from a clear yellow-brown solution to a green solution with olive-green precipitate. The reaction mixture was cooled to room temperature, and the toluene was removed under a nitrogen stream. The resulting olive-green solid was dried in vacuo for 30 minutes.

Synthesis of M9 [(A53')CrCl$_2$]

A solution of 91.1 mg (0.340 mmol) ligand A53 in 4 mL of toluene was added to 120.3 mg (0.340 mmol; 1.0 eq.) of Cr(CH$_3$)Cl$_2$(THF)$_3$. The vial containing the ligand was rinsed with an additional 2 mL of toluene and was added into the reaction vessel to ensure complete transfer of the ligand solution to the chromium precursor, and the reaction mixture was stirred at 75° C. for 30 min. The green suspension was cooled to RT and placed in the freezer overnight. After warming to RT the suspension was filtered and the light green solids were washed with 3×4 mL of toluene and dried for 15 minutes in vacuo producing a light green solid (yield 0.116 g). (Anal calc %: C, 55.39; H, 5.94; Cl, 18.17; N, 7.18. Found (avg. for duplicate): C, 55.46; H, 5.81; Cl, 16.29; N, 7.09)

Deuterium Labeling via Hydrolysis of Complex M9 [(A53')CrCl$_2$]

A small amount (5-10 mg) of Complex M9 was slurried in 2-3 mL of CH$_2$Cl$_2$ in a glove box. The slurry was removed from the glove box, and 0.7 mL of D$_2$O was added to produce an aqua blue solution. The solution was dried with MgSO$_4$ and filtered through alumina. The solvent was removed, and the residue was redissolved in CH$_2$Cl$_2$. A $^2$H NMR spectrum was taken, and one peak was observed at 8.1 ppm indicating deuteration at the ortho-position of the phenyl ring. This data is consistent with the presence of a Cr-phenyl bond in Complex M9 which is cleaved upon hydrolysis with D$_2$O.

Synthesis of M10 [(A55')CrCl$_2$]

A toluene solution of CrMeCl$_2$(THF)$_3$ (52 mg, 0.15 mmol, 1 equiv, 2 mL toluene) was added to a toluene solution of A55 (48 mg, 0.15 mmol, 1 equiv, 5 mL) at room temperature. The reaction mixture was stirred at 75° C. for 90 minutes. The reaction mixture was cooled to room temperature, and the toluene was removed under a nitrogen stream. The resulting dark green, microcrystalline solid was dried in vacuo for 30 minutes. 18 mg of product were obtained. (Anal calc %: C, 59.19; H, 7.00; N, 6.28. Found C, 58.51; H, 6.85; N, 5.69)

The same method was used to synthesize the following complex:

| Ligand # | Complex # | Amount CrMeCl$_2$(THF)$_3$ | Amount of Ligand | Yield |
|---|---|---|---|---|
| A71 | M11 | 47 mg | 50 mg | 17 mg |

Synthesis of M12 [(A42')CrCl$_2$]

A toluene solution of CrMeCl$_2$(THF)$_3$ (73 mg, 0.21 mmol, 1 equiv, 2 mL toluene) was added to a toluene solution of A42 (78 mg, 0.21 mmol, 1 equiv, 8 mL toluene) at room temperature. The reaction mixture was stirred at 75° C. for 90 minutes, during which time the reaction mixture turned from a clear dark olive green solution to brown solution to a rust colored solution with brick red precipitate. The reaction mixture was cooled to room temperature, filtered through a glass microfiber filter, and the orange solid was collected and dried in vacuo for 2 hours. 48 mg of product was obtained. (Anal calc %: C, 57.60; H, 5.84; Cl, 14.17; N, 5.60. Found C, 56.36; H, 5.65; Cl, 13.37; N, 5.11)

Deuterium Labeling via Hydrolysis of M12 [(A42')CrCl$_2$]

32 mg of Complex M12 was slurried in 5 mL of CH$_2$Cl$_2$ in a glove box. The slurry was removed from the glove box, and 1 mL of D$_2$O was added to the mixture. The mixture was shaken and left at room temperature for 6 hours. The solution was filtered through alumina and rinsed with CH$_2$Cl$_2$. The resulting dark green solution was dried with Na$_2$SO$_4$ and filtered. The solvent was removed, and the residue was redissolved in CH$_2$Cl$_2$. A $^2$H NMR spectrum showed one peak at 7.8 ppm, indicating deuteration at the carbon of the thiazole ring, in the ortho position to the pyridine, by comparison with the $^1$H NMR spectrum of free A42. This data is consistent with the presence of a Cr-carbon bond in M12 which is cleaved upon hydrolysis with D$_2$O.

Synthesis of M13 [(A29')Cr(acac)Cl]

To a mixture of 30.0 mg of Complex M5 and 12.3 mg (0.116 mmol) of Li(acac) (where acac=acetylacetonate=2,4-pentanedionate) was added 4.5 mL of toluene and the green suspension was stirred at 75° C. for 15.5 h. The red-brown suspension was cooled to RT, filtered and then blown down with a stream of nitrogen to remove volatiles. The residues were dried overnight in vacuo producing a red-brown solid (yield: 39 mg) which was recrystallized by slow diffusion of pentane into a saturated THF solution at −35° C. Red crystals of the product were isolated and characterized by X-ray crystallography (see FIG. 8). (Anal calc %: Cl, 6.98. Found Cl, 6.15).

The analogous method was used to synthesize the following compounds:

| Ligand ID | Complex ID | Amount [(A')CrCl$_2$] | Amount Li(acac) | Yield |
|---|---|---|---|---|
| A53 | M14 | 30 mg | 13.8 mg | 37 mg |

Synthesis of M14 [(A53')Cr(acac)Cl]

Solid CrMeCl$_2$(THF)$_3$ (58 mg, 0.16 mmol, 1 equiv) was added to a toluene solution of A53 (44 mg, 0.16 mmol, 1 equiv, 3 mL toluene) at room temperature. The reaction mixture was stirred at 75° C. for 90 minutes, during which time the reaction mixture turned from a clear yellow-brown solution to a green solution with a yellow-green precipitate. The reaction mixture was cooled to room temperature, and the toluene was removed under a nitrogen stream. The solid was dried under vacuum for 2 hours. The yellow-green solid was slurried in CH$_2$Cl$_2$ (5 mL). A THF slurry of Li(acac) (17 mg, 0.16 mmol, 1 equiv, 2 mL THF) was added to this mixture at room temperature. The resulting mixture was stirred at 75° C. for 60 minutes, during which time the mixture turned from a clear green solution to brown to a clear, bright orange-red solution. The solvent volume was reduced to 2 mL under a stream of nitrogen, and pentane was added until solid precipitated. The solution was dried under a stream of nitrogen. The product was taken up in CH$_2$Cl$_2$ and filtered to remove LiCl. The filter was washed with 2×1 mL of CH$_2$Cl$_2$, and the combined filtrate was dried under a stream of nitrogen to leave an orange-red powder. This powder was dissolved in 2 mL of THF, layered with 4 mL of pentane, and left to recrystallize at −35° C. The supernatant was removed by pipette and the solid was dried in vacuo for 2 hours. 51 mg of product was obtained. (Anal calc %: C, 60.85; H, 6.66; N, 6.17; Cl, 7.81. Found C, 60.40; H, 6.96; N, 6.08; Cl, 7.43.)

The same method was used to synthesize the following complexes:

| Ligand # | Complex # | Amount CrMeCl$_2$(THF)$_3$ | Amount of Ligand | Amount Li(acac) | Yield |
|---|---|---|---|---|---|
| A69 | M15 | 22 mg | 18 mg | 6.6 mg | 5 mg |
| A66 | M16 | 22 mg | 22 mg | 6.7 mg | 35 mg |
| A60 | M17 | 18 mg | 16 mg | 5.4 mg | 21.1 mg |
| A64 | M18 | 24 mg | 24 mg | 7.2 mg | 6.2 mg |
| A70 | M19 | 36 mg | 37 mg | 10.6 mg | 17 mg |

Complex M20 [(A54')Cr(acac)Cl]:

A solution of CrMeCl$_2$(THF)$_3$ (24 mg, 0.068 mmol, 1 equiv, 2 mL toluene) was added to a toluene solution of A54 (20 mg, 0.068 mmol, 1 equiv, 5 mL toluene) at room temperature. The reaction mixture was stirred at 75° C. for 90 minutes, during which time the reaction mixture turned from a clear yellow-brown solution to an olive green solution with an olive green precipitate. The reaction mixture was cooled to room temperature, and Li(acac) (14 mg, 0.13 mmol) was added to the mixture. The reaction mixture was stirred at 75° C. for 22 hours, during which time it changed color to yellow and then to a clear amber solution. The reaction mixture was cooled to room temperature and filtered through a glass microfiber filter. The filter was washed with 2×1.5 mL of toluene, and the combined filtrate was dried under a nitrogen stream. The resulting red-orange solid was dissolved in 2 mL of THF and pentane was added until a fine powder began to precipitate (approximately 4.5 mL of pentane were added total). The solution was left to recrystallize at −35° C. The supernatant was removed by pipette and the solid was dried in vacuo for 2 hours. 37 mg of product was obtained.

The same method was used to synthesize the following complexes:

| Ligand # | Complex # | Amount CrMeCl$_2$(THF)$_3$ | Amount Ligand | Amount Li(acac) | Yield |
|---|---|---|---|---|---|
| A61 | M21 | 48 mg | 51 mg | 29 mg | 30 mg |
| A71 | M22 | 47 mg | 50 mg | 28 mg | 4 mg |
| A62 | M23 | 60 mg | 57 mg | 36 mg | 49 mg |
| A44 | M25 | 61 mg | 62 mg | 37 mg | 6 mg |
| A68 | M26 | 67 mg | 70 mg | 40 mg | 11 mg |
| A63 | M27 | 54 mg | 46 mg | 32 mg | 9 mg |
| A58 | M28 | 73 mg | 68 mg | 44 mg | 21 mg |
| A57 | M24 | 63 mg | 40 mg | 37 mg | 27 mg |
| A67 | M29 | 84 mg | 70 mg | 50 mg | 17 mg |
| A59 | M30 | 69 mg | 62 mg | 41 mg | 16 mg |
| A55 | M31 | 52 mg | 48 mg | 31 mg | 7 mg |
| A56 | M32 | 70.0 mg | 55.4 mg | 15.9 mg | 45.0 mg |
| A75 | M42 | 54.9 mg | 50.8 mg | 32.9 mg | 88 mg |

(Complex M24 elemental analysis: Anal calc %: C, 58.32; H, 5.87; N, 6.80. Found C, 58.18; H, 5.61; N, 7.11.)

(Complex M42 elemental analysis: Anal calc %: C, 58.42; H, 6.67; N, 5.45. Found C, 58.37; H, 6.55; N, 5.00.)

Complex M33 [(A53')Cr(acac)CH$_2$Ph]: The Product of (7498)Cr(acac)Cl and PhCH$_2$MgCl Complex M14 [(A53')Cr(acac)Cl] (20.5 mg, 0.045 mmol, 1 equiv) was placed in a vial and 3 mL of THF were added. This solution was cooled to −35° C. While stirring this solution, a THF solution of PhCH$_2$MgCl (22.6 μL of a 2.0 M solution, 0.045 mmol, 1 equiv) was added, at which point the reaction mixture rapidly turned an orange-brown color. After 5 minutes the THF was removed under a nitrogen stream. The reaction mixture was stored at −35° C. for 3 days. The orange-brown oil was dissolved in toluene, dioxane was added to precipitate magnesium salts, and the mixture was filtered to leave an orange solution. Solvent was removed under a nitrogen stream. The product was recrystallized from a mixture of THF and pentane at −35° C. 10 mg of product was obtained.

Complex M34 [(A29')Cr(O$_2$CCF$_3$)$_2$]:

To a mixture of 30.1 mg of M5 and 25.8 mg (0.117 mmol) of Ag(O$_2$CCF$_3$) (silver trifluoroacetate) was added 2.0 mL of CH$_2$Cl$_2$ and the reaction mixture was stirred at RT for 30 min. At this point, the reaction mixture was a red-brown suspension and additional CH$_2$Cl$_2$ was added in two stages (2 mL after 30 minutes, an additional 10 mL after an additional 70 minutes). After 8 hours stirring, the reaction mixture was filtered and the volatiles removed with a stream of nitrogen.

The oily red-brown residues were then dried in vacuo overnight. 37 mg of product were obtained.

Synthesis of Potassium (3-n-pentyl-2,4-pentanedionate) [K(3-n-pentyl-acac)]

Inside the drybox, 3-n-pentyl-2,4-pentanedione (1 g, 5.87 mmol, 1 eq.) was diluted with 10 ml THF, and the solution was added dropwise to a stirred suspension of potassium tert-butoxide (0.659 g, 5.87 mmol, 1 eq.) in 20 ml THF. Upon addition, the reaction became homogeneous and changed color to yellow-orange, and after approximately 5 minutes a white precipitate began to form. The reaction was stirred overnight at room temperature, during which time more white precipitate formed. The reaction mixture was centrifuged to compact the solids and the supernatant was decanted via pipette. The solids were washed with 15 ml toluene, the vial was centrifuged, and the supernatant decanted. The procedure was repeated twice more, and a final wash was done with pentane to remove the residual toluene. The remaining white solids were blown dry with nitrogen and dried in vacuo (0.738 g, 3.54 mmol, 60% yield).

Complex M35 [(A29')Cr(3-n-pentyl-acac)Cl]:

M5 (20 mg) and K(3-n-pentyl-acac) (8.7 mg, 0.042 mmol) were weighed into an 8 ml vial equipped with a stirbar inside a drybox. 2-3 ml of THF were added via pipette, the vial was capped, and the reaction was stirred at room temperature for 3 hours, during which time the solution became orange-brown with fine off-white solids. The solvent was removed using a nitrogen stream and the residue was dried in vacuo. 2 ml of toluene were added to the dry residue to extract the product. The mixture was passed through a glass microfiber filter to remove the potassium salts, and the reaction vial and filter cake were washed with an additional 2×1 ml toluene. The orange-brown filtrate was concentrated using a nitrogen stream and dried in vacuo overnight, resulting in 21.2 mg (0.037 mmol, 96% yield) of an orange-brown residue. The product was lyophilized from benzene to produce an orange-brown solid. (Anal calc %: C, 66.52; H, 8.03; N, 4.85. Found C, 66.65; H, 8.04; N, 4.56).

The same method was used to synthesize the following complex:

| Ligand # | Complex # | Amount [(A')CrCl$_2$] | Amount K(3-n-pentyl-acac) | Yield |
|---|---|---|---|---|
| A53 | M36 | 10 mg | 4.9 mg | 12.3 mg |

Complex M37 [(A29')Cr(3-n-pentyl-acac)$_2$]:

M5 (15 mg) and K(3-n-pentyl-acac) (12.1 mg, 0.058 mmol) were weighed into an 8 ml vial equipped with a stirbar, inside a drybox. 2-3 ml of THF were added via pipette, the vial was capped, and the reaction was stirred at room temperature for 1 hour, during which time the solution became orange-brown with fine off-white solids. The solvent was removed using a nitrogen stream and the residue was dried in vacuo. 2 ml of pentane were added to the dry residue to extract the product. The mixture was passed through a glass microfiber filter to remove the potassium salts, and the reaction vial and filter cake were washed with an additional 2×1 ml pentane. The orange-brown filtrate was concentrated using a nitrogen stream and dried in vacuo overnight, resulting in 20.5 mg (0.028 mmol, 97% yield) of a brown residue. The product was lyophilized from benzene to produce a light brown solid. (Anal calc %: C, 70.84; H, 8.92; N, 3.94. Found C, 70.61; H, 8.80; N, 3.91).

The same method was used to synthesize the following complexes:

| Ligand # | Complex # | Amount [(A')CrCl$_2$] | Amount K(3-n-pentyl-acac)) | Yield |
|---|---|---|---|---|
| A53 | M38 | 18 mg | 16.2 mg | 24.5 mg |
| A71 | M39 | 11 mg | 17 mg | 6 mg |
| A62 | M40 | 41 mg | 47 mg | 83 mg |
| A55 | M41 | 35 mg | 40 mg | 61 mg |

(Complex M38 elemental analysis: Anal calc %: C, 69.37; H, 8.74; N, 4.26. Found C, 69.45; H, 8.81; N, 4.20).

6h. Selective Ethylene Oligomerizations Using Isolated Chromium-Ligand Compositions M3 and M4

Reactor Preparation: The polymerization reactor was prepared according to Method A, above.

Preparation of the Activator Stock Solution: A 600 mM solution of MMAO-3A in heptane/n-dodecane was prepared as described above.

Preparation of Composition Slurries:

M3: 12.0 mg of Composition M3 and 3.180 mL n-dodecane were combined. A slurry was prepared by stirring the mixture vigorously for 3 hours.

M4: 12.0 mg of Composition M4 and 3.368 mL n-dodecane were combined. A slurry was prepared by stirring the mixture vigorously for 3 hours.

Activation Method and Injection of Solutions into the Pressure Reactor Vessel

333 µL of a 600 mM solution of MMAO in heptane/n-dodecane was dispensed into a 1 mL vial. 200 µL of the composition slurry was added. After approximately 9 minutes, 50 µL n-dodecane were added to the 1 mL vial and the contents of the vial were mixed. About another 30 seconds later, 466 µL of the vial contents were injected into the pre-pressurized reaction vessel and was followed immediately by injection of n-dodecane (534 µL) to bring the total volume injected to 1.0 mL.

The oligomerization reactions, workup, and product analysis were performed as described in Sections 6e and 6f above. The results are presented in Table 3. In Table 3, 1-hexene selectivity is shown as a percentage and is defined as 100× [micromoles of 1-hexene]/[sum of micromoles of $C_6$-$C_{16}$ olefins (excluding dodecene when dodecane is used as solvent)].

TABLE 3

| Example | Composition | Reactor Preparation Method | Solvent | Reactor Temp (°C.) | Activation method and mole equivalents versus Cr | Group 13 reagent amount in reactor (micromole) | Reaction Time (min) | micromole 1-hexene produced | 1-hexene selectivity | 1-hexane TOF (mole/mole · hour) | mg polyethylene produced |
|---|---|---|---|---|---|---|---|---|---|---|---|
| 88 | M3 | A | Dodecane | 50 | 200 MMAO-3A | 600 MMAO-3A | 60 | 870 | 98 | 1080 | 14 |
| 89 | M3 | A | Dodecane | 50 | 200 MMAO-3A | 600 MMAO-3A | 60 | 770 | 98 | 960 | 10 |
| 90 | M3 | A | Dodecane | 80 | 200 MMAO-3A | 600 MMAO-3A | 30 | 470 | 96 | 1170 | 5 |
| 91 | M3 | A | Dodecane | 80 | 200 MMAO-3A | 600 MMAO-3A | 30 | 350 | 99 | 870 | 4 |
| 92 | M4 | A | Dodecane | 50 | 200 MMAO-3A | 600 MMAO-3A | 31 | 1960 | 97 | 4740 | 7 |
| 93 | M4 | A | Dodecane | 50 | 200 MMAO-3A | 600 MMAO-3A | 60 | 2160 | 97 | 2700 | 5 |
| 94 | M4 | A | Dodecane | 80 | 200 MMAO-3A | 600 MMAO-3A | 30 | 920 | 99 | 2310 | 6 |
| 95 | M4 | A | Dodecane | 80 | 200 MMAO-3A | 600 MMAO-3A | 30 | 870 | 97 | 2180 | 4 |

6i. Selective Oligomerization Examples Using Isolated Chromium-Ligand Composition M5

Reactor Preparation: The polymerization reactor was prepared according to Method C, above.

Preparation of the Group 13 Reagent and Activator Stock Solutions: The 1.0 M solution of MMAO in heptane was prepared by combining 4.40 mL of a 1.82 M solution of MMAO-3A in heptane (purchased from Akzo Chemical Inc., Chicago, Ill.) and 3.60 mL of heptane. The 200 mM solution of TMA (trimethylaluminum) in heptane was prepared by combining 0.58 g of neat trimethylaluminum (purchased from Aldrich, Milwaukee, Wis.) and 39.2 mL of heptane.

Activation Method and Injection of Solutions into the Pressure Reactor Vessel

Preparation of Composition M5/MMAO Mixture: 4.9 mg of Composition M5 and 1.90 mL of a 1.0 M solution of MMAO-3A in heptane were combined in a glass vial containing a stir bar, and the reaction mixture was stirred vigorously at room temperature.

Then, 160 µL of heptane was dispensed into a 1 mL glass vial in which a magnetic stir bar had been placed. To the 1 mL glass vial containing the heptane was added 320 µL of the Composition M5/MMAO Mixture, approximately 7 minutes after combining the Composition M5 and MMAO-3A. After approximately 8 minutes, either 100 µL of heptane (for Example 4.1) or 100 µL of a 200 mM solution of TMA (Trimethylaluminum) in heptane (for Example 4.2) was added to the 1 mL vial and the reaction mixture was mixed. About another 30 seconds later, a fraction of the 1 mL vial contents corresponding to 0.60 micromoles (µmol) of metal precursor (435 µL), was injected into the prepressurized reaction vessel and was followed immediately by injection of heptane to bring the total volume injected to 1.0 mL.

The oligomerization reactions, workup, and product analysis were performed as described in Sections 6e and 6f above. The results are presented in Table 4. In Table 4, 1-hexene selectivity is shown as a percentage and is defined as 100× [micromoles of 1-hexene]/[sum of micromoles of $C_6$-$C_{16}$ olefins].

Example 7

Selective Ethylene Oligomerization Reactions in a 48-Well Parallel Pressure Reactor at Higher Pressure The ethylene oligomerization experiments described below were carried out in a parallel pressure reactor described in U.S. Pat. Nos. 6,759,014 and 6,913,934. All air-sensitive procedures were performed under a purified argon or nitrogen atmosphere in a Vacuum Atmospheres or MBraun glove box. All solvents used were anhydrous and de-oxygenated. All glassware and the disposable paddles were dried in a vacuum oven at 200° C. for at least 24 hours.

7a. Stock Solution & Suspension Preparation

Preparation of the Group 13 Reagent and Activator Stock Solutions

A 200 mM solution of DIBAL (diisobutylaluminum hydride) in heptane was prepared by combining 1.14 g of neat diisobutylaluminum hydride (purchased from Aldrich, Milwaukee, Wis.) and 38.6 mL of heptane. The 50 mM solution of DIBAL in heptane was prepared by further dilution of the 200 mM solution of DIBAL in heptane.

A 200 mM solution of TMA (trimethylaluminum) in heptane was prepared by combining 0.577 g of neat trimethylaluminum (purchased from Aldrich, Milwaukee, Wis.) and 39.2 mL of heptane. The 50 mM solution of TMA in heptane was prepared by further dilution of the 200 mM solution of TMA in heptane.

A 200 mM solution of TIBA (triisobutylaluminum) in heptane was prepared by combining 1.59 g of neat triisobutylaluminum (purchased from Aldrich, Milwaukee, Wis.) and 38.0 mL of heptane. The 50 mM solution of TIBA in heptane was prepared by further dilution of the 200 mM solution of TIBA in heptane.

A 200 mM solution of MMAO-3A in heptane was prepared by combining 2.20 mL of a 1.82 M solution of MMAO-3A in heptane (purchased from Akzo Chemical Inc., Chicago, Ill.) and 17.8 mL heptane.

TABLE 4

| Example | Composition | Reactor Preparation Method | Solvent | Reactor Temp (°C.) | Activation method and mole equivalents versus Cr | Group 13 reagent amount in reactor (micromole) | Reaction Time (min) | micromole 1-hexene produced | 1-hexene selectivity | 1-hexane TOF (mole/mole · hour) | mg polyethylene produced |
|---|---|---|---|---|---|---|---|---|---|---|---|
| 96 | M5 | C | Heptane | 80 | 200 MMAO-3A | 600 MMAO-3A | 15.6 | 4790 | 96 | 30800 | 2 |
| 97 | M5 | C | Heptane | 80 | 200 MMAO-3A/ 25 TMA | 600 MMAO-3A | 14.1 | 4700 | 96 | 33400 | 3 |

A 2.5 mM solution of "SJ2BF20" (N,N-di(n-decyl)-4-n-butyl-anilinium tetrakis(perfluorophenyl)borate, [(4-n-Bu-$C_6H_4$)NH(n-decyl)$_2$]$^+$[B($C_6F_5$)$_4$]$^-$) in toluene was prepared by dissolving 0.555 g of "SJ2BF20" in 20 mL of toluene.

A 2.5 mM solution of "TBF20" (trityl tetrakis(perfluorophenyl)borate, [($C_6H_5$)C]$^+$[B($C_6F_5$)$_4$]$^-$) (purchased from Boulder Scientific Co., Boulder Colo.) in toluene was prepared by dissolving 0.461 g of "TBF20" in 20 mL of toluene.

Preparation of Complex Solutions

For Example 7.1, 1.8 mg of Complex M13 was dissolved in 5.67 mL of toluene, in an 8 mL glass vial, to give a 0.625 mM solution. Solutions of the other complexes were prepared similarly, to give solutions with the concentrations shown in Table 5. Complex M31 was dissolved in heptane (Example 7.9), all others were dissolved in toluene, except Complexes M9 and M12 which were slurried in dodecane or heptane as described below.

Preparation of Complex Slurries:

4.5 mg of Complex M9 and 6.49 mL of dodecane were combined in a 8 mL glass vial. A slurry suspension (with a concentration equivalent to a molarity of 1.5 mM) was prepared by stirring the mixture vigorously for 90 minutes at room temperature, followed by sonication in an ultrasonic bath for 1 hour. The slurry was then vortexed at 1200 rpm to create a uniform suspension from which the complex slurry was sampled for injection into the reactor (Examples 7.15 & 7.20).

A suspension of Complex M12 in heptane was prepared similarly by suspending 3.1 mg of the complex in 4.33 mL heptane to give a suspension with a concentration equivalent to a molarity of 1.25 mM (Example 7.14).

7b. Reactor Preparation for Example 7.1

A pre-weighed, pre-dried, glass vial insert and disposable stirring paddle were fitted to each reaction vessel of the reactor. The reactor was then closed, 0.200 mL of a 50 mM solution of DIBAL in heptane and 3.925 mL of heptane (to achieve a total liquid volume of 5.10 mL after the catalyst injection step), were injected into the pressure reaction vessel through a mechanical septum. The temperature was then set to 80° C., and the stirring speed was set to 800 rpm, and the mixture was exposed to ethylene at 400 psi (2.76 MPa) pressure. An ethylene pressure of 400 psi (2.76 MPa) in the pressure cell and the temperature setting were maintained, using computer control, until the end of the selective oligomerization experiment.

Reactor Preparation for Other Examples in Table 5.

The reactor preparation for the other examples in Table 5 were performed similarly, except that 0.200 mL of 50 mM solutions of TMA or TIBA in heptane, or 0.050 mL of a 200 mM solution of MMAO-3A in heptane, or 0.250 mL of a 200 mM solution of TMA in heptane, were injected, to achieve the desired micromoles of Group 13 reagent listed in Table 5, followed by a suitable volume of heptane to achieve a total liquid volume of 5.10 mL after the Complex injection step.

7c. Injection of Activator Solution and Catalyst Solution into the Pressure Reactor Vessel for Example 7.1:

Activator Injection Step: 0.075 mL of a 200 mM solution of MMAO-3A in heptane was robotically aspirated into a needle (as described in U.S. Pat. Nos. 6,759,014 and 6,913,934), followed by the aspiration of 0.060 mL of heptane. The outside of the needle was sprayed with heptane, then the needle contents (heptane and MMAO-3A solution) were injected into the pressurized reaction vessel through a mechanical septum, followed immediately by injection of 0.240 mL of heptane.

Complex Injection Step: 0.080 mL of a 0.625 mM solution of Complex M13 in heptane was robotically aspirated from an 8 ml glass vial, followed by the aspiration of 0.104 mL of heptane. The outside of the needle was sprayed with heptane, then the needle contents (heptane and complex solution) were injected into the pressurized reaction vessel through a mechanical septum, followed immediately by injection of 0.416 mL of heptane, to bring the total volume injected to 0.600 mL. The Complex injection into the pressurized reaction vessel occurred 2 minutes after the Activator injection.

Injection of Activator Solution and Catalyst Solution or Slurry into the Pressure Reactor Vessel for Other Examples:

The Activator & Complex Injection procedure was performed in a similar fashion to the procedure described above, for other examples in Table 5. In the Examples where the Activator is MMAO-3A (abbreviated to MMAO in Table 5), a suitable volume of a 200 mM solution of MMAO-3A in heptane was injected, to achieve the specified molar equivalents of activator to complex in the pressurized reaction vessel. In the examples where the activator is "SJ2BF20" (N,N-di(n-decyl)-4-n-butyl-anilinium tetrakis(perfluorophenyl)borate, [(4-n-Bu-$C_6H_4$)NH(n-decyl)$_2$]$^+$[B($C_6F_5$)$_4$]$^-$) or "TBF20" (trityl tetrakis(perfluorophenyl)borate, [($C_6H_5$)C]$^+$[B($C_6F_5$)$_4$]$^-$), a suitable volume of a 2.5 mM solution of the activator reagent in toluene was injected, to achieve the specified molar equivalents of activator to complex in the pressurized reaction vessel.

The volume of complex solution (or slurry) injected into the pressurized reactor was calculated to achieve the specified micromoles of complex listed in Table 5. In the Examples 7.14, 7.15 and 7.20, in which a dodecane or heptane slurry of the complex was used, the slurry was vortexed at 1200 rpm, to achieve a uniform suspension, during the whole of the injection procedure.

7d. Oligomerization Reactions

The oligomerization reactions were allowed to continue for between 3 minutes and 60 minutes, during which time the temperature and pressure were maintained at their pre-set levels by computer control. The specific reaction times for each experiment are shown in Table 5. After the reaction time elapsed, the reaction was quenched by addition of an overpressure of oxygen (approximately 50 psi (0.34 MPa) of a 20% $O_2$/80% $N_2$ mixture) sent to the reactor. The reaction times were the lesser of the maximum desired reaction time or the time taken for a predetermined amount of ethylene gas to be consumed in the reaction.

7e. Product Analysis

After completion of the oligomerization reactions, the glass vial inserts containing the reaction products were removed from the pressure cell and removed from the inert atmosphere dry box, and deionized water (100 μL) was added. The glass vial inserts were then centrifuged for approximately 10 minutes. After centrifuging, 0.5 mL of the supernatant was then removed and analyzed by the GC-FID technique described above. The remaining supernatant was then decanted, and the vial insert containing insoluble residue was then placed in a centrifuge evaporator and the volatile components were removed. After the volatile components had evaporated, the vial contents were dried thoroughly (to constant weight) at elevated temperature (approximately 80° C.) under reduced pressure in a vacuum oven. The vial was then weighed to determine the mass of solid product (final weight minus vial tare weight). The calculated mass of the catalyst and cocatalyst residue was then subtracted from the total mass to give the yield of polyethylene produced, as listed in Table 5.

Table 5 presents the results from the ethylene oligomerization reactions performed in a 48-well parallel pressure reactor. In Table 5, 1-hexene selectivity is shown as a percentage and is defined as 100×[micromoles of 1-hexene]/[sum of micromoles of $C_6$-$C_{16}$ olefins]. Catalyst activity (Turn Over Frequency, TOF) for production of the desired oligomer (1-hexene) is defined as the [micromoles of 1-hexene]/([micromoles of catalyst]*[reaction time in minutes]/60), as shown in the column "1-hexene TOF". In Table 5, MMAO-3A is abbreviated to "MMAO".

All documents described herein are incorporated by reference herein, including any priority documents and/or testing procedures. As is apparent from the foregoing general description and the specific embodiments, while forms of the invention have been illustrated and described, various modifications can be made without departing from the spirit and scope of the invention. Accordingly, it is not intended that the invention be limited thereby.

TABLE 5

| Example # | Ligand # | Complex # | Complex Solution Solvent (or Slurry Diluent) | Complex Concentration (mM) | micromoles of Complex | micromoles of Group 13 Reagent | Molar Equivalents of Activator (vs. Complex) | Reaction Time (mins) | micromoles of 1-Hexene | 1-Hexene TOF (per hr) | 1-Hexene Selectivity (%) | Polyethylene (mg) |
|---|---|---|---|---|---|---|---|---|---|---|---|---|
| 7.1 | A29 | M13 | toluene | 0.625 | 0.05 | 10 DIBAL | 300 MMAO | 15.6 | 7,400 | 571,000 | 97.9 | 2.4 |
| 7.2 | A29 | M37 | toluene | 0.625 | 0.05 | 10 DIBAL | 500 MMAO | 21.4 | 5,550 | 312,000 | 97.7 | 2.0 |
| 7.3 | A29 | M35 | toluene | 0.625 | 0.05 | 10 DIBAL | 500 MMAO | 22.7 | 5,780 | 306,000 | 98.0 | 2.3 |
| 7.4 | A29 | M34 | toluene | 0.625 | 0.05 | 10 DIBAL | 300 MMAO | 16.4 | 4,340 | 318,000 | 97.5 | 2.4 |
| 7.5 | A29 | M8 | toluene | 2.5 | 0.1 | 10 TMA | 500 MMAO | 8.7 | 2,020 | 140,000 | 98.8 | 2.1 |
| 7.6 | A53 | M14 | toluene | 0.625 | 0.05 | 10 DIBAL | 300 MMAO | 15.1 | 6,670 | 531,000 | 98.3 | 0.8 |
| 7.7 | A53 | M38 | toluene | 0.625 | 0.05 | 10 DIBAL | 500 MMAO | 31.2 | 5,690 | 219,000 | 98.8 | 2.5 |
| 7.8 | A53 | M36 | toluene | 0.625 | 0.05 | 10 DIBAL | 500 MMAO | 24.2 | 5,660 | 281,000 | 98.7 | 3.0 |
| 7.9 | A55 | M31 | heptane | 0.625 | 0.02 | 10 DIBAL | 500 MMAO | 30.0 | 7,020 | 703,000 | 98.2 | 2.5 |
| 7.10 | A55 | M10 | toluene | 0.625 | 0.1 | 10 DIBAL | 300 MMAO | 16.3 | 5,220 | 192,000 | 97.9 | 2.7 |
| 7.11 | A54 | M20 | toluene | 0.625 | 0.05 | 10 DIBAL | 300 MMAO | 15.2 | 7,420 | 584,000 | 98.3 | 2.1 |
| 7.12 | A54 | M20 | toluene | 0.625 | 0.03 | 10 DIBAL | 500 MMAO | 25.2 | 6,310 | 502,000 | 98.7 | 1.7 |
| 7.13 | A56 | M32 | toluene | 2.5 | 0.2 | 10 TMA | 550 MMAO | 6.3 | 2,100 | 99,900 | >99.9 | 1.3 |
| 7.14 | A42 | M12 | heptane slurry | 1.25 | 0.1 | 10 DIBAL | 500 MMAO | 51.4 | 4,800 | 56,000 | 98.0 | 29 |
| 7.15 | A53 | M9 | dodecane slurry | 1.5 | 0.1 | 10 MMAO | 500 MMAO | 7.2 | 1,930 | 161,000 | 99.7 | 6.5 |
| 7.16 | A53 | M14 | toluene | 1.5 | 0.1 | 10 MMAO | 500 MMAO | 3.2 | 2,140 | 406,000 | 99.2 | 6.4 |
| 7.17 | A53 | M14 | toluene | 1.5 | 0.1 | 10 TMA | 500 MMAO | 3.4 | 2,360 | 418,000 | 99.4 | 0.4 |
| 7.18 | A53 | M14 | toluene | 1.5 | 0.1 | 10 TIBA | 500 MMAO | 3.2 | 2,280 | 429,000 | 99.5 | 0.8 |
| 7.19 | A53 | M14 | toluene | 1.5 | 0.1 | 10 DIBAL | 500 MMAO | 3.1 | 2,210 | 429,000 | 99.6 | 2.7 |
| 7.20 | A53 | M9 | dodecane slurry | 1.5 | 0.1 | 10 MMAO | 500 MMAO | 22.5 | 6,160 | 164,000 | 98.5 | 5.8 |
| 7.21 | A53 | M14 | toluene | 1.5 | 0.1 | 10 MMAO | 500 MMAO | 10.7 | 6,310 | 355,000 | 98.0 | 5.1 |
| 7.22 | A53 | M14 | toluene | 1.5 | 0.1 | 10 TMA | 500 MMAO | 10.3 | 6,410 | 373,000 | 98.3 | 0.2 |
| 7.23 | A53 | M14 | toluene | 1.5 | 0.1 | 10 TIBA | 500 MMAO | 10.3 | 6,620 | 385,000 | 98.5 | 2.0 |
| 7.24 | A53 | M14 | toluene | 1.5 | 0.1 | 10 DIBAL | 500 MMAO | 10.2 | 5,440 | 321,000 | 97.8 | 1.2 |
| 7.25 | A53 | M14 | toluene | 2.0 | 0.1 | 50 TMA | 2 SJ2BF20 | 60.0 | 337 | 3,370 | 99.3 | 0.3 |
| 7.26 | A53 | M14 | toluene | 2.0 | 0.1 | 50 TMA | 2 TBF20 | 60.0 | 651 | 6,510 | 99.7 | 1.4 |

As discussed herein, catalytic performance can be determined a number of different ways, as those of skill in the art will appreciate. Catalytic performance can be determined by the yield of oligomer (for example, trimer or tetramer) obtained per mole of metal complex, which in some contexts may be considered to be activity.

The results of selective ethylene trimerization or tetramerization using ligands of the invention in combination with chromium precursors or with isolated chromium metal complexes are surprising. The results illustrate that certain combinations are more productive in the trimerization of ethylene, for example, to produce 1-hexene at a higher selectivity and a lower selectivity toward polyethylene when compared with other chromium-ligand catalysts under similar conditions.

The invention claimed is:

1. A composition comprising:
   (1) a ligand characterized by the following general formula:

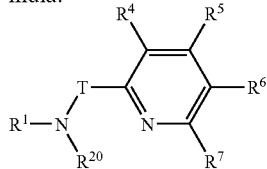

wherein $R^1$ and $R^{20}$ are each independently selected from the group consisting of hydrogen and optionally substituted methyl, ethyl, propyl, butyl, pentyl, hexyl, octyl, decyl and dodecyl groups;

T is a bridging group of the general formula —(T'$R^2R^3$)—, where T' is selected from the group consisting of carbon and silicon, $R^2$ and $R^3$ are independently selected from the group consisting of hydrogen, halogen, and optionally substituted alkyl, heteroalkyl, aryl, heteroaryl, alkoxy, aryloxy, silyl, boryl, phosphino, amino, alkylthio, arylthio, cyclo-alkyl, and combinations thereof, provided that two or more $R^2$ and/or $R^3$ groups may be joined together to form one or more optionally substituted ring systems having from 3-50 non-hydrogen atoms;

$R^4$, $R^5$, $R^6$ and $R^7$ are independently selected from the group consisting of hydrogen, halogen, nitro, and optionally substituted alkyl, heteroalkyl, aryl, heteroaryl, alkoxy, aryloxy, silyl, boryl, phosphino, amino, alkylthio, arylthio, and combinations thereof, and optionally two or more $R^1$, $R^{20}$, $R^2$, $R^3$, $R^4$, $R^5$, $R^6$ and $R^7$ groups may be joined to form one or more optionally substituted ring systems (2) a metal precursor compound characterized by the general formula Cr(L)$_n$ where each L is independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, wherein two or more L groups may be combined in a ring structure having from 3 to 50 non-hydrogen atoms; n is 1, 2, 3, 4, 5, or 6; and (3) optionally, one or more activators.

2. The composition of claim 1, wherein $R^7$ is selected from the group consisting of optionally substituted aryl and heteroaryl.

3. The composition of claim 1, wherein $R^3$ is selected from the group consisting of hydrogen and optionally substituted alkyl, heteroalkyl, cycloalkyl, heterocycloalkyl, silyl and combinations thereof.

4. The composition of claim 1, wherein $R^5$ is selected from the group consisting of —$CF_3$, H, F, Cl, —$N(Me)_2$ and —OR, wherein R is an optionally substituted alkyl group, an optionally substituted benzyl group or an optionally substituted aryl group.

5. The composition of claim 1, wherein T' is carbon; $R^2$ and $R^3$ are independently selected from the group consisting of hydrogen, optionally-substituted alkyl, aryl, cyclo-alkyl and combinations thereof; $R^{20}$ is hydrogen; and $R^1$ is optionally substituted alkyl.

6. The composition of claim 5, wherein $R^4$, $R^5$, and $R^6$ are hydrogen; and $R^7$ is optionally substituted aryl.

7. The composition of claim 1, wherein $R^1$ and $R^{20}$ are independently an optionally substituted alkyl; T' is carbon; $R^2$ and $R^3$ are each independently hydrogen, cyclo-alkyl, or optionally substituted alkyl; and $R^7$ is aromatic with at least one C-H bond.

8. The composition of claim 1, wherein the activator is an alumoxane, which mat optionally be used in any combination with group 13 reagents, divalent metal reagents, alkali metal reagents or combinations thereof.

9. The composition of claim 1, wherein the activator is selected from the group consisting of modified methylaluminoxane (MMAO), methylaluminoxane (MAO), trimethylaluminum (TMA), triisobutyl aluminum (TIBA), diisobutylaluminumhydride (DIBAL), polymethylaluminoxane-IP (PMAO), triphenylcarbonium tetrakis(perfluorophenyl)borate, N,N-dimethyl-anilinium tetrakis(perfluorophenyl)borate N,N-di(n-decyl)-4-n-buty-anilinium tetrakis(perfluorophenyl)borate, and mixtures thereof.

* * * * *